(12) United States Patent
Cai et al.

(10) Patent No.: US 10,266,876 B2
(45) Date of Patent: Apr. 23, 2019

(54) MULTIPLEX DETECTION OF MOLECULAR SPECIES IN CELLS BY SUPER-RESOLUTION IMAGING AND COMBINATORIAL LABELING

(71) Applicant: California Institute of Technology, Pasadena, CA (US)

(72) Inventors: Long Cai, Port Jefferson Station, NY (US); Eric Lubeck, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/725,717

(22) Filed: Dec. 21, 2012

(65) Prior Publication Data

US 2014/0031243 A1    Jan. 30, 2014

Related U.S. Application Data

(63) Continuation-in-part of application No. 13/043,413, filed on Mar. 8, 2011.

(60) Provisional application No. 61/311,654, filed on Mar. 8, 2010, provisional application No. 61/579,772, filed on Dec. 23, 2011.

(51) Int. Cl.
    *C12Q 1/68*     (2018.01)
    *C12Q 1/6809*   (2018.01)
    *C12Q 1/6841*   (2018.01)

(52) U.S. Cl.
    CPC ......... *C12Q 1/6809* (2013.01); *C12Q 1/6841* (2013.01)

(58) Field of Classification Search
    USPC ................. 435/6.1, 6.11, 91.1; 436/94, 501; 536/23.1, 24.3, 24.33
    See application file for complete search history.

(56) References Cited

U.S. PATENT DOCUMENTS

| 6,534,266 B1 * | 3/2003 | Singer .............................. 506/4 |
| 2003/0064025 A1 | 4/2003 | Yang et al. |
| 2003/0152490 A1 | 8/2003 | Trulson et al. |
| 2003/0170613 A1 | 9/2003 | Straus |
| 2004/0171076 A1 | 9/2004 | Dejneka et al. |
| 2004/0229253 A1 * | 11/2004 | Hyldig-Nielsen et al. ....... 435/6 |

(Continued)

FOREIGN PATENT DOCUMENTS

| WO | 2011112634 | 9/2011 |
| WO | 2012058638 A2 | 5/2012 |

OTHER PUBLICATIONS

Donnert et al., PNAS, 103, 11440-11445, 2006.*

(Continued)

*Primary Examiner* — Frank W Lu
(74) *Attorney, Agent, or Firm* — Squire Patton Boggs (US) LLP

(57) ABSTRACT

Methods and systems are provided for creating molecular barcodes or indicia for cellular constituents within single cells and for resolving such barcodes or indicia with super-resolution technologies such as super-resolution microscopy. By this approach, numerous molecular species that can be measured simultaneously in single cells. It has been demonstrated that multiple mRNA transcripts can be labeled with a spatially ordered sequence of fluorophores, and that barcodes can be resolved. In addition, alternative splicing events can be characterized by identifying and quantifying mRNA isoforms in an individual cell.

11 Claims, 45 Drawing Sheets

Specification includes a Sequence Listing.

(56) References Cited

U.S. PATENT DOCUMENTS

2004/0253593 A1* 12/2004 Cai et al. .................. 435/6
2012/0142014 A1 6/2012 Cai et al.

OTHER PUBLICATIONS

PCT/US2011/027618 International Search Report and Written Opinion dated Jan. 2, 2012; 9 pages.
PCT/US2011/027618 International Preliminary Report on Patentability dated Sep. 11, 2012; 5 pages.
Blanco et al. A FRET-based assay for characterization of alternative splicing events using peptide nucleic acid fluorescence in situ hybridization. Nucleic Acids Research (2009). 37(17): e116; 11 pages.
Donnert et al. Macromolecular-scale resolution in biological fluorescence microscopy. PNAS (2006). 103(31):11440-11445.
Femino et al. Visualization of Single RNA Transcipts in Situ. Science (1998). 280:585-590.
Fernandez-Suarez et al. Fluorescent probes for super-resolution imaging in living cells. Nature Reviews (2008). 9:929-944.
Levsky et al. Single-Cell Gene Expression Profiling. Science (2002). 297:836-840.
Lu et al. Quantification of miRNA Abundance in Single Cells Using Locked Nucleic Acid—FISH and Enzyme-Labeled Fluorescence. Methods in Molecular Imaging (2010). 680:77-88.
Lubeck et al. Single-cell systems biology by super-resolution imaging and combinatorial labeling. Nature Methods (2012). 9(7):743-748.
National Aeronautics and Space Administration. What Wavelength Goes With a Color? Retrieved from: http://science-edu.larc.nasa.gov/EDDOCS/Wavelengths_for_Colors.html on Aug. 19, 2012. 4 pages.
No Author. Table of Fluorochromes. Retrieved from: http://flowcyt.salk.edu/fluo.html on Aug. 19, 2012. 6 pages.
Rust et al. Sub-diffraction-limit imaging by stochastic optical reconstruction microscopy (STORM). Nature Methods (2006). 3(10):793-795.
Yildiz et al. Fluorescence Imaging with One Nanometer Accuracy: Application to Molecular Motors. Accounts of Chemical Research (2005). 38:574-582.

* cited by examiner

SEQUENCE LISTING

<160> NUMBER OF SEQ ID NOS: 58

<210> SEQ ID NO 1
<211> LENGTH: 26
<212> TYPE: DNA
<213> ORGANISM: S. cerevisiae

<400> SEQUENCE: 1
gatctcacgc tacaccatag aatgaa                                       26

<210> SEQ ID NO 2
<211> LENGTH: 26
<212> TYPE: DNA
<213> ORGANISM: S. cerevisiae

<400> SEQUENCE: 2

-continued catcaaaccc tggtagttcc taccaa                                          26

<210> SEQ ID NO 3
<211> LENGTH: 26
<212> TYPE: DNA
<213> ORGANISM: S. cerevisiae

<400> SEQUENCE: 3
tatgctttag gatgtatttg atgtat                                          26

<210> SEQ ID NO 4
<211> LENGTH: 26
<212> TYPE: DNA
<213> ORGANISM: S. cerevisiae

<400> SEQUENCE: 4
actaataggg cggcaaaggc gaaaaa                                          26

<210> SEQ ID NO 5
<211> LENGTH: 26
<212> TYPE: DNA
<213> ORGANISM: S. cerevisiae

<400> SEQUENCE: 5
ccttatgtgg atgatccagc gcaata                                          26

<210> SEQ ID NO 6
<211> LENGTH: 26
<212> TYPE: DNA
<213> ORGANISM: S. cerevisiae

<400> SEQUENCE: 6
caataccaat aagaatggta atgaac                                          26

<210> SEQ ID NO 7
<211> LENGTH: 26
<212> TYPE: DNA
<213> ORGANISM: S. cerevisiae

<400> SEQUENCE: 7
attttacttt ttagtttttc gggcaa                                          26

<210> SEQ ID NO 8
<211> LENGTH: 26
<212> TYPE: DNA
<213> ORGANISM: S. cerevisiae

<400> SEQUENCE: 8
cagagcctca ttgttgttga tattgt                                          26

<210> SEQ ID NO 9
<211> LENGTH: 26
<212> TYPE: DNA
<213> ORGANISM: S. cerevisiae

<400> SEQUENCE: 9
ggataccgtg aggcgaagaa catgat                                          26

<210> SEQ ID NO 10
<211> LENGTH: 26
<212> TYPE: DNA
<213> ORGANISM: S. cerevisiae

```
<400> SEQUENCE: 10
tacgaccaaa gccctatatt tatata                                          26

<210> SEQ ID NO 11
<211> LENGTH: 26
<212> TYPE: DNA
<213> ORGANISM: S. cerevisiae

<400> SEQUENCE: 11
agaactcaaa gaagggagca ccgtcg                                          26

<210> SEQ ID NO 12
<211> LENGTH: 26
<212> TYPE: DNA
<213> ORGANISM: S. cerevisiae

<400> SEQUENCE: 12
cacagtaaat tttatttatg ggactg                                          26

<210> SEQ ID NO 13
<211> LENGTH: 25
<212> TYPE: DNA
<213> ORGANISM: S. cerevisiae

<400> SEQUENCE: 13
acggacgcta ccttaccgtt gactg                                           25

<210> SEQ ID NO 14
<211> LENGTH: 25
<212> TYPE: DNA
<213> ORGANISM: S. cerevisiae

<400> SEQUENCE: 14
tgtagaacct gacgtagtgg tataa                                           25

<210> SEQ ID NO 15
<211> LENGTH: 25
<212> TYPE: DNA
<213> ORGANISM: S. cerevisiae

<400> SEQUENCE: 15
ttgattccgg ttttgatgag gatcc                                           25

<210> SEQ ID NO 16
<211> LENGTH: 25
<212> TYPE: DNA
<213> ORGANISM: S. cerevisiae

<400> SEQUENCE: 16
tcagttgtgg ctgaggacgg tagcc                                           25

<210> SEQ ID NO 17
<211> LENGTH: 25
<212> TYPE: DNA
<213> ORGANISM: S. cerevisiae

<400> SEQUENCE: 17
cgaattcgtg gtagttacta tagta                                           25

<210> SEQ ID NO 18
<211> LENGTH: 25
<212> TYPE: DNA
<213> ORGANISM: S. cerevisiae
```

```
<400> SEQUENCE: 18
aggaggatgc ggagttggtg attcc                                          25

<210> SEQ ID NO 19
<211> LENGTH: 25
<212> TYPE: DNA
<213> ORGANISM: S. cerevisiae

<400> SEQUENCE: 19
gcagttgaag ttgtgcttac ggcag                                          25

<210> SEQ ID NO 20
<211> LENGTH: 25
<212> TYPE: DNA
<213> ORGANISM: S. cerevisiae

<400> SEQUENCE: 20
tgtcgtggtt ttgccttgtg catcc                                          25

<210> SEQ ID NO 21
<211> LENGTH: 25
<212> TYPE: DNA
<213> ORGANISM: S. cerevisiae

<400> SEQUENCE: 21
cataggtgtt gctgacgacg ttgct                                          25

<210> SEQ ID NO 22
<211> LENGTH: 25
<212> TYPE: DNA
<213> ORGANISM: S. cerevisiae

<400> SEQUENCE: 22
acagttgatg cgctttcttg ggctt                                          25

<210> SEQ ID NO 23
<211> LENGTH: 25
<212> TYPE: DNA
<213> ORGANISM: S. cerevisiae

<400> SEQUENCE: 23
gtttgagctt tccttttgtg agcta                                          25

<210> SEQ ID NO 24
<211> LENGTH: 25
<212> TYPE: DNA
<213> ORGANISM: S. cerevisiae

<400> SEQUENCE: 24
agtctttttg agcagcggct agagt                                          25

<210> SEQ ID NO 25
<211> LENGTH: 25
<212> TYPE: DNA
<213> ORGANISM: S. cerevisiae

<400> SEQUENCE: 25
atgcagactt caatttcatt tgctc                                          25

<210> SEQ ID NO 26
<211> LENGTH: 25
<212> TYPE: DNA
```

<213> ORGANISM: S. cerevisiae

<400> SEQUENCE: 26
tgcagacgta aatcatccaa cgaat                                  25

<210> SEQ ID NO 27
<211> LENGTH: 25
<212> TYPE: DNA
<213> ORGANISM: S. cerevisiae

<400> SEQUENCE: 27
ggaattctct tctatatcgt tatcg                                  25

<210> SEQ ID NO 28
<211> LENGTH: 25
<212> TYPE: DNA
<213> ORGANISM: S. cerevisiae

<400> SEQUENCE: 28
acctcttaat tctattatta agctt                                  25

<210> SEQ ID NO 29
<211> LENGTH: 25
<212> TYPE: DNA
<213> ORGANISM: S. cerevisiae

<400> SEQUENCE: 29
cgcaaagaaa acccttttctt aacgt                                 25

<210> SEQ ID NO 30
<211> LENGTH: 25
<212> TYPE: DNA
<213> ORGANISM: S. cerevisiae

<400> SEQUENCE: 30
tgaagtaatc catggatcgt ccagc                                  25

<210> SEQ ID NO 31
<211> LENGTH: 25
<212> TYPE: DNA
<213> ORGANISM: S. cerevisiae

<400> SEQUENCE: 31
tcaatctcaa tgccttcaag atgaa                                  25

<210> SEQ ID NO 32
<211> LENGTH: 25
<212> TYPE: DNA
<213> ORGANISM: S. cerevisiae

<400> SEQUENCE: 32
tatggcatat ggaaggttac cgggt                                  25

<210> SEQ ID NO 33
<211> LENGTH: 25
<212> TYPE: DNA
<213> ORGANISM: S. cerevisiae

<400> SEQUENCE: 33
ttcaacgctt tcggcaataa aagga                                  25

<210> SEQ ID NO 34
<211> LENGTH: 25

```
<212> TYPE: DNA
<213> ORGANISM: S. cerevisiae

<400> SEQUENCE: 34
caccaatgga ccatatatca caagg                                              25

<210> SEQ ID NO 35
<211> LENGTH: 25
<212> TYPE: DNA
<213> ORGANISM: S. cerevisiae

<400> SEQUENCE: 35
ggtgccacat aacccaacga tccgg                                              25

<210> SEQ ID NO 36
<211> LENGTH: 25
<212> TYPE: DNA
<213> ORGANISM: S. cerevisiae

<400> SEQUENCE: 36
caattgttta gctataccga agtcc                                              25

<210> SEQ ID NO 37
<211> LENGTH: 21
<212> TYPE: DNA
<213> ORGANISM: S. cerevisiae

<400> SEQUENCE: 37
tcgcctctgg taattgcgga c                                                  21

<210> SEQ ID NO 38
<211> LENGTH: 20
<212> TYPE: DNA
<213> ORGANISM: S. cerevisiae

<400> SEQUENCE: 38
taacccaacg atccggctgc                                                    20

<210> SEQ ID NO 39
<211> LENGTH: 20
<212> TYPE: DNA
<213> ORGANISM: S. cerevisiae

<400> SEQUENCE: 39
ttgttgcggt cactggcgat                                                    20

<210> SEQ ID NO 40
<211> LENGTH: 20
<212> TYPE: DNA
<213> ORGANISM: S. cerevisiae

<400> SEQUENCE: 40
aagcctctct ggcaacctcc                                                    20

<210> SEQ ID NO 41
<211> LENGTH: 21
<212> TYPE: DNA
<213> ORGANISM: S. cerevisiae

<400> SEQUENCE: 41
gctacgctat cttcgttggg c                                                  21

<210> SEQ ID NO 42
```

-continued

```
<211> LENGTH: 21
<212> TYPE: DNA
<213> ORGANISM: S. cerevisiae

<400> SEQUENCE: 42
ctggataccg tgaggcgaag a                                           21

<210> SEQ ID NO 43
<211> LENGTH: 21
<212> TYPE: DNA
<213> ORGANISM: S. cerevisiae

<400> SEQUENCE: 43
agcaactctg ccgtaagcac a                                           21

<210> SEQ ID NO 44
<211> LENGTH: 20
<212> TYPE: DNA
<213> ORGANISM: S. cerevisiae

<400> SEQUENCE: 44
gtcgttgagg aggatgcgga                                             20

<210> SEQ ID NO 45
<211> LENGTH: 20
<212> TYPE: DNA
<213> ORGANISM: S. cerevisiae

<400> SEQUENCE: 45
gggagatcct gccactgtga                                             20

<210> SEQ ID NO 46
<211> LENGTH: 20
<212> TYPE: DNA
<213> ORGANISM: S. cerevisiae

<400> SEQUENCE: 46
aggtccatct gtgcgcttcg                                             20

<210> SEQ ID NO 47
<211> LENGTH: 20
<212> TYPE: DNA
<213> ORGANISM: S. cerevisiae

<400> SEQUENCE: 47
acgatgggag gctgagggtc                                             20

<210> SEQ ID NO 48
<211> LENGTH: 20
<212> TYPE: DNA
<213> ORGANISM: S. cerevisiae

<400> SEQUENCE: 48
accccaaact ttccctcgca                                             20

<210> SEQ ID NO 49
<211> LENGTH: 20
<212> TYPE: DNA
<213> ORGANISM: S. cerevisiae

<400> SEQUENCE: 49
ggcgataaaa cgggcactga                                             20
```

```
<210> SEQ ID NO 50
<211> LENGTH: 21
<212> TYPE: DNA
<213> ORGANISM: S. cerevisiae

<400> SEQUENCE: 50
aggcgacaac caagtgacca a                                              21

<210> SEQ ID NO 51
<211> LENGTH: 19
<212> TYPE: DNA
<213> ORGANISM: S. cerevisiae

<400> SEQUENCE: 51
ttgacgggaa cgggcagtg                                                 19

<210> SEQ ID NO 52
<211> LENGTH: 20
<212> TYPE: DNA
<213> ORGANISM: S. cerevisiae

<400> SEQUENCE: 52
ccgaagcagg cacggattga                                                20

<210> SEQ ID NO 53
<211> LENGTH: 19
<212> TYPE: DNA
<213> ORGANISM: S. cerevisiae

<400> SEQUENCE: 53
acgtttccat ccaagccgt                                                 19

<210> SEQ ID NO 54
<211> LENGTH: 21
<212> TYPE: DNA
<213> ORGANISM: S. cerevisiae

<400> SEQUENCE: 54
ggaacgacgt gagtaacacc a                                              21

<210> SEQ ID NO 55
<211> LENGTH: 25
<212> TYPE: DNA
<213> ORGANISM: S. cerevisiae

<400> SEQUENCE: 55
ggtccccttt atggtatgtt tattg                                          25

<210> SEQ ID NO 56
<211> LENGTH: 24
<212> TYPE: DNA
<213> ORGANISM: S. cerevisiae

<400> SEQUENCE: 56
tttgactgca ggatcctatg atat                                           24

<210> SEQ ID NO 57
<211> LENGTH: 22
<212> TYPE: DNA
<213> ORGANISM: S. cerevisiae

<400> SEQUENCE: 57 ccccttttatg gatcctgcag tc                                            22
```

```
<210> SEQ ID NO 58
<211> LENGTH: 20
<212> TYPE: DNA
<213> ORGANISM: S. cerevisiae

<400> SEQUENCE: 58
cctgattggc tacctgaact                                               20
```

MULTIPLEX DETECTION OF MOLECULAR SPECIES IN CELLS BY SUPER-RESOLUTION IMAGING AND COMBINATORIAL LABELING

CROSS-REFERENCE TO RELATED APPLICATIONS

This application is a continuation-in-part of U.S. patent application Ser. No. 13/043,413, filed on Mar. 8, 2011, now pending, which claims the benefit of U.S. Provisional Patent Application No. 61/311,654, filed on Mar. 8, 2010, now expired. This application also claims the benefit of U.S. Provisional Patent Application No. 61/579,772, filed on Dec. 23, 2011. All of the aforementioned applications are incorporated herein by reference in their entirety.

STATEMENT REGARDING FEDERALLY-SPONSORED RESEARCH

The U.S. Government has a paid-up license in this invention and the right in limited circumstances to require the patent owner to license others on reasonable terms as provided for by the terms of Grant Nos.: GM087588 and 1DP2OD008530, awarded by National Institutes of Health.

FIELD OF THE INVENTION

The invention disclosed herein generally relates to methods and systems that analyze biological systems in microscopic and macroscopic scales at the same time. Specifically, the invention disclosed herein relates to methods and systems that combine the power and advantages of genomics and single cells analyses. More specifically, the invention disclosed herein relates to methods and systems that encode cellular constituents with indicia based on genomics and then employ powerful tools such as super resolution microscopes that can resolve such indicia.

BACKGROUND

Advances in genomic research have revolutionized the fields of biology, genetics, and biochemistry. In particular, microarray technologies have enabled the study of molecular interactions at a large scale. As the collective understanding of biological systems progress, it is increasingly important that molecular interactions are understood both macroscopically and microscopically in a systematic fashion.

As a field of study, system biology is the study of the interactions between the components of biological systems, and how these interactions give rise to the function and behavior of that system (for example, the enzymes and metabolites in a metabolic pathway).

Current tools for macroscopic and systematic analyses of biological systems require tremendous input in both resource and manpower. There is a need in the art for methods and systems that can carry out such analyses with more efficiency and economy.

SUMMARY OF THE INVENTION

In various embodiments, the invention teaches a method for characterizing one or more mRNA isoforms in a single cell, including: (i) creating a molecular barcode for each of said one or more mRNA isoforms in the cell, comprising: (a) providing two or more sets of two or more fluorophore-labeled oligonucleotide probes, wherein each set of probes are configured to hybridize with a specific region of one or more mRNA isoforms; and (b) hybridizing, within said cell, a quantity of said one or more mRNA isoforms with a quantity of said probes specific thereto, wherein each mRNA isoform that is hybridized with said fluorophore-labeled oligonucleotide probes emits two or more distinct signals, so as to create the molecular barcode; and (ii) resolving the molecular barcode, comprising resolving the signals emitted from the fluorophore-labeled oligonucleotide probes associated with each of said mRNA isoforms, using super resolution technology, wherein each emitted signal is a component of the barcode associated with said mRNA isoform, and wherein each mRNA isoform is associated with a distinct barcode, such that each mRNA isoform can be characterized. In certain embodiments, centroid fitting is used to determine spatial ordering of the fluorophore-labeled oligonucleotide probes. In some embodiments, the method includes quantifying one or more mRNA isoforms contained in a single cell, by counting the number of times each distinct barcode is detected. In some embodiments, each of the two or more sets of probes includes four or more fluorophore-labeled oligonucleotides. In some embodiments, the mRNA isoform is correlated with a gene associated with neuronal patterning or tumorigenesis. In some embodiments, the method further includes compressing the cell. In some embodiments, the method includes selecting said two or more sets of fluorophore-labeled oligonucleotide probes based upon a characteristic of said one or more mRNA isoforms, wherein said characteristic is selected from the group consisting of sequence, size, abundance level, activity level, two-dimensional structure, three-dimensional structure, and a combination thereof. In some embodiments, the cell is selected from the group consisting of a protist, a fungus, a plant cell, an animal cell, a mammalian cell, a mouse cell, a human cell, a cancer cell, a blood cell, a lymphocyte, an erythrocyte, a white blood cell, an epithelial cell, a pituitary cell, a gut or respiratory tract cell, a gland cell, a thyroid gland cell, a parathyroid gland cell, a adrenal gland cell, a muscle cell, a ciliated cell, an embryonic cell, a sensory transducer cell, a neuron, a glial cell, a lens cell, a kidney cell, a pigment cell, and a pancreatic cell. In some embodiments, the fluorophore is selected from the group consisting of fluorescein, rhodamine, Alexa Fluors, DyLight fluors, ATTO Dyes, and any analogs or derivatives thereof. In some embodiments, the super resolution technology is selected from the group consisting of Stimulated Emission Depletion microscopy (STEDM), Ground State Depletion microscopy (GSDM), Spatially Structured Illumination microscopy (SSIM), Photo-Activated Localization Microscopy (PALM), Fluorescence-PALM (FPALM), Stochastical Optical Reconstruction Microscopy (STORM), Fluorescence Imaging with One-Nanometer Accuracy (FIONA), and combinations thereof.

In various embodiments, the invention teaches a system for characterizing one or more mRNA isoforms in a single cell, including: (i) two or more sets of two or more fluorophore-labeled oligonucleotide probes that are each configured to hybridize to a particular region of one or more mRNA isoforms, wherein each of said fluorophores is capable of emitting a signal, and wherein the signals emitted from each of the fluorophores associated with the sets of probes can be used to identify and quantify one or more mRNA isoforms in a single cell; and (ii) imaging equipment employing super-resolution technology. In certain embodiments, each set of fluorophore-labeled oligonucleotide probes includes 4 oligonucleotides. In some embodiments, one or more of the mRNA isoforms is correlated with a gene associated with neuronal patterning or tumorigenesis. In some embodiments, the cell is selected from the group consisting of a protist, a fungus, a plant cell, an animal cell, a mammalian cell, a mouse cell, a human cell, a cancer cell, a blood cell, a lymphocyte, an erythrocyte, a white blood cell, an epithelial cell, a pituitary cell, a gut or respiratory tract cell, a gland cell, a thyroid gland cell, a parathyroid gland cell, an adrenal gland cell, a muscle cell, a ciliated cell, an embryonic cell, a sensory transducer cell, a neuron, a glial cell, a lens cell, a kidney cell, a pigment cell, and a pancreatic cell. In some embodiments, the fluorophore is selected from the group consisting of fluorescein, rhodamine, Alexa Fluors, DyLight fluors, ATTO Dyes, and any analogs or derivatives thereof.

BRIEF DESCRIPTION OF THE DRAWINGS

Those of skill in the art will understand that the drawings, described below, are for illustrative purposes only. The drawings are not intended to limit the scope of the present teachings in any way.

FIGS. 9A-F depict, in accordance with an embodiment of the invention, super-resolution imaging enables combinatorial labeling of individual transcripts. A) Schematic of STORM barcoding scheme. For each STORM color, four acceptor/emitter pairs are hybridized in sequence for redundancy. B) Each barcode color consists of an activator (Alexa 405, 488, and Cy3) labeled oligo adjacent to a 5' emitter (Cy5, Cy5.5 and Cy7) labeled oligo. C) YLR414c mRNA 3 position barcode. The order of the probes is shown schematically in the cartoon. A histogram of the STORM reconstruction of a single barcode is shown along with a localization scatterplot in which each dot represents an activation of a STORM fluorophore. D) YPS1 mRNA 3 position barcodes with 3 different emitters. E) RCN2 mRNA spectral 3 Position Barcode. Probe Positions are scattered throughout the mRNA, enabling robust hybridization and identification by unique combinations of fluorophores. Histograms show the intensity detected for each fluorophore in the barcode. Cy5-A405, Cy5-A488, Cy5-Cy3 and Cy7-Cy3 are detected with 6195, 471, 6881 and 235 counts respectively. Cy5-A488 (green and crossed) is a false-positive detected due to cross-talk from Cy5-Cy3 (blue), based on the threshold measurements in FIG. 18, and is rejected in the barcode determination. Note the Cy7 based dye pairs give significantly fewer photons than Cy5 dye pairs, but are readily detected with less crosstalk. F) YLR194c mRNA combinatorial 3 position barcode. Cy5-A488, Cy5-Cy3, Cy7-Cy3 and Cy5.5-Cy3 are detected with 773, 999, 130 and 92 counts respectively. Cy5.5-Cy3 (yellow and crossed) was determined to be a false positive due to the low amount of photon emission and presence of Cy5-Cy3, a color it can significantly cross-talk with.

DETAILED DESCRIPTION OF THE INVENTION

Figure 1:
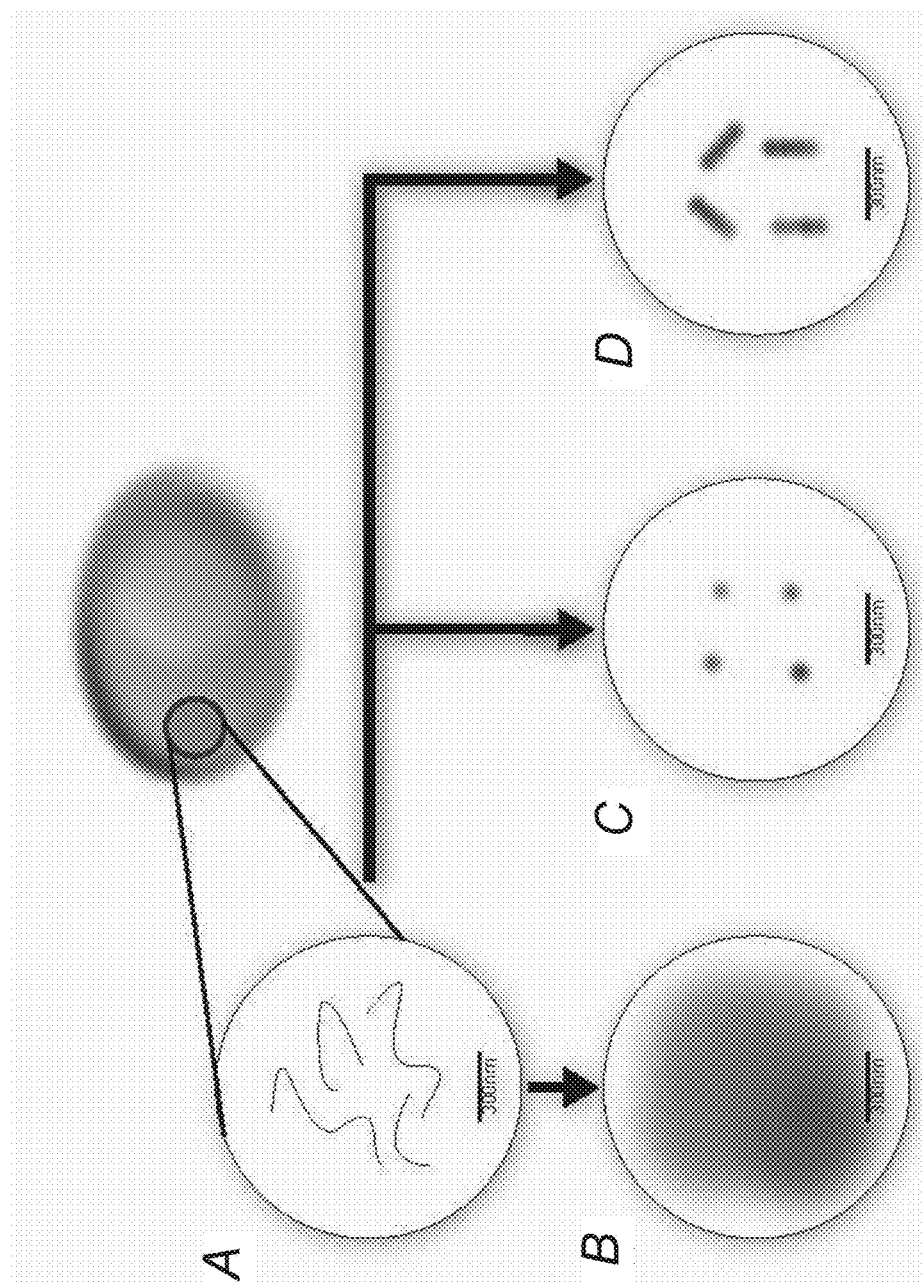
FIGS. 1A-1G depict, in accordance with an embodiment of the invention, that super-resolution and combinatorial molecular labeling allows high-throughput multiplex detection of molecular species in single cells. A-B) Molecular species in cells are difficult to resolve by conventional microscopy due to the diffraction limit of 300 nm. C) Super-resolution microscopy allows spatial resolution of individual molecules. D) The different species of molecules can be uniquely identified by a super-resolution barcode imparted by molecular labeling. SRM resolution of $(10 \text{ nm})^3$ allows a typical cell of $(10 \text{ um})^3$ to be decomposed into $10^9$ pixels, which is more than sufficient to accommodate the 106 copies of transcripts in a typical transcriptome. mRNA can be combinatorially labeled by FISH probes. A transcriptome of $10^4$ distinct mRNA species can be covered by a 6-position barcode with 6 fluorophores. E) Transcriptional profiling in single cells by super-resolution barcoding. Single molecules of mRNA (grey) can be visualized as dots in the cell by FISH. Each species of mRNA is barcoded by a set of labeled sequence-specific oligo probes. The copy number of each species of mRNA can be quantified by counting the number of occurrences of each barcode in the cell. A transcriptome of $10^4$ distinct mRNA species can be covered by a 6-position barcode with 6 fluorophores. F) and G) illustrate intensity coding and spatial coding, respectively.
Figure 1:
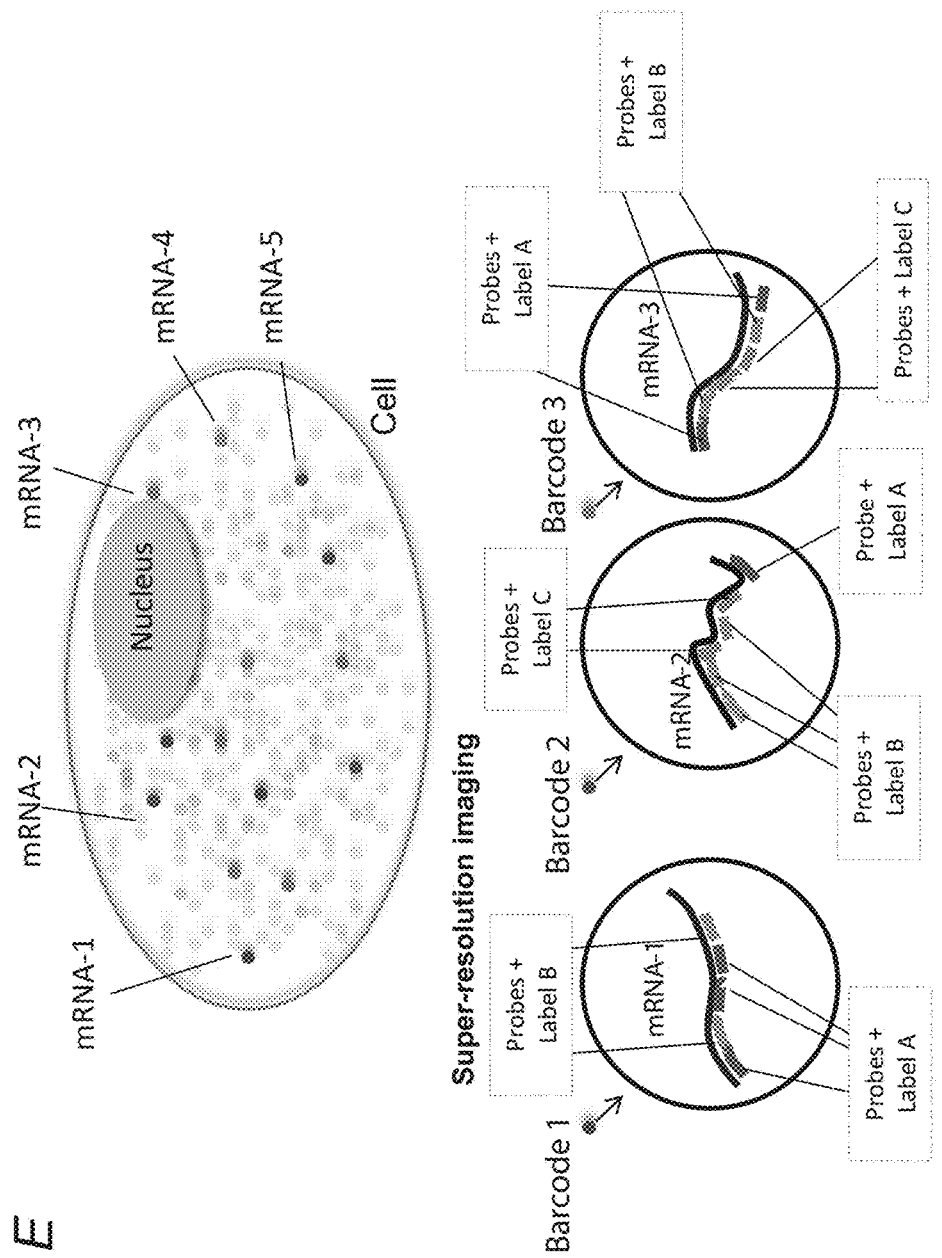
Figure 1:
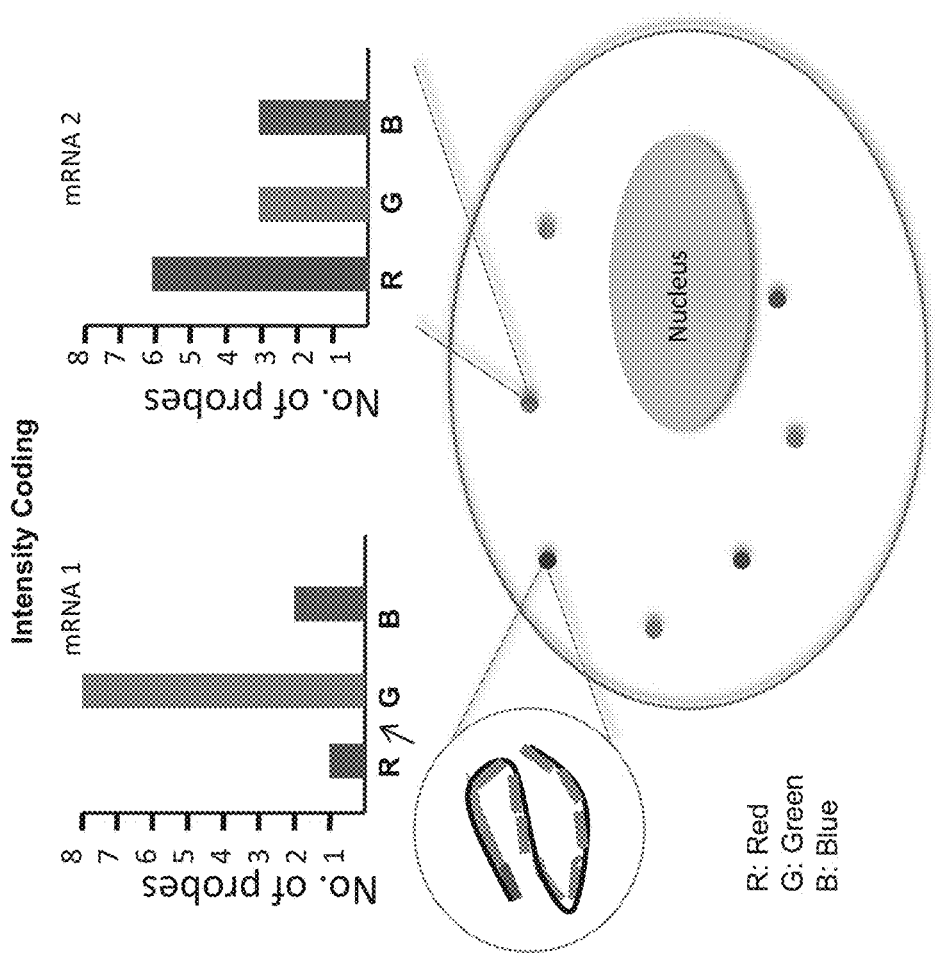
Figure 1:
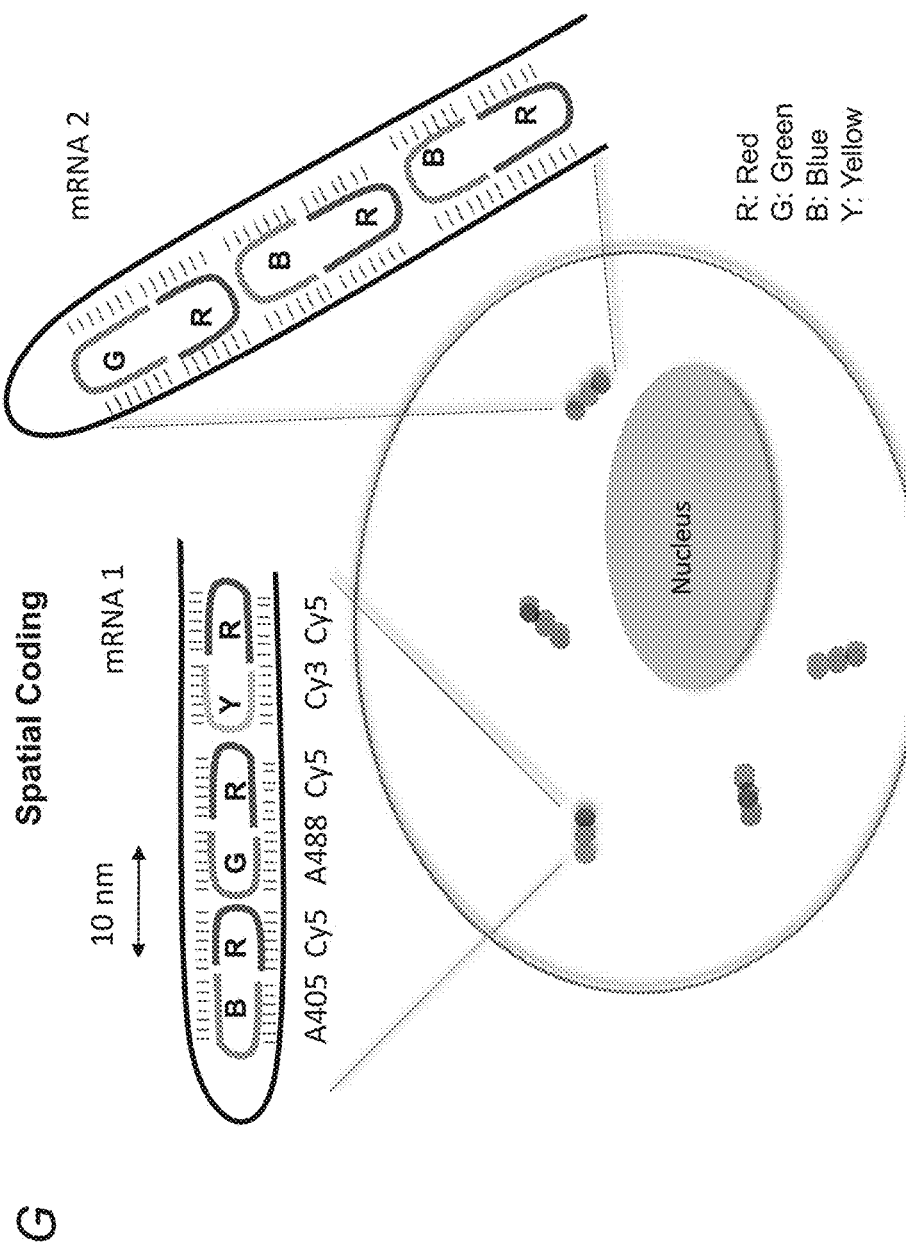

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, the term "an essentially intact or undisrupted cell" refers to a cell that is completely intact or largely conserved with respect to its macromolecular cellular content. For example, a cell within the meaning of this term can include a cell that is made at least partially permeable such that external buffers and/or reagents can be introduced into the cell. Such external reagents can include but are not limited to probes, labels, labeled probes, and/or combinations thereof.

As used herein, the term "cellular constituent" refers to any measurable biological variables that can be used in accordance with the present invention. Exemplary cellular constituents include but are not limited to any large biomolecules such as a DNA molecule or a fragment thereof, an RNA molecule or a fragment thereof, an mRNA molecule or a fragment thereof, a protein molecule or a fragment thereof, an mRNA complex or a section thereof, a protein complex or a section thereof, an organelle or a section thereof, or combinations thereof. Exemplary properties of cellular constituents include but are not limited to abundance level, location within a cell, abundance level or location with respect to other cellular constituents, relation to other cellular constituents, etc.

As used herein, the term "indicia" or "indicium" refers to any method, composition or system that can be associated with one or more cellular constituents to characterize at least one property of a cellular constituent at issue. As used herein, the term "molecular barcode" or "barcode" is used interchangeably with the term "indicium" or "indicia." The process of creating the indicia or barcode can be referred to as a barcoding process.

As used herein, the term "probe" refers to any composition that can be specifically associated with a target cellular constituent within a cell. A probe can be a small molecular or a large molecule. Exemplary probes include but are not limited to nucleic acids such as oligos, peptides, proteins (such as antibodies), or hybrids thereof.

As used herein, the term "label" refers to any composition that can be used to generate the signals that constitute an indicium. The signals generated by a label can be of any form that can be resolved subsequently to constitute the indicium. Preferably, the signal is a light within the visible range. In some embodiments, the signal is a light not in the visible range. In some embodiments, the signal is a radio signal, an X-ray signal, or an electro-magnetic signal. However, it will be understood by one of skill in the art that equipment and devices are available for recording and monitoring light of virtually any wavelength.

As used herein, the term "biological state" is broadly defined to refer to a state, a characteristic, or a property that is associated with a cellular constituent. For example, it can be the number of copies of mRNA transcripts associated with a particular gene and the locations of these transcripts within a cell. It can also be the identity and location of other cellular constituents that interact or bind to the target cellular constituents. Exemplary biological states include but are not limited to sequence, size, abundance level, activity level, two-dimensional structure, three-dimensional structure, charged state, surface accessibility, location within the cellular context, binding affinity and specificity to another cellular constituent, or a combination thereof.

Two sets of orthogonal systems biology approaches, large scale and small scale techniques, have traditionally been undertaken to elucidate the cellular interactions and biochemical networks. The large scale systems approaches, exemplified by microarrays and sequencing techniques, can profile comprehensively the transcriptional and the genomic state of a population of cells. On the other hand, the small scale systems approaches, for example, those using fluorescence microscopy techniques, can examine key genetic and regulatory interactions in individual cells while preserving the spatial context of the interactions.

The present invention combines the advantages of both approaches to bring the power of genomics into single cells. In one aspect, the methods and systems described herein provide unprecedented resolution in molecular interactions occurring in biological networks. In one aspect, the methods and systems described herein provide important clinical tools in identifying molecular signatures of disease. In another aspect, the methods and systems described herein can revolutionize the day-to-day experimental routines in the field of biological sciences, including but not limited to cell biology, molecular biology, biochemistry, biophysics and chemistry.

One of skill in the art would understand that most of the methods and systems described herein are applicable to all types of cells, including but not limited to bacteria, archaea, protists, fungi, plant, and animal cells, especially mammalian cells, mouse cells, human cells. Exemplary human cells include but are not limited to cancer cells, blood cells, lymphocytes, erythrocytes, white blood cells, epithelial cells, pituitary cells, gut and respiratory tract cells, various gland cells (e.g., thyroid, parathyroid, or adrenal glands), muscle cells, ciliated cells, embryonic cells, sensory transducer cells, various neuron cells, glial cells, lens cells, kidney cells, pigment cells, pancreatic cells, combinations thereof, etc.

Molecular Barcode

In one aspect, the power of genomics is brought into single cells via the creation of molecular barcodes or indicia, where barcodes or indicia are associated with specific cellular constituents.

Taking the high-throughput approach into a single cell may enable powerful exploration in many biological systems. However, multiplex detection of molecular species in single cells faces several fundamental challenges. First, individual cells need to be isolated. Then, molecules within those cells need to be separated, identified and quantified. Optical microscopy circumvents the need to isolate individual cells, but limits molecular discrimination, as molecules cannot be resolved beyond the diffraction limit (~300 nm). Referring to FIGS. 1A-1D, super-resolution technologies, such as super-resolution microscopy (SRM), bypasses the diffraction limit and allows the location of individual molecules to be determined accurately within 10-20 nm. This implies that under a super-resolution microscope with a 10 $nm^3$ resolution, a typical cell of 10 $um^3$ is composed of $10^9$ pixels. In comparison, there are only $10^6$ transcripts present in most cells. Thus, distinct molecules can be spatially resolved natively within the cell under SRM. Then, their identities can be uniquely addressed by combinatorial barcode labeling that is resolvable in super-resolution imaging (FIG. 1D). A 6 color 6 position barcode (66/2=23,328) is sufficient to uniquely code for each transcript in a mammalian transcriptome. In this fashion, SRM and combinatorial molecular labeling provide a general strategy to quantify molecular species on a genomic scale with single molecule precision in single cells.

The present methods and systems of molecular barcoding are used to illustratively detect multiple mRNA species in single *Saccharomyces cerevisiae* cells (Table 1).

As described above, a molecular barcode is broadly defined as a form of indicia that can be used to determine the identity or any other characteristics and/or properties of a cellular constituent in a cell. The methods and systems described herein can be used for research, diagnostic, prognostic or any other purposes. The cell can be a prokaryotic cell or a eukaryotic cell. For example, barcoding can be done in simple model organisms such as *E. coli* or yeast to monitor and study processes that include but are not limited to transcription, translation, protein folding, and protein-trafficking. Alternatively, methods and systems of barcoding can be used in more advanced organisms such as animal and human cells, for example, to determine a complicated structure of molecular complexes, to dissect a signaling pathway, to characterize alternative splicing events, or to monitor and quantify changes within the cells.

In some embodiments, a molecular barcode or indicium comprises a visual component, for example, in the form of a combination of different visible colors affixed to labels that are in turn affiliated with probes bound to one or more target cellular constituents in a cell. In some embodiments, the color type and frequency of these labeled probes are used to create a molecular barcode. In some embodiments, the color type, frequency and position of these labeled probes are used to create a molecular barcode.

Referring to FIG. 1E, a schematic representation of a single cell is shown with several labeled mRNA transcripts, e.g., mRNA-1 through mRNA-5. Each transcript is observed as being associated with a different indicium, when being subjected to super resolution imaging. For example, mRNA-1 appears purple; mRNA-2 appears green; and mRNA-3 appears orange. Here, each mRNA transcript is associated with a unique molecular barcode. The present invention enables simultaneous counting of multiple mRNA species with single molecule sensitivity in a single cell. Single molecules of mRNA (grey) can be visualized as dots in the cell. Each species of mRNA is barcoded by a unique set of labeled sequence specific oligo probes; example shown in color. The barcode can be resolved by STORM with a resolution of 5 nm. The copy number of each species of mRNA can be quantified by counting the number of occurrences of each barcode in the cell. A transcriptome of $10^4$ distinct mRNA species can be entirely covered by a 6-position barcode with 6 STORM dye colors.

Exemplary barcodes associated with transcripts mRNA-1, mRNA-2 and mRNA-3 are described further to illustrate the concept of molecular barcoding. In particular, barcode 1, which corresponds to mRNA-1 transcript, comprises five oligo nucleotide probes that each bind to a specific segment of the mRNA-1 transcript, including three probes with label A and two probes with label B. In this example, label A is red and label B is blue. The combined effect of three blue labels and two copies of red label is depicted as purple-like color and revealed by super resolution imaging to correspond to an arrangement of Red-Blue-Red-Red-Blue. In a different example, one probe with red label A, three probes with blue label B and two probes with green label C constitute barcode 2, which is used to represent mRNA-2. Barcode-2 is read under super resolution imaging to correspond to an arrangement of Blue-Blue-Green-Blue-Green-Red. In still another example, Barcode-3 is read under super resolution imaging to correspond to an arrangement of Red-Blue-Green-Green-Blue-Red.

As illustrated above, the types of signals (e.g., color) associated with each probe, the frequency and arrangement of these labeled probes can all be used to define a molecular barcode. Although no obvious gaps are present in the exemplary barcodes in FIG. 1, one of skill in the art would understand that absence of any signal (e.g., color) in parts of a cellular constituent can also be used to define a molecular barcode.

In some embodiments, in addition to the more or less linear order arrangements described above, more complex arrangements of the colored probes can also be used to define a molecular barcode associated with a particular cellular constituent. Exemplary non-linear arrangements include, for example, two-dimensional grids, maps, or three-dimensional lattices.

In some embodiments, for a less linear cellular constituent such as a protein, more complex spatial arrangements are needed to create the corresponding molecular barcode. For example, labeled antibodies targeting surface epitopes can be used to create one or more maps that uniquely identify the protein at issue. One of skill in the art would understand that a molecular barcode for a protein relies on knowledge of the structure of the protein at issues, the distribution of surface epitopes, as well as the availability of antibodies targeting such surface epitopes.

In some embodiments, small synthetic antibodies are used as probes when targeting one or more proteins. Synthetic antibody libraries have proven immensely useful for the de novo isolation of antibodies without the need for animal immunization. Focused libraries designed to recognize particular classes of ligands, such as haptens or proteins, have been employed to facilitate the selection of high affinity antibodies. Focused libraries are built using V regions encoding combinations of canonical structures that resemble the structural features of antibodies that bind the desired class of ligands and sequence diversity is introduced at residues typically involved in recognition. Synthetic antibodies are generated and experimentally validated with different scFv libraries that efficiently generate binders to peptides, a class of molecules that has proven to be a difficult target for antibody generation. Diversity was introduced in the $V_H$ using the profile of amino acids found at positions that frequently contact peptide antigens. Both libraries yielded binders to two model peptides, angiotensin and neuropeptide Y, following screening by solution phage panning. In particular, mouse libraries yielded antibodies with high affinities (e.g., below 20 nM) to both targets even though only the $V_H$ had been subjected to diversification.

In some embodiments, nucleic acids capable of binding to specific labels are attached to the natural or synthetic antibodies to generate the signals that ultimately create the molecular barcodes and/or indicia. In some embodiments, one or more secondary antibodies are used to generate the signals.

In some embodiments, synthetically evolved small peptides are used as "synthetic antibodies." The peptides have nanomolar affinity to target proteins and can be around 10 amino acids or longer; around 12 amino acids or longer; around 15 amino acids or longer; around 18 amino acids or longer; around 20 amino acids or longer; around 22 amino acids or longer; around 25 amino acids or longer; around 30 amino acids or longer; around 35 amino acids or longer; around 40 amino acids or longer; around 50 amino acids or longer; around 60 amino acids or longer; around 80 amino acids or longer; around 100 amino acids or longer; around 120 amino acids or longer; around 150 amino acids or longer; around 180 amino acids or longer; around 200 amino acids or longer; around 250 amino acids or longer; around 300 amino acids or longer around 400 amino acids or longer; or around 500 amino acids or longer.

More details on synthetic antibodies applicable to the present methods and systems can be found, for example, in Cobaugh et al., 2008, "Synthetic Antibody Libraries Focused Towards Peptide Ligands," *J Mol Biol.* 378(3): 622-633; Benhar I. 2007, "Design of synthetic antibody libraries," *Expert Opin Biol Ther.* 7(5):763-779; Nahary and Benhar, 2009, "Design of a human synthetic combinatorial library of single-chain antibodies," *Methods Mol Biol.* 525: 61-80; Bostrom and Fuh, 2009, "Design and construction of synthetic phage-displayed Fab libraries," *Methods Mol Biol.* 562:17-35; Fellouse et al., 2004, "Synthetic antibodies from a four-amino-acid code: A dominant role for tyrosine in antigen recognition," *Proc. Natl. Acad. Sci. U.S.A.* 101(34): 12467-12472; Agnew et al., 2009, "Iterative in situ click chemistry creates antibody-like protein-capture agents," *Angew Chem Int Ed Engl.* 48(27):4944-4948; Rohde et al., 2006, "A non-oxidative approach toward chemically and electrochemically functionalizing Si(111)," *J Am Chem Soc.* 128(29):9518-9525; each of which (including Supplemental Material) is hereby incorporated by reference herein in its entirety.

In some embodiments, aptamers can be used as probes to bind to cellular constituents, especially proteins. Aptamers are oligonucleic acid or peptide molecules that bind to a specific target molecule. Aptamers are usually created by selecting them from a large random sequence pool, but natural aptamers also exist in riboswitches. More specifically, aptamers can be classified as: DNA or RNA aptamers, which comprise (usually short) strands of oligonucleotides and peptide aptamers, which comprise a short variable peptide domain, attached at both ends to a protein scaffold.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range).

The variable loop length is typically composed of ten to twenty amino acids, and the scaffold may be any protein which has good solubility and compacity properties. Currently, the bacterial protein Thioredoxin-A is the most used scaffold protein, the variable loop being inserted within the reducing active site, which is a -Cys-Gly-Pro-Cys-loop in the wild protein, the two Cysteines lateral chains being able to form a disulfide bridge. Peptide aptamer selection can be made using different systems, but the most used is currently the yeast two-hybrid system. Selection of Ligand Regulated Peptide Aptamers (LiRPAs) has been demonstrated. By displaying 7 amino acid peptides from a novel scaffold protein based on the trimeric FKBP-rapamycin-FRB structure, interaction between the randomized peptide and target molecule can be controlled by the small molecule Rapamycin or non-immunosuppressive analogs.

In some embodiments, AptaBiD or Aptamer-Facilitated Biomarker Discovery is adopted for probe design. AptaBiD is based on multi-round generation of an aptamer or a pool of aptamers for differential molecular targets on the cells which facilitates exponential detection of biomarkers. It involves three major stages: (i) differential multi-round selection of aptamers for biomarker of target cells; (ii) aptamer-based isolation of biomarkers from target cells; and (iii) mass spectrometry identification of biomarkers. The important feature of the AptaBiD technology is that it produces synthetic affinity probes (aptamers) simultaneously with biomarker discovery. In AptaBiD, aptamers are developed for cell surface biomarkers in their native state and conformation. In addition to facilitating biomarker identification, such aptamers can be directly used for cell isolation, cell visualization, and tracking cells in vivo. They can also be used to modulate activities of cell receptors and deliver different agents (e.g., siRNA and drugs) into the cells.

In some embodiments, the aptamer probes themselves comprise labels that can generate signals that create the molecular barcodes or indicia. In some embodiments, secondary or even tertiary labels are used to generate signals that create the molecular barcodes or indicia.

Additional information on aptamer can be found, for example, in Ellington, et al., 1990, "In vitro selection of RNA molecules that bind specific ligands," Nature 346 (6287): 818-822; Bock, et al., 1992, "Selection of single-stranded DNA molecules that bind and inhibit human thrombin," Nature 355 (6360): 564-566; Hoppe-Seyler, et al., 2000, "Peptide aptamers: powerful new tools for molecular medicine," J Mol Med. 78 (8): 426-430; Carothers, et al., 2004, "Informational complexity and functional activity of RNA structures," J Am Chem Soc. 126 (16): 5130-5137; Cohen et al., 1998, "An artificial cell-cycle inhibitor isolated from a combinatorial library," Proc Natl Acad Sci USA. 95 (24): 14272-14277; Binkowski et al., 2005, "Ligand-regulated peptides: a general approach for modulating protein-peptide interactions with small molecules," Chem Biol. 12(7):847-855; Sullenger et al., 2002, "Emerging clinical applications of RNA," Nature 418 (6894): 252-258; Ng E W et al., 2006, "Pegaptanib, a targeted anti-VEGF aptamer for ocular vascular disease," Nat Rev Drug Discov 5 (2): 123-132; Drabovich et al., 2006, "Selection of smart aptamers by methods of kinetic capillary electrophoresis," Anal Chem. 78 (9): 3171-3178; Cho et al., 2009, "Applications of Aptamers as Sensors," Annual Review of Analytical Chemistry 2(1): 241-264; each of which (including Supplemental Material) is hereby incorporated by reference herein in its entirety.

The complexity of a particular barcode or a particular set of barcodes is determined by the ultimate purpose for which the barcodes are intended. For example, if the barcodes are used for profiling of large number of cellular constituents, the barcodes will be more sophisticated. For example, there will be more colors within each respective barcodes. The barcodes will comprise larger number of labeled probes. In addition, there will be more variations in linear frequencies and/or spatial arrangement of the labeled probes with respect to each barcode for large scale profiling type analysis. Alternatively, if the barcodes are intended for quantifying one or more particular cellular constituents or analyzing the interactions between specific cellular constituents, care will be taken to ensure accuracy by using redundant probes and multiplicity in barcoding. For example, probes bound to the same or overlapping region of a particular mRNA transcript can be tagged with different types of labels to provide redundancy data to improve accuracy and precision.

In some embodiments, the same cellular constituent can be represented by multiple barcodes. In some embodiments, only selected regions of a cellular constituent is used in creating a barcode. In some embodiments, the entire cellular constituent is used in creating a barcode.

In some embodiments, multiple probes carrying the same type of label are used in creating a barcode/indicium. This design results in differences in intensity of signals observed for different types of signals. FIG. 1F illustrates the concept of intensity barcoding. For example, the molecular barcode of mRNA1 comprises 1 probe associated with a label emitting a red (R) signal; 8 probes associated with a label emitting a green (G) signal; and 2 probes associated with a label emitting a blue (B) signal. The molecular barcode of mRNA2 comprises 6 probe associated with a label emitting a red (R) signal; 3 probes associated with a label emitting a green (G) signal; and 3 probes associated with a label emitting a blue (B) signal. In these embodiments, the intensity of different types of signals (such as light in different color) is observed separately, for example, by different color channel. In some embodiments, redundant coding is needed to correct for hybridization efficiencies.

In some embodiments, probes are designed to stabilize the target cellular constituents, thus increasing the persistence length and stiffening the probe-target cellular constituent complex. The strategy of "spatial barcoding" is depicted in FIG. 1G, and in several additional examples described herein. For example, mRNA1 and mRNA2 are folded into two closely linked duplexes upon binding of the probes. This approach will preserve high coding efficiency and will also allow two dyes in functional STORM dye unit to be brought into close proximity with each other through neighboring oligo probes. This will not only simplify synthesis, but also improve specificity as the only STORM capable probes are the pairs assembled correctly in the stapled structure, reducing background. Alternatively, functionalizing dyes are directly paired on oligo probes, as will be described hereinbelow.

One of skill in the art would understand that, although described in connection with mRNA transcripts, the strategies of intensity barcoding and spatial barcoding are applicable to other cellular constituents.

Additional details on probe design and labeling probes can be found herein below.

Creating Molecular Barcodes/Indicia

As described above, an important aspect of creating a molecular barcode is the selection and creation of the probes that specifically recognize a target cellular constituent. As illustrated above, when the target cellular constituent is an mRNA transcript, the probes that are used to recognize and bind to the mRNA transcript are oligonucleotides, or "oligos." In some embodiments, the oligo probes are 10-mers or longer. In some embodiments, the oligo probes are 15-mers or longer. In some embodiments, the oligos are 20-mers or longer; 25-mers or longer; 30-mers or longer; 40-mers or longer; 50-mers or longer; 70-mers or longer; 100-mers or longer; 150-mers or longer; 200-mers or longer; 250-mers or longer; 300-mers or longer; 500-mers or longer; or 1,000-mers or longer.

In some embodiments, the oligo probes are designed by using complementary sequences to randomly selected sequences or segments of sequences in a target cellular constituent. In some embodiments, the target cellular constituent is an mRNA transcript. In some embodiments, the target cellular constituent is an mRNA isoform.

In some embodiments, the oligo probes are designed by deliberately selecting sequences or segments of sequences that bind to a target cellular constituent with known or predicted binding affinity. This is called "intelligent probe design," where structure, sequence and biochemical data are all considered to create probes that will likely have better binding properties to a target cellular constituent. In particular, the preferred regions in a target cellular constituent are either identified experimentally or predicted by algorithms based on experimental data or computation data. For example, computed binding energy and/or theoretical melting temperature can be used as selection criteria in intelligent probe design. In certain embodiments, the cellular constituent is an mRNA transcript. In some embodiments, the cellular constituent is an mRNA isoform. In some embodiments, the mRNA is associated with a gene involved in neural patterning or tumorigenesis.

Tools are available for automated designs of probes that will have either actual or predicted optimal binding properties to the target cellular constituents. For example, the Designer program is routinely used for designing probes that bind to a particular target RNA sequence as part of the established single molecule RNA Fluorescent in-situ hybridization technology (FISH), which was developed at the University of Medicine and Dentistry of New Jersey (UMDNJ). For the Designer program, the open reading frame (ORF) of the gene of interest is typically used as input. This approach is used to exclude the more repetitive regions and low complexity sequence contained in Un-translated Regions (UTRs). Probes are designed to minimize deviations from the specified target GC percentage. The program will output the maximum number of probes possible up to the number specified. Sequence input is stripped of all non-sequence characters. A user can specify parameters such as the number of probes, target GC content, length of oligonucleotide and spacing length. Most success has been achieved with target GC contents of 45%. Typically, oligos are designed as 20 nucleotides in length and are spaced a minimum of two nucleotides apart.

To ensure accuracy, three major design considerations to target coding sequences of gene transcripts are used 1) mRNA length, 2) repeat sequences and 3) sequences of low complexity (such as GC content). As for length, the number of probes that can be accommodated for robust detection is primarily sequence dependent. Naturally longer RNA transcripts would require more probes or longer probes to ensure accuracy. Repetitive elements and low complexity sequences must be screened in advance and manually removed, further restricting the sequence space available for design. For this reason, certain genes such as the keratins may present unusual challenges. The optimal target has an overall GC content of 40-50%, although mRNAs with higher GC content may yield good results by using more stringent washing conditions.

The Stellaris RNA FISH method is applicable to a variety of biological specimens, including but not limited to bacteria, yeast, mammalian cells, *C. elegans* embryos and L1-L2 larvae, *Drosophila melanogaster* wing imaginal discs, and primary rat hippocampal neurons.

Additional description of single molecule FISH can be found in, for example, Raj A., et al., 2008, "Imaging individual mRNA molecules using multiple singly labeled probes," *Nature Methods* 5(10): 877-879; Femino A., et al., 1998, "Visualization of single RNA transcripts in situ," *Science* 280: 585-590; Vargas D., et al., 2005, "Mechanism of mRNA transport in the nucleus," *Proc. Natl. Acad. Sci. of USA* 102: 17008-17013; Raj A., et al., 2006, "Stochastic mRNA synthesis in mammalian cells," *PLoS Biology* 4(10): e309; Maamar H., et al., 2007, "Noise in gene expression determines cell fate in *B. subtilis*," *Science,* 317: 526-529; and Raj A., et al., 2010 "Variability in gene expression underlies incomplete penetrance," *Nature* 463:913; each of which (including any Supplemental Material) is hereby incorporated by reference herein in its entirety.

The rationale of intelligent probe design also applies to probes that are not nucleic acids, such as proteins. Given the three-dimensional nature of protein molecules, intelligent designs of antibody probes that would bind to a target cellular constituent can be more challenging. For example, protein structures and known epitope data or prediction algorithms will be considered to identify accessible surface epitopes that will likely combine to create an indicium or molecular barcode that is associated with the target cellular constituent and can be used to identify it within a cellular environment or to determine properties associated with the target cellular constituent, such as location within the cell and possible binding partners.

In some embodiments, protein indicia can be identified by in vitro analysis. For example, purified protein samples can be conjugated with one or more labeled antibodies. The locations of these antibodies can then be determined by electron microscopy, X-ray diffraction, or combined methods. Electron microscopes (EM) have a greater resolving power than a light-powered optical microscope, because electrons have wavelengths about 100,000 times shorter than visible light (photons), and can achieve better than 0.2 nm resolution and magnifications of up to 2,000,000×. The pre-determined indicia can then be used as standards (or positive controls) to assist the identification of molecular indicia or barcodes of proteins in a cell using the super resolution technologies of the present invention.

In some embodiments, the present methods and systems can be used to carry out whole cell labeling of nucleic acids and proteins. Previously, over 1,000 genes were each tagged individually in different cells with fluorescent labels, and then protein and mRNA copies in individual cells were counted using a high-throughput system. In another example, over 7,000 genes were classified by applying FISH to one gene one at a time in the Berkeley fly genome project. See, for example, insitu<dot>fruitfly<dot>org; Taniguchi Y., et al., 2010, "Quantifying *E. coli* proteome and transcriptome with single-molecule sensitivity in single cells," *Science* 329:533-538; Tomancak et al., 2002, "Systematic determination of patterns of gene expression during *Drosophila* embryogenesis," *Genome Biol.* 3(12):1-14; Tomancak et al., 2007, "Global analysis of patterns of gene expression during *Drosophila* embryogenesis," Genome Biol. 8(7): R145; each of which (including any Supplemental Material) is hereby incorporated by reference herein in its entirety. By using different molecular barcodes, the present systems and methods all allow one to label multiple cellular constituents in the same cell.

It will be understood by one of skill in the art that indicia corresponding to longer, larger or more complex cellular constituents require more sophisticated combination of probes. For example, probes of longer oligonucleotides or more probes are needed to recognize and distinguish mRNA transcripts bearing similar sequences. Similarly, distinguishing proteins bearing similar structural or functional domains will also require more complex indicia.

It will be understood by one of skill in the art that the current methods and systems can be applied to a combination of cellular constituents. For example, DNA, RNA and protein can be labeled and analyzed in one single experiment.

One of skill in the art would also understand that length or size of probes will vary, depending on the target cellular constituents and purposes of the analysis.

Labels are associated with the specific probes to allow them to emit signals that will be used in subsequence super resolution analysis. Any labels suitable for generating such signals can be used in the present invention. In some embodiments, the signals are generated by fluorophores. Fluorescent labeling, e.g., the process of covalently attaching a fluorophore to a probe that binds to a cellular constituent (such as a protein or nucleic acid) is generally accomplished using a reactive derivative of the fluorophore that selectively binds to a functional group contained in the target molecule. In some embodiments, exemplary probes to which the labels are attached include but are not limited to antibodies, proteins, amino acids and peptides. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide.

Following a fluorescent labeling reaction, it is often necessary to remove any non-reacted fluorophore from the labeled target molecule. This is often accomplished by size exclusion chromatography, taking advantage of the size difference between fluorophore and labeled protein, nucleic acid, etc. Fluorophores may interact with the separation matrix and reduce the efficiency of separation. For this reason, specialized dye removal columns that account for the hydrophobic properties of fluorescent dyes are sometimes used. Reactive fluorescent dyes are available from many sources. They can be obtained with different reactive groups for attachment to various functional groups within the target molecule. They are also available in labeling kits that contain all the components to carry out a labeling reaction.

In some embodiments, labels of the present invention comprise one or more fluorescent dyes, including but not limited to fluorescein, rhodamine, Alexa Fluors, DyLight fluors, ATTO Dyes, or any analogs or derivatives thereof.

In some embodiments, labels of the present invention include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some embodiments, labels of the present invention include but are not limited to ATTO dyes; Acridine dyes (e.g., Acridine orange, Acridine yellow); Alexa Fluor; 7-Aminoactinomycin D; 8-Anilinonaphthalene-1-sulfonate; Auramine-rhodamine stain; Benzanthrone; 5,12-Bis(phenylethynyl)naphthacene; 9,10-Bis(phenylethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), Texas Red, TSQ, Umbelliferone, or Yellow fluorescent protein.

In some embodiments, labels of the present invention include but are not limited to the Alexa Fluor family of fluorescent dyes (Molecular Probes, Oregon). Alexa Fluor dyes are typically used as cell and tissue labels in fluorescence microscopy and cell biology. The excitation and emission spectra of the Alexa Fluor series cover the visible spectrum and extends into the infrared. The individual members of the family are numbered according roughly to their excitation maxima (in nm). Alexa Fluor dyes are synthesized through sulfonation of coumarin, rhodamine, xanthene (such as fluorescein), and cyanine dyes. Sulfonation makes Alexa Fluor dyes negatively charged and hydrophilic. Alexa Fluor dyes are generally more stable, brighter, and less pH-sensitive than common dyes (e.g. fluorescein, rhodamine) of comparable excitation and emission, and to some extent the newer cyanine series. However, they are also more expensive. Exemplary Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some embodiments, labels of the present invention comprise one or more members of the DyLight Fluor family of fluorescent dyes (Dyomics and Thermo Fisher Scientific). Exemplary DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some embodiments, when pairs of dyes are used (as described in greater detail herein below) the activator choices include Alexa 405, 488, 532 and 568, and the emitter choices include Cy5, Cy5.5, Cy7, and 7.5. Using these particular choices, because they can be mixed and matched to give functional dye pairs, there are 16 possible pairs (4×4) in all. In some embodiments, for RNA FISH, emitters used are Alexa 647 or Dynomics 632, Cy5.5, Cy7, and IR800CW. In some embodiments, for DNA FISH, they are Alexa 647, Cy5.5, Alexa 750 and Alexa 790.

In some embodiments, the same type of labels can be attached to different probes for different types of cellular constituents, including nucleic acids and proteins.

For example, in some embodiments, DNA or RNA probes are labeled with either Cy3 or Cy5 that has been synthesized to carry an N-hydroxysuccinimidyl ester (NHS-ester) reactive group. Since, NHS-esters react readily only with aliphatic amine groups, which nucleic acids lack, nucleotides have to be modified with aminoallyl groups. This can be done through incorporating aminoallyl-modified nucleotides during synthesis reactions. In some embodiments, a label is used in every 60 bases to avoid quenching effects.

For example, in some embodiments, protein probes (e.g., antibodies) are also labeled with either Cy3 or Cy5. For protein labeling, Cy3 and Cy5 dyes sometimes bear maleimide reactive groups instead. The maleimide functionality allows conjugation of the fluorescent dye to the sulfhydryl group of cysteine residues. Cysteines can be added and removed from the protein domain of interest via PCR mutagenesis. Cy5 is sensitive to the electronic environment in which it resides. Changes in the conformation of the protein to which the label is attached can produce an enhancement or quenching of the emission. The rate of this change can be measured to determine enzyme kinetic parameters. Cy3 and Cy5 are used in proteomics experiments so that samples from two sources can be mixed and run together thorough the separation process. This eliminates variations due to differing experimental conditions that are inevitable if the samples were run separately. These variations make it extremely difficult, if not impossible, to use computers to automate the acquisition of the data after the separation is complete. Importantly, using these dyes makes the automation trivial.

One of skill in the art would readily appreciate that choices for a label are determined based on a variety of factors, including, for example, size, types of signals generated, methods of attachment to or incorporation into a probe, properties of the cellular constituents, including their locations within the cell, properties of the cells, types of interactions being analyzed, and so forth.

Incorporating Labels into Probes

In some embodiments, labels such as fluorophores are attached to the probes as a secondary addition. In these embodiments, the probes are synthesized or formed prior to the addition of the labels. In some embodiments, labels such as fluorophores are attached to specific locale of the probes. For example, pre-synthesized probes (e.g., oligonucleotides or peptides) are mixed with fluorophores under predefined reaction conditions such that attachment of the fluorophores to the probes results.

In some embodiments, labels are embedded within the probes themselves. In these embodiments, one or more labels are incorporated into probes while they are being synthesized or formed. For example, a fluorophore can be embedded in an oligonucleotide probe during synthesis. In some embodiments, one or more labels (e.g., fluorophores) are attached to multiple identical probes (e.g., oligos with identical sequences).

In some embodiments, different labels (e.g., fluorophores) are attached to multiple identical probes (e.g., oligos with identical sequences). For example, multiple indicia can be created with minor variations in signal arrangement for the same cellular constituent. Such near-redundancy or near-duplicity is used to ensure accuracy of barcoding. In some embodiments, the same label (e.g., fluorophores emitting red light at the same wavelength) is attached to multiple identical probes (e.g., oligos with identical sequences).

In some embodiments, for example, when aptamers are used as probes, signal-emitting labels are added in a secondary or tertiary step. For example, aptamers that specifically bind to a protein are first synthesized. Complementary DNA oligos, which already have labels attached or embedded, are added later to allow binding to the DNA element in the aptamers. In such embodiments, signal-emitting labels are not directly associated with the probes, but through an intermediary composition—the DNA molecule in an aptamer. Similarly, intermediary binding partners of a peptide element or an RNA element of an aptamer can also be used to affixing labels that will emit the signals for the molecular barcodes or indicia.

As used herein, an intermediary composition is any molecule or structure to which a label can be attached or embedded to form the final molecular barcodes or indicia. Exemplary intermediary compositions include but are not limited to a DNA or derivatives thereof, an RNAs or derivatives thereof, DNA-RNA hybrids or derivatives thereof, a peptide or analogs thereof, In some embodiments, multiple intermediary compositions can be used to permit final attachment of labels that emit the signals for the molecular barcodes or indicia. For example, the number of intermediary composition used can be one, two, three, four, five, six, seven or more, or ten or more.

In some embodiments, when fluorophores are used as labels, a spare, optically resolvable subset of fluorophores is selectively activated by using photo-switchable fluorophores. For example, multicolor super resolution imaging can be done with a family of photo-switchable fluorescent probes, using Stochastic Optical Reconstruction Microscopy (STORM), as described and demonstrated in the experiments set forth in the "Examples" section herein. Some of the commonly used fluorophores, such as Cyanine dyes can undergo reversible photoswitching, where the fluorophore can be switched between a fluorescent state and a dark state upon exposure to light of different wavelengths. The rate of switching to the dark state depends on the concentration of the primary thiol in the solution and the solution pH in a manner quantitatively consistent with the formation of an encounter complex between the cyanine dye and ionized thiol prior to their conjugation. Mass spectrometry suggests that the photo-conversion product is a thiol-cyanine adduct in which covalent attachment of the thiol to the polymethine bridge disrupts the original conjugated $\pi$-electron system of the dye. In particular, Cy5 has demonstrated such "optical switching" properties: its fluorescence emission can be switched on and off using pulses of light. During each excitation, Cy5 emits thousands of photons before going dark. A brief pulse of ultraviolet light will then efficiently reactivate the molecule to its fluorescent state, and this process can be repeated for hundreds of cycles. The switchable fluorescence exhibited by Cy5 is a strongly nonlinear process, and this nonlinearity can be used to overcome the diffraction limit of resolution.

In some embodiments, a probe is associated with a photo-switchable "reporter" fluorophore (such as those described above) that can be cycled between fluorescent and dark states, and an "activator" that facilitates photo-activation of the reporter. In some embodiments, pairs of reporter-activator fluorophores are used as labels, as demonstrated in the "Examples" section. Combinatorial pairing of reporters and activators allows the creation of probes with many distinct colors. Iterative, color-specific activation of sparse subsets of these probes allows their localization with nanometer accuracy, enabling the construction of a super-resolution STORM image. Using this approach, multicolor imaging of DNA model samples and mammalian cells can be done with 20- to 30-nanometer resolution.

In some embodiments, pools of probes are use against multiple target cellular constituents using a tiered strategy (Table 1 and FIGS. 2A-2D), similar to that described in Huffman coding. For example, more strongly expressed genes are coded with least complex barcodes, while less strongly expressed genes are coded with more complex barcodes.

Additional details concerning photo-switchable fluorophores used as labels can be found herein in the "Examples" section. More details on switchable fluorophores can be found, for example, in Bates et al., 2007, "Multicolor Super-Resolution Imaging with Photo-Switchable Fluorescent Probes," *Science* 317(5845): 1749-1753 and Supplemental Online Material, and Dempsey et al., 2009, "Photoswitching Mechanism of Cyanine Dyes," *J. Am. Chem. Soc.*, 131(51): 18192-18193, each of which (including any Supplemental Material) is hereby incorporated by reference herein in its entirety.

Hybridization of Probes to Target Cellular Constituents

Labeled probes are subsequently introduced into the cell and hybridized to target cellular constituents. In general, in situ hybridization of yeast cells is almost identical to mammalian cells, except that the cell wall has to be removed by spheroplasting the yeast cells prior to hybridization. Additional details can be found, for example, in Long R M, et al., 1995, *RNA* (10): 1787-1794 and at singlemoleculefish<dot>com/protocols<dot>html, each of which (including any Supplemental Material) is hereby incorporated by reference herein in its entirety.

In some embodiments, a hybridization process comprises the steps of probe preparation, fixation, hybridization, washing, and mounting. In some embodiments, RNAse treatment and antibody detection are also included.

One of skill in the art would understand that hybridization conditions of the probes to target cellular constituents changes with respect to the specific purposes for which a barcoding method/system is used.

Resolving Barcodes or Indicia—De-coding the Barcodes

In some embodiments, signals from cellular constituents bearing multi-signal molecular barcodes are recorded at the same time. In some embodiments, signals from cellular constituents bearing multi-signal molecular barcodes are recorded at different times, one signal at a time. Data collected from multiple channels can be combined to produce one or more composite images. One of skill in the art would readily appreciate that cross-talking among labels can be reduced by modifying the probe design, types of label attached, use of equipment with better resolution, or by improving the methods or algorithms by which the data are processed.

In some embodiments, drifts in multichannel experiments are corrected by using fluorescent beads as fiducial markers. These beads can be localized to 1-2 nm using Gaussian fitting, and can be used accurately to correct for small changes in stage positions. In some embodiments, where multi-imaging channels are used, gold nanoparticles can be used to correct for chromatic aberrations. In some embodiments, some magnetic beads are used to correct drifting in multichannel experiments. Additional details on such technologies can be found, for example, in Shroff et al., 2007, "Dual-color super-resolution imaging of genetically expressed probes within individual adhesion complexes," *Proc. Natl. Acad. Sci. USA* 104(51):20308-20313 and Bates et al., 2007, "Multicolor Super-Resolution Imaging with Photo-Switchable Fluorescent Probes," *Science* 317(5845): 1749-1753, which (including any Supplemental Material) is incorporated by reference herein in its entirety.

In some embodiments, Cy5.5 or Cy7 based dyes are used to increase the available colors to at least 6. Incorporating Spiroamides can add additional colors to the palette, allowing drastically enhanced multiplex capabilities. Introduction of these dyes would require chromatic corrections on the STORM reconstructed images. In addition, two color repeat barcodes can be used, depending mainly on the photophysical properties of the Cy5 based STORM dyes. The relatively poor contrast ratio (1:200) of the Cy5 based dyes means that stronger than ideal activation power is needed to overcome the non-specific blinking rate of Cy5. This increases the frequency of multiple activation of fluorophores within the same diffraction limited volume, and generates spatial blurring in between the repeat coding position. Thus for the repeat barcode experiments, the activation power is tuned to be above the non-specific activation rate, but lower than the rate that would generate multiple activations within the same diffraction limited spot.

In some embodiments, only simple three-color barcodes are implemented where higher activation intensity and multiple switching events in one color do not distort the barcode image to avoid complications caused by the nonspecific blinking of dyes. In some embodiments, the axial dimensions of the fluorophores are resolved. The approach of using astigmatic or dumbbell shaped point-spread-function can improve the axial resolution to 50 nm, which can be helpful to resolve 2 barcoded mRNAs if they overlap in the xy but not z dimension. In some embodiments, interferometric PALM can be used to further resolve axial resolution, e.g., to 5 nm. The ultimate limiting factor in the multiplexing is the contrast ratio of Cy5 dyes. It limits the labeling density as no more than 100 Cy5 molecules can be in the same diffraction limited volume for super-resolution reconstruction and prevents the effective usage of the repeat barcodes.

In some embodiments, techniques are used to achieve z-resolution on super resolution scale, for example, on the nanometer scale. The z-resolution is generally defined as the optical thickness of the optical z-plane. Methods for improving z-resolution are known in the art and can be applied to the present methods and systems.

In some embodiments, as described hereinabove, a Huffman coding type of strategy is used to facilitate signal resolution based on known additional expression data.

In some embodiments, a cell sample is subject to 3D-sectioning to collection data that will be used to reconstruct the three-dimensional structure of the cell. The laser light section method is a 3D-procedure to measure object profiles in one sectional plane. The principle of the laser triangulation requires an orthogonal to the objects surface positioned detector area (e.g., CCD- or CMOS-matrix) to measure the lateral displacement or the deformation of a laser line projected in an angle (between 0 and 90 degrees) onto the objects surface. Laser light sectioning is the two-dimensional extension of the laser triangulation. With projecting the expanded laser line, an elevation profile of the object under test is obtained.

Methods for data processing, especially those for digital imaging data processing can be used in the present invention to improve or optimize the process for resolving barcode/indicium. Digital image processing is the only practical technology for classification, feature extraction, pattern recognition, projection, and multi-scale signal analysis, each of which aspect is applicable to dissolving molecular barcodes/indicia. Exemplary techniques or algorithms that are used in digital image processing include but are not limited to pixelization, linear filtering, principal components analysis, independent component analysis, hidden Markov models, anisotropic diffusion, partial differential equations, self-organizing maps, neural networks, and wavelets.

Indicia created by molecular barcoding are resolved or discerned by super resolution technologies. In some embodiments, super resolution technologies of the present invention include super resolution microscopy. In some embodiments, the super resolution technology has a resolution of about 100 nm or higher; about 80 nm or higher; about 60 nm or higher; about 50 nm or higher; about 40 nm or higher; about 30 nm or higher; about 25 nm or higher; about 20 nm or higher; about 15 nm or higher; about 10 nm or higher; about 8 nm or higher; about 6 nm or higher; about 5 nm or higher; about 4 nm or higher; about 3 nm or higher; about 2 nm or higher; about 1 nm or higher; about 0.5 nm or higher; about 0.2 nm or higher; about 0.1 nm or higher; about 0.05 nm or higher; or about 0.01 nm or higher.

One of skill in the art would understand that the specific characteristics (e.g., size) of the cellular constituents will determine the resolution at which a particular indicium will be resolved.

Super resolution techniques allow the capture of images with a higher resolution than the diffraction limit. They fall into two broad categories, "true" super resolution techniques, which capture information contained in evanescent waves, and "functional" super resolution techniques, which uses clever experimental techniques and known limitations on the matter being imaged to reconstruct a super resolution image. True sub-wavelength imaging techniques include those that utilize the Pendry Superlens and near-field scanning optical microscopy. Most techniques of importance in biological imaging fall into the functional category.

Exemplary super resolution technologies include but are not limited to $I^5M$ microscopy, 4Pi-microscopy, Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof. Descriptions of relevant techniques can be found in Chi, 2009 "Super-resolution microscopy: breaking the limits, Nature Methods 6(1):15-18; Blow 2008, "New ways to see a smaller world," Nature 456:825-828; Hell, et al., 2007, "Far-Field Optical Nanoscopy," Science 316: 1153; R. Heintzmann and G. Ficz, 2006, "Breaking the resolution limit in light microscopy," Briefings in Functional Genomics and Proteomics 5(4):289-301; Garini et al., 2005, "From micro to nano: recent advances in high-resolution microscopy," Current Opinion in Biotechnology 16:3-12; Bewersdorf et al., 2006, "Comparison of $I^5M$ and 4Pi-microscopy," 222(2):105-117; and Wells, 2004, "Man the Nanoscopes," JCB 164(3):337-340; each of which (including Supplemental Material) is hereby incorporated by reference herein in its entirety.

In some embodiments, electron microscopes (EM) are used to resolve an indicium. Electron microscopes have a greater resolving power than a light-powered optical microscope, because electrons have wavelengths about 100,000 times shorter than visible light (photons), and can achieve better than 0.2 nm resolution and magnifications of up to 2,000,000 times.

Exemplary Embodiments of the Methods and Systems

In some embodiments, a plurality of cellular constituents is barcoded by methods and systems of the present invention. For example, molecular barcoding can be applied to one cellular constituent; two or more cellular constituents; three or more cellular constituents; four or more cellular constituents; five or more cellular constituents; six or more cellular constituents; eight or more cellular constituents; ten or more cellular constituents; 15 or more cellular constituents; 20 or more cellular constituents; 30 or more cellular constituents; 50 or more cellular constituents; 80 or more cellular constituents; 100 or more cellular constituents; 150 or more cellular constituents; 200 or more cellular constituents; 300 or more cellular constituents; 500 or more cellular constituents; 1,000 or more cellular constituents; 1,500 or more cellular constituents; or 2,000 or more cellular constituents.

In one aspect, the present invention is used to measure a biological state of a cell, for example, its transcriptional state. The transcriptional state of a cell includes the identities and abundances of the constituent RNA species, especially mRNAs, in the cell under a given set of conditions. For example, a fraction of the constituent RNA species in the cell can be measured for genetic profiling.

In some embodiments, only one type of cellular constituent is analyzed, for example, mRNA transcript. In some embodiments, one or more mRNA isoforms are analyzed in order to characterize alternative splicing events. One of skill in the art would readily appreciate that one or more mRNA isoforms can be analyzed using any of the labeling schemes described herein. In some embodiments, the labeling scheme involves labeling one or more introns and one or more exons, as depicted in Example 10, and described in greater detail herein below.

In some embodiments, two or more types of cellular constituents are analyzed. For example, interactions between RNAs and proteins can be analyzed.

In some embodiments, time resolved analysis can be carried out. For example, sample cells can be synchronized by chemical arrest or starvation. Thereafter, cells will be taken at different time points and are sequentially subjected to analysis by molecular barcoding followed by super resolution de-coding. By doing so, a time course of the desired reaction or process can be constructed.

In some embodiments, the present methods and systems can be used to conduct biochemical assay in a single cell setting. For example, the present methods and systems can be used to study interactions between any cellular constituents, including protein-protein interactions, protein-nucleic acid interaction, and others. In some embodiments, time-resolved biochemical assays can be performed using the present methods and systems.

Additional Embodiments

Transcription Profiling in Single Cells.

In some embodiments, a transcriptional state of a cell is imaged by detecting and distinguishing individual mRNAs. Florescence In-Situ Hybridization (FISH) allows single mRNAs molecule in fixed cells to be labeled and imaged. This is accomplished by hybridizing the mRNA with a set of short oligonucleotide probes complementary to the mRNA sequence. Conventionally, these probes are labeled all with the same fluorophore to increase the contrast compared to non-specific bound probes in the cell. This allows individual mRNA to be visualized as a bright fluorescent dot in the cell. In such embodiments, the number of species that can be labeled simultaneously is determined by the availability of spectrally distinct fluorophores. Further, if the expression level of the targeted mRNA is high, then individual hybridized transcripts cannot be optically resolved from each other, preventing accurate quantitation of the copy number.

In some embodiments, different super-resolution fluorophores are attached within a set of oligo probes, such that as they hybridize against their target mRNA, a molecular barcode or indicium can be readout by super-resolution microscopy. The barcode can then serve to uniquely identify that particular transcript. Thus, by using different barcodes for different mRNA species, many mRNAs can be labeled simultaneously as illustrated in FIG. 1.

The systems and methods described herein have enormous capacity and can effectively barcode the entire human transcriptome with at least 6 distinct super-resolution fluorophores. The entire human transcriptome has about 20,000 genes and 6 distinct super-resolution fluorophores at 6 barcode positions render over 45,000 combinations ($6^6$=46656). In addition, with the giga-pixel volume of a single cell under super-resolution microscopy, individual mRNAs can be imaged and their barcode read out without concerns of overcrowding in the optical space. The expression level for each species of mRNAs can then be tallied by counting the abundance of the corresponding barcodes. This technique not only detects transcripts with single molecule sensitivity, therefore highly accurate in quantitation, but also preserves the intracellular and intercellular spatial context in which transcription occurs. These advantages make it especially applicable for investigations in heterogeneous cell populations, such as cell cultures, tissue sections, and embryos.

Mapping Chromosome Structures.

Chromosomal rearrangements have been implicated in many forms of cancer, and recent investigations revealed that chromosomes in eukaryotes are packed in a non-linear and complex fashion. Super-resolution barcoding can be applied to image the structure of chromosomes and determine their conformation in single cells. Conventional DNA-FISH can label only 4-5 distinct chromosomal locations limited by the number of distinct fluorophores. However, with the super-resolution barcoding technique, a large set of genomic loci can be labeled each with a distinct barcode and resolved by microscopy. Thus, the physical location of many genes can be mapped and serve as landmarks on the chromosomes, thereby allowing for detection of chromosomal translocations and other rearrangement events in cells. A physical image of the chromosomes in cells with the addresses of individual genes will allow for an unprecedented look at how the genome is compacted, compare organization in transcriptionally active versus repressed regions, and detect subtle changes in genomic structure in tumor cells.

Imaging Transcription Factor Binding in Single Cells.

In some embodiments, the methods and systems described herein are used to analyze transcription factor binding in single cells. Transcription factors (TFs) control genes in transcriptional networks through binding sites on the DNA and interactions with regulatory proteins. The distribution of positions and binding states of a particular TF on the chromosome determines the transcriptional program it is accessing in the cell. By fusing TFs with photo-switchable fluorescent protein or labeling with antibodies, the physical location of individual TFs can be determined with 10 nm resolution. The genomic location of the TF can then be assigned by overlaying those positions on top of the high resolution chromosome map developed from technique 2. Results from ChIP-seq experiments can be compared to determine the occupancy of each binding site and higher order structures at the promoters in single cells. In some embodiments, analysis by the present methods and systems focus specifically on Crz1, a TF in budding yeast that has been shown to pulse in its activity. In some embodiments, the fraction of Crz1 binding sites that are occupied during a pulse can be determined. In some embodiments, it can be determined whether occupancy of different binding sites is correlated depending on their physical proximity in the nucleus.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Experiments I

Example 1

Probe Design, Purification and Hybridization

Figure 9:
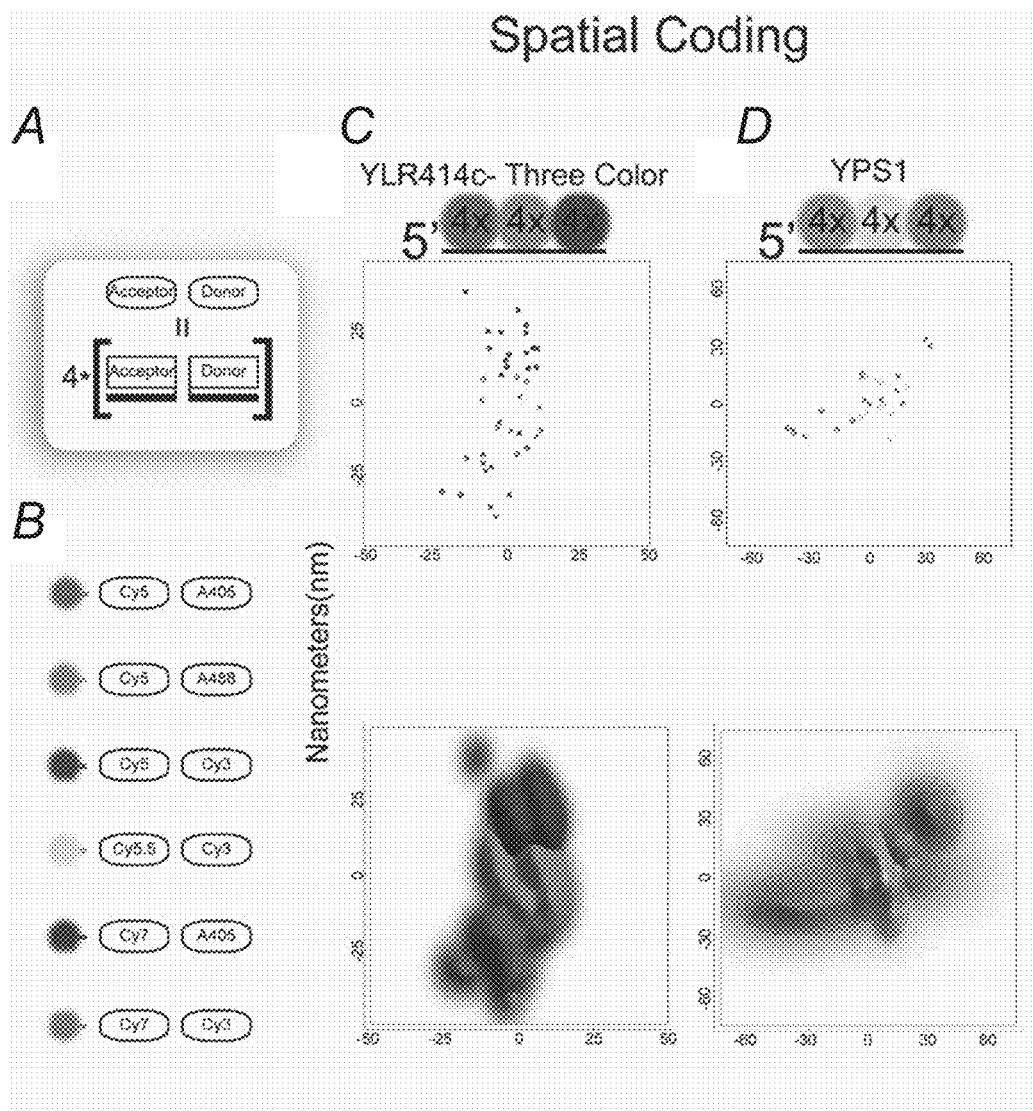
Figure 9:
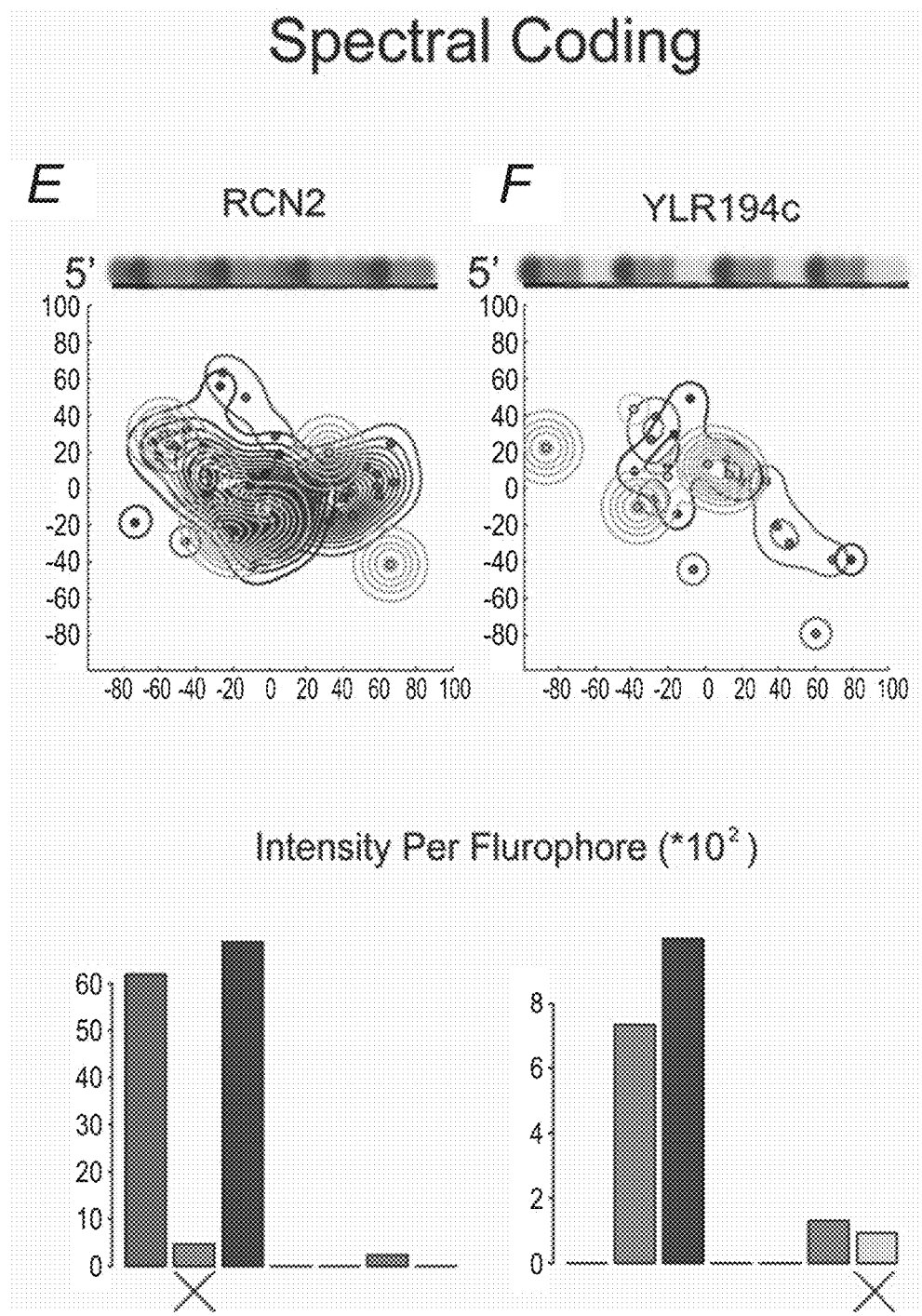

Probes (20mers) were designed to match melting temperature whenever possible, with the exception of STORM probes which were designed to have 2 base pair spacing between the probes to allow efficient reactivation of the STORM pair dyes (FIG. 9). Labeling and purification of the probes follows the protocol at the smFISH web site (www<dot>singlemoleculefish<dot>com). Yeast cells were grown in minimal media and fixed in log growth phase following the Singer lab protocols, with the minor addition of a 0.1% NaBH$_4$ treatment before ethanol permeabilization step. The NaBH$_4$ treatment significantly decreased the autofluorescence background of the fixed yeast cells. Cells were stored in an eppendorf tubes and aliquoted for hybridization experiments. Cells were hybridized with the probes overnight at room temperature in 20% Formamide and 10% dextran sulfate. After hybridization, cells were washed in Formamide and SSC solution 3 times and imaged.

Example 2

Imaging

Imaging of the hybridized cells is carried out on automated fluorescence microscopes. For FIONA, images were acquired on an Olympus IX81 with a 100× sapo objective with laser illumination at 532 nm, 594 nm, and 640 nm. Images were taken with Andor IQ software and an Andor Ikon CCD. FIONA images were acquired in 3 different fluorescence channels (Semrock zero line filters). The centroids of the FISH dots were calculated in each color or wavelength channel and a center of mass of all the dots were calculated and aligned between the channels by a simple translation. This was sufficient for most alignments without additional corrections from rotation and dilations.

STORM imaging was performed on a Nikon Tleclipse microscope with PFS autofocus lock. 640 nm laser (Crystallasers) was used as the main imaging laser and brought to the sample past the critical angle by a TIRFM objective. Lasers at 405 nm, 473 nm and 532 nm were used as activation lasers and automation is controlled by u-manager software. The microscope stages (Prior and ASI) were automated and also controlled by the acquisition software to enable multi-position imaging. Images were then analyzed in a custom written Mathematica script. Buffers used in STORM imaging follows the protocol similar to those in Bates et al., 2007, "Multicolor Super-Resolution Imaging with Photo-Switchable Fluorescent Probes," *Science* 317 (5845): 1749-1753, which (including any Supplemental Material) is incorporated by reference herein in its entirety. Glucose Oxidase was used as the oxygen scavenger and BME was used as the reducing agent.

Example 3

Barcoding Strategy

To multiplex mRNA detection in single cells, 9 target genes of the yeast transcription regulator Crz1 were chosen. A combination of barcodes was used to ensure the accuracy in determining the abundances of each of the genes. To do so, the simplest barcode was designed for the most highly abundant and shortest mRNAs. YLR414c and YLR194c are each 700 bps long and expressed strongly based on microarray experiments. Thus, they were assigned single color barcodes. Cmk2, another highly expressed gene, was also assigned a single color barcode with 12 paired-probes. The next tier expression levels are PMC1, NPT1 and YPS1. These genes were expressed at a lower level and were assigned a 2-position barcode. Lastly, Sok2, GYP7 and PUT1 are lowly expressed and were assigned the 3 different 3 color barcodes. As 3 color barcodes were resolved correctly 70% of the time, care was taken to avoid having the incorrectly resolved barcode leak into other barcodes at a significant level. Thus assigning the lowest expressed genes with the most complex barcode mitigates the crosstalk problems.

The barcoding capacity could be drastically improved by using repeat barcodes and more color than the three cy5-pair dyes (FIG. 9) as described herein.

Example 4

Single Cell Profiling and Correlation

The copy number of all of the genes was measured in single cells simultaneously by counting the number of super-resolution reconstructed barcodes (Table 1). Using this data, the distribution of copy numbers for each gene was determined (FIG. 3) and the pair wise correlation between target genes was calculated. As a control, cells treated with FK506, an inhibitor of the Crz1 pathway, showed negligible expression. This shows that Crz1 pulses are necessary but not sufficient for transcriptional bursts and the stochasticity in promoter initiation can produce uncorrelated bursting in the different targets.

Another question was whether transcription factor availability is limiting in creating stochastic transcription bursting. In order to investigate this issue, the same target genes were profiled in cells with Crz1 strongly expressed from a plasmid (PLE66). The affinity of the promoters to Crz1 can be inferred from the fold change in the expression level of that gene as Crz1 is over-expressed. High affinity promoters such as NPT1 and Pmc1 were expressed at the same levels in wt and over-expressed cells, suggesting the promoter is already saturated at wt Crz1 levels; while lower affinity promoters such as Cmk2 and YLR194c showed a 2 fold increase when Crz1 was over-expressed. There was a stronger correlation between the high affinity promoters, likely due to the tight coupling of transcriptional bursting with the Crz1 pulse. Meanwhile, the weaker promoters showed weaker correlation as they burst stochastically and independently following every Crz1 pulse. As Crz1 was over-expressed, the correlation among weak promoters increased, suggesting that promoter occupancy was enhanced. A smaller but non-zero population of cells exhibited bursting in only one gene in over-expressed cells, suggesting that promoter affinity does not explain all of the variations in correlations among genes. In addition, while not wishing to be bound by any one particular theory, no connection was found between chromosome positions and the gene correlations.

Figure 2:
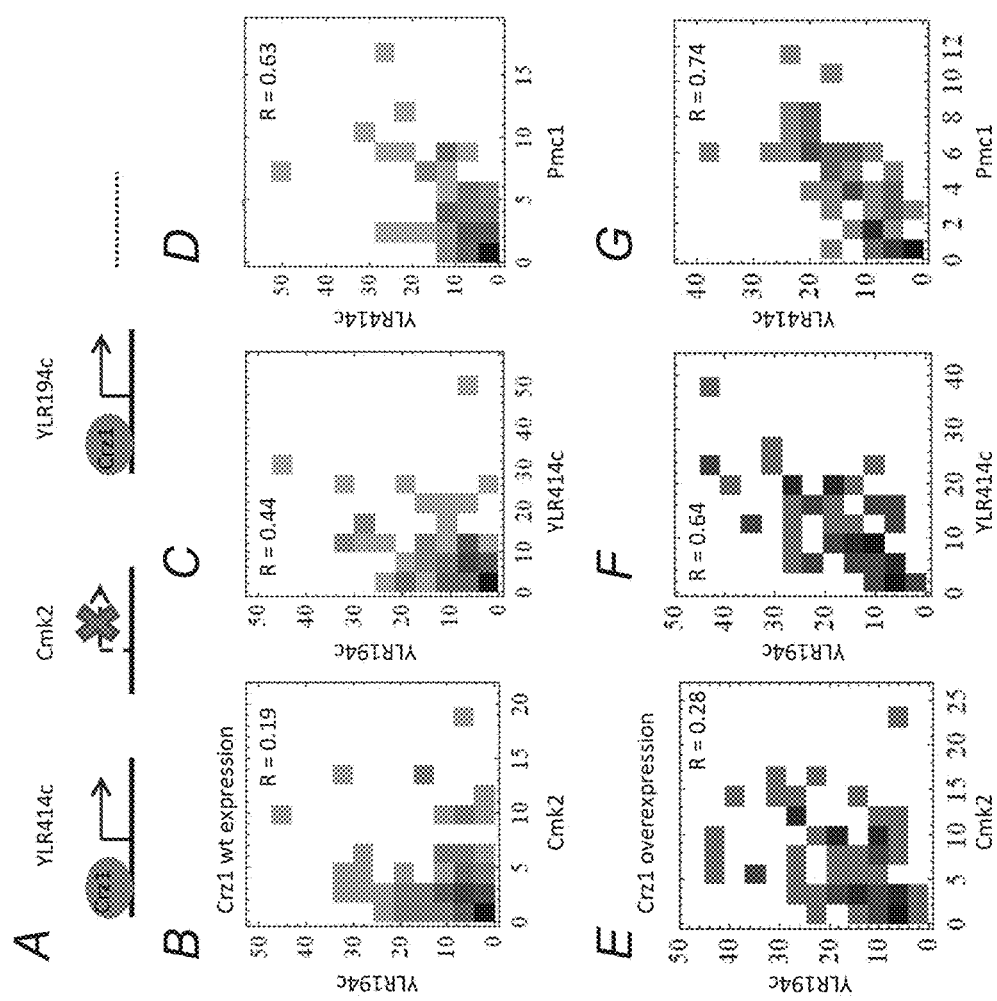
FIGS. 2A-2H depict, in accordance with an embodiment of the invention, Crz1 target genes respond stochastically to Crz1 pulses. A) Schematic of several promoters responding stochastically to Crz1. B-D) Pairwise correlations between target genes in wt cells. Correlation among promoters with low affinity to Crz1 is weaker than promoters with strong affinity to Crz1, suggesting transcriptional response to Crz1 pulse is stochastic at each promoter and depends on affinity. Promoter strength: Cmk2<194c<414c<Pmc1. E-G) Correlations in cells with over-expressed Crz1. Significant increase in correlation suggests that Crz1 occupancy controls the stochastic activation of the target promoters. H) A Petrie graph of a 4-dimensional hypercube with each node representing a state with a particular subset of the 4 genes (194c, Cmk2, 414c, Pmc1) strongly expressed. The size of the circle at each node corresponds to the fraction of total cells with that particular expression state. Note that while 194c and 414c are strongly correlated in a pairwise fashion (shown in C), few cells express strongly only 414c and 194c. When both 414c and 194c are expressed strongly, all genes are expressed strongly. The Petrie graph contains higher correlation information not present in the pair-wise correlations.
Figure 2:
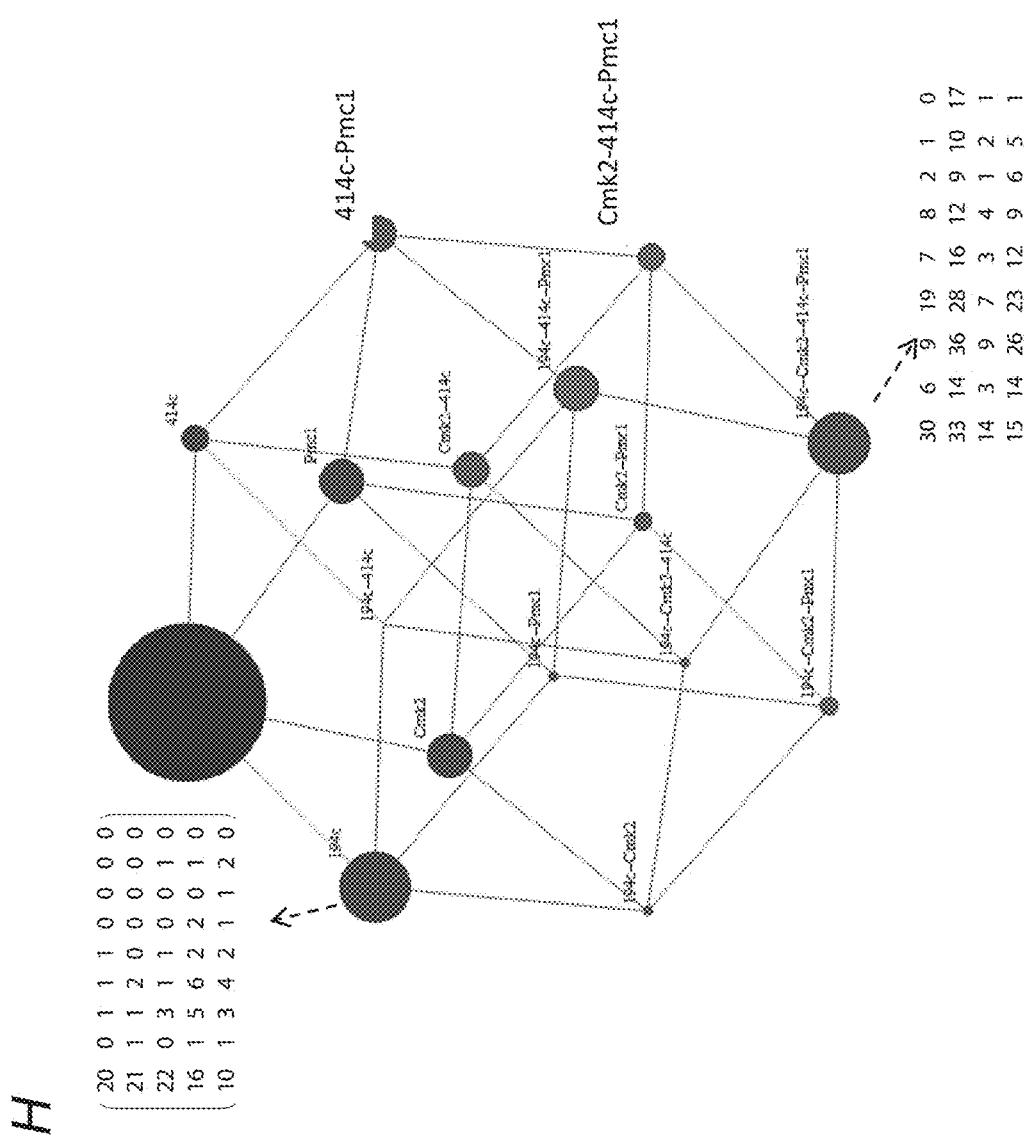

To elucidate a more global picture of how expression is correlated, higher order correlations are instructive. Each gene was classified as either highly or lowly expressed in a cell, thresholding on the average expression level of that gene in the population, for a total of 29 binary states. The dataset can be mapped to vertices of a 9 dimensional hypercube, which can be collapsed onto a Petrie projection graph (FIG. 2E). The size of the circle at each node of the graph corresponds to the number of cells with a given expression pattern. In a projection of the dataset focusing on 4 genes, it was observed that the expressions in most cells are either all high or all low, with a few cells expressing highly in only 1 or 2 of the genes. High affinity and weak promoters behave differently. Two weak promoters were rarely seen on at the same time, because if both of them are on, then the strong promoters are also bound and expressing. Thus, density is concentrated on singles or triplets or quadruplets. The higher dimensional correlations in the hypercube representation reveal the detailed structures in the regulatory network otherwise lost in the pair-wise correlations.

Example 5 mRNA Extension and Stretching by Compression

Extension of the mRNA to allow spatial resolution of the barcode is important to the high multiplex potential of the technique. Several approaches were tried to generate spatial extension. First, a DNA origami type of strategy was used to fold the mRNA into a stiff rod like configuration (FIG. 1G). This approach requires each FISH probe to hybridize on two distinct regions of the mRNA. The energy of the hybridization is supposed to fold the mRNA and staple it into a rod. While this approach works with in vitro transcribed mRNA, where an object migrating slower than the native mRNA is seen on the gel, it does not work in mRNAs in fixed cells. Probes were labeled such that if the mRNA were successfully folded, then cy3 and cy5 molecules labeled on the probes would be brought together within 1 m and a STORM signal would be observed. While Cy3 and Cy5 hybridization signals were observed, no storm switching and reactivation was observed. This indicates that the probes were bound in one of the positions of the mRNA, but were unable to bind to the other site and bring the mRNA into a more compact configuration. Several probe configurations with varying probe lengths (from 21 mers to 60 mers) were tested with the same results. Second, an electric field was applied to fixed cells in an attempt to generate an electrophoretic effect on the mRNA to lengthen it. Cells were embedded in low melting point agarose and positioned between 2 electrodes in an electroporation curvette to ensure the E field was applied in a uniform direction. The number of transcripts in the post E-field treated cells were the same as pre E-field treatment and the FIONA reconstructions showed no additional lengthening of the mRNA. These experiments suggest that the mRNA is rigidly held within the fixed cell and not movable by electromotive forces.

It has been suggested from previous FISH experiments that the mRNA is covalently attached to the protein matrix by formaldehyde. The inventors experimented with fixation methods where only proteins are crosslinked or precipitated to observe the effect on the mRNA. The inventors used the methanol fixation and DSS a NHS ester based protein crosslinker in separate experiments. As methanol fixation is supposed to only precipitate the proteins and does not crosslink nucleic acids, the inventors wondered whether they could move the mRNAs out of the cell with an applied E field. Again, the same copy number of transcripts was detected by FISH and the FIONA reconstruction showed no further extension of the mRNA compared to non-electrophoresed cells. While not wishing to be bound by any one particular theory his experiment strongly suggests that mRNA is fixed in the cells by interactions of the ribosomes on the mRNA with the protein background during fixation, rather than through direct nucleic acid to protein interactions. This is consistent with the lack of ability to use DNA origami methods to fold the mRNA. In a previous experiment, it was suggested short RNAs rapidly escape the cell during the hybridization process and these miRNAs are recovered in the solution. The inventors' observation of longer transcripts shows that physical escape of the transcript from the cells is improbable and likely hindered by ribosomes, whereas most of the shorter miRNAs likely do not associate with proteins and thus are not permanently fixed in the cell. Experiments in which Puromycin and Harringtonine were used to dissociate or stall the ribosomes were inconclusive, probably due to poor permeability and poor kinetics of the compounds at 25-30° C.

Figure 3:
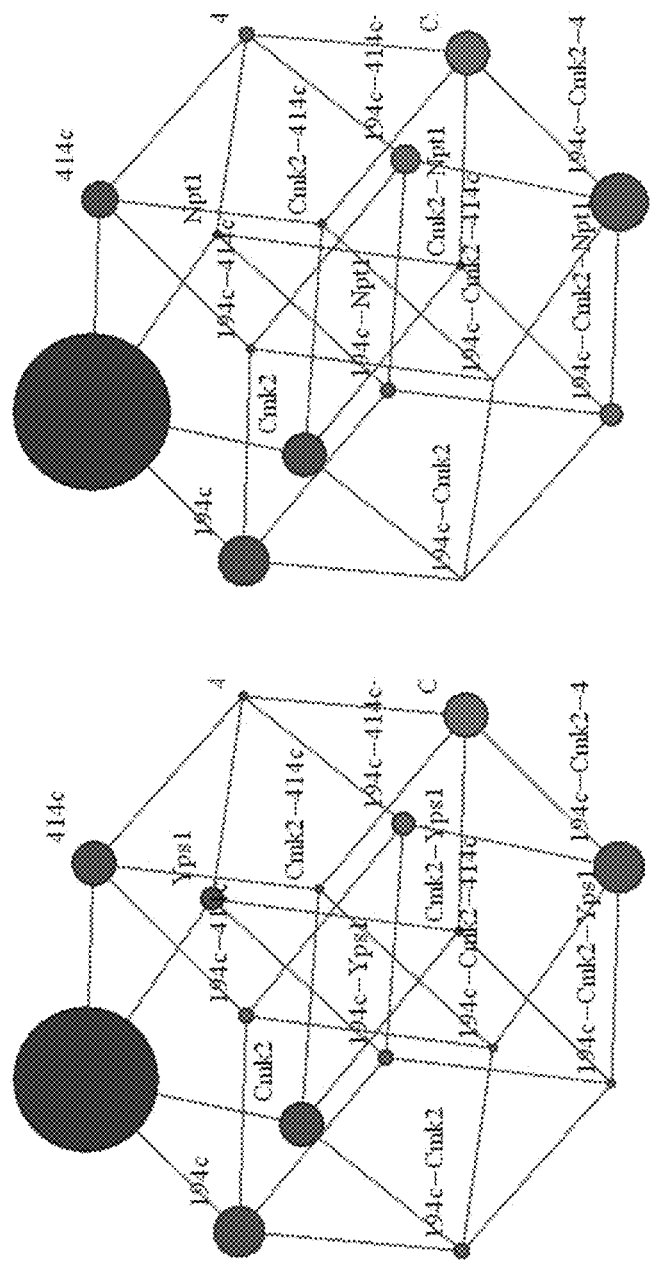
FIG. 3 depicts exemplary embodiments.
Figure 4:
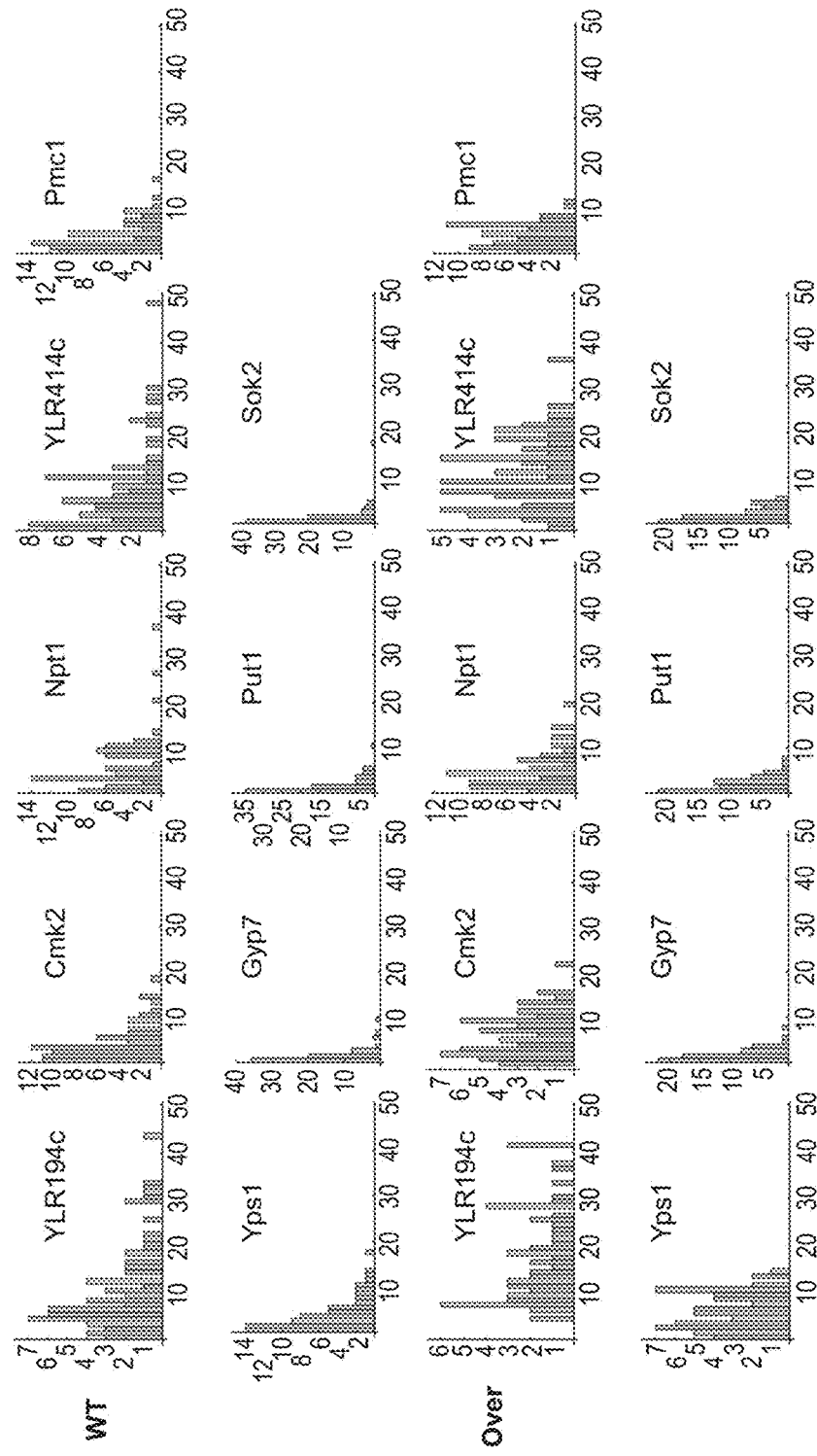
FIG. 4 depicts, in accordance with an embodiment of the invention, the distribution of target mRNA copy number in single cells (Wt vs Crz1 over-expressed).
Figure 5:
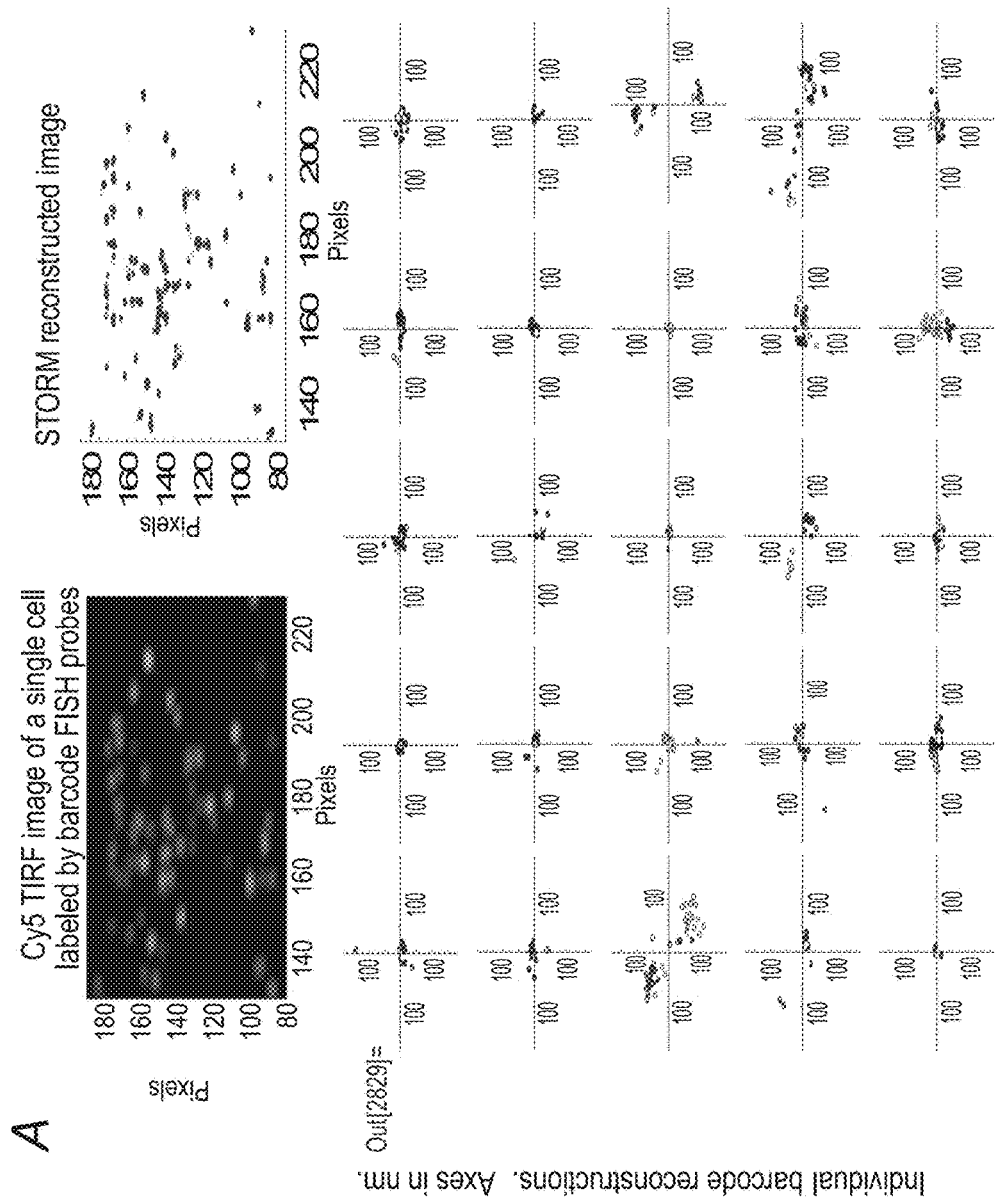
FIGS. 5A and 5B depict in an exemplary embodiment, single cell in Total Internal Reflection Fluorescence Microscope (TIRFM) imaging and Stochastical Optical Reconstruction Microscopy (STORM) reconstruction.
Figure 5:
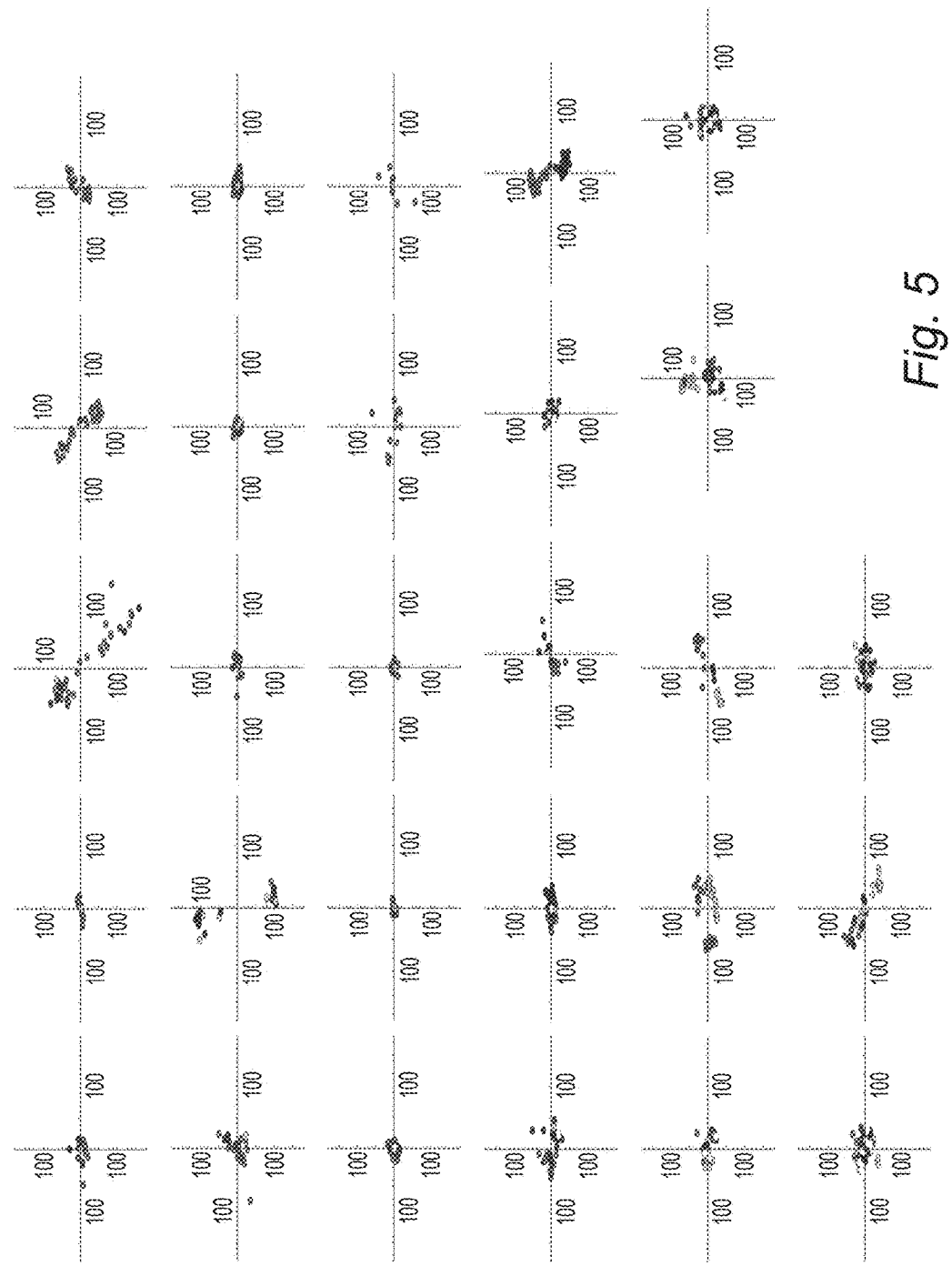
Figure 6:
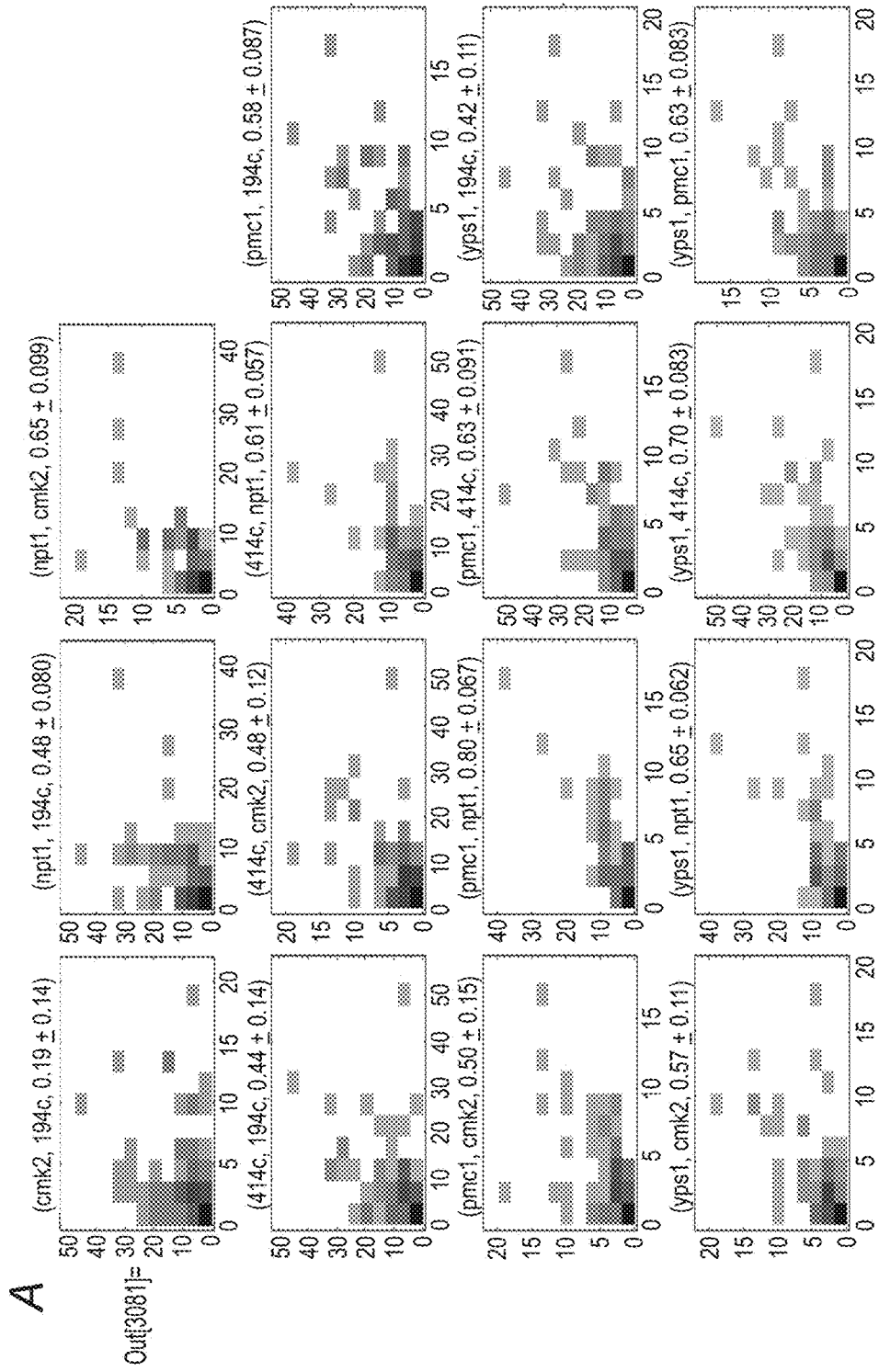
FIGS. 6A and 6B depict, in accordance with an embodiment of the invention, pairwise correlations in WT (A) and over-expressed Crz1 cells (B). Correlation coefficient and error bar are shown with the gene names.
Figure 6:
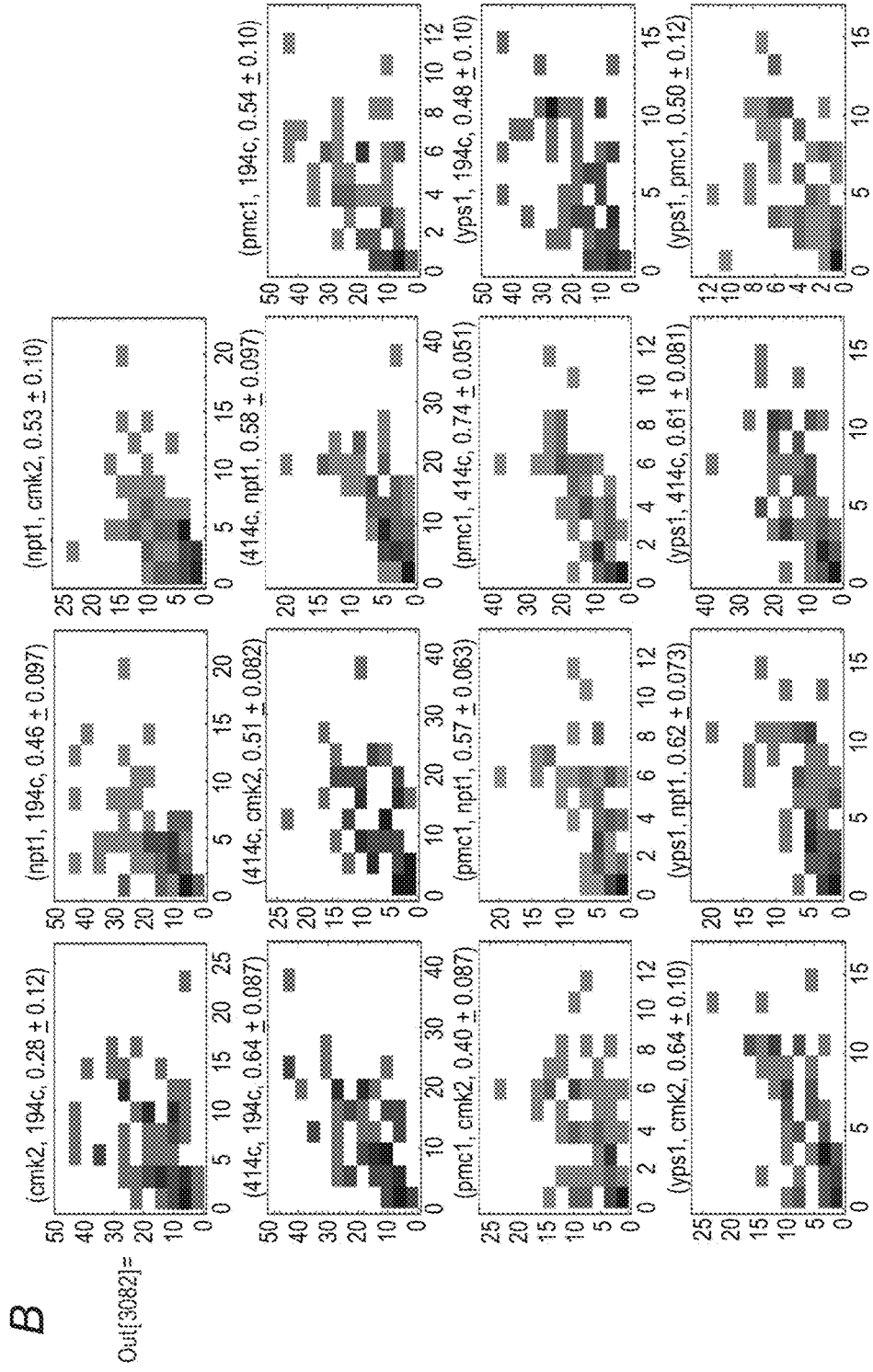

Thus, while not wishing to be bound by any one particular theory, one of the best mechanisms for the extension of mRNA is by physical compression of the cells as they are sandwiched between coverslips during imaging. As the mRNAs are held in place by ribosomes fixed to the cellular matrix, a flattening of the cells creates a shear flow within the cells that moves the ribosomes and stretches the mRNA out in the lateral direction (FIGS. 3 and 4). Another possible explanation is that hybridized mRNAs are stiff and compression of the cell merely flattens the mRNA in the xy direction. However, given the persistence length of double stranded DNA is 150 nt and that a hybridized mRNA resembles a nicked RNA-DNA hybrid rather than a full double stranded molecule, it is unlikely that hybridized mRNA is already extended. This possibility can be ruled out with axially resolved STORM by incorporating a cylindrical lens in the setup. However, the axial resolution of the approach is 50 nm, insufficient to further resolve the typical 20-50 nm distance between the barcode positions. Compression of fixed embryos is routinely used to decrease the sectioning thickness for imaging in FISH experiments. Thus, such physical compression of the sample may serve the purpose of extending mRNAs for the barcode resolution.

Example 6

Barcoding Multiple mRNA Transcripts in Yeast

To demonstrate the feasibility of this approach, multiple mRNAs species in single *Saccharomyces cerevisiae* cells were detected using the methods and system described herein. The current methods and systems differ from the single molecule FISH (smFISH) techniques. Instead of detecting each mRNA with 40 20 mer oligonucleotide probes labeled with the same fluorophore as in smFISH, a nanoscopic barcode was imparted on each transcript by hybridizing probes labeled with different fluorophores in a spatially ordered fashion. The current SRM resolution of 15 nm allows a code region of 50 bp long to be resolved. Different species of mRNA can be uniquely barcoded and quantitated by tabulating barcodes in individual cells (FIG. 1). Previous works in multiplex FISH rely on using intensity ratio of fluorophores to label distinct chromosomal loci, and transcriptional active sites. The current approach spatially barcodes single mRNAs in a 5' to 3' fashion, allowing potentially limitless capacity for multiplexing and the spatial capacity to accommodate all transcripts in the cell.

It was first demonstrated that barcodes on mRNAs can be resolved spatially, using Fluorescence Imaging with One-Nanometer Accuracy (FIONA). Twelve oligo probes targeting GFP mRNA were grouped in sets of 4 and labeled by 3 different fluorophores. In hybridized yeast cells, target mRNA appeared as co-localized, near-diffraction limited, spots in the fluorescence channels. 99±2% of spots co-localized in all three channels and each spot typically consists of 2.7±1 probes, as determined by photobleaching (SOM). These results suggested that hybridization is 70±10% efficient and single labeled probes can be readily detected. The centroid positions of the probes can be determined accurately by Gaussian fitting, with a localization accuracy of ~5 nm (with ~104 photons), and with an error of ~5 nm due to chromatic aberration in our imaging setup (SOM). Following center-of-mass image alignment, the correct spatial order was observed in 80±10% of the labeled mRNAs, with the average spatial separation of 25±10 nm between centroids. The spatial distances is shorter than the 40 nm expected for a fully extended 120 bp region of hybridized mRNA, but significantly more than the potentially folded native structure of the mRNA. It was hypothesized that a partially stretched mRNAs is observed, because as the cells are sandwiched between 2 glass coverslips for imaging, the compression of the cells generates a shear flow acting on the ribosomes attached to the mRNA, resulting in extension of the mRNA in the planar direction. This extension of the mRNAs from their native conformation allows the 80% fidelity in reading out the barcodes.

To demonstrate the robustness of the FIONA barcode technique, the order the fluorophore labeling was switched and the distances between 2 barcode positions was increased. The corresponding switch was observed in the ordering of the centroids with 70±10% correct ordering as well as the lengthening of the distances between the barcode positions (from 25 nm to 40±10 nm). In addition, mRNAs of different lengths from 700 bp to 14 kb were labeled using this method, without observing significant differences in the detection of the correct ordering of the barcode. The FIONA approach is easy to implement with conventional fluorophores and has high localization accuracy. However, the approach is limited in labeling density by diffraction and prevents repeat usage of colors for coding. For example, a RGR coding scheme cannot be resolved by FIONA, as the two red positions are within the same diffraction limited volume. To circumvent both problems, photoswitchable fluorophores were used to label the oligonucleotide probes.

A barcode from photoswitchable dyes labeled oligos based upon the Cy5 dye-pairs were used. In the STORM experiment, an activator dye (Alexa 405, Alexa 488, or Cy3) were placed in close proximity (~1 nm) to the switchable dye (Cy5, Cy5.5 or Cy7). As Cy5 is imaged and switched off by a 640 nm laser, it can be stochastically re-activated by weak illumination in the activator dye wavelength. Three activator dyes can be paired with three emitter dyes to provide 9 colors in STORM. The probes were designed such that two probes, one labeled in its 3' position with the activator and the other in 5' position with the Cy5 emitter dye (FIG. 9a), were hybridized on the mRNA at adjacent positions separated by 2 bp, bring the dye pairs within 1 nm. As both probes are required for the fluorophore to be re-activated, non-specifically bound Cy5 probes in the cell cannot be reactivated after the initial switching off step. In contrast, directly labeling oligos with Cy3-Cy5 covalently-linked pairs will have the same non-specific background as standard FISH and have drastically increased blinking rate.

Since the images were all acquired in the Cy5 channel, there is no need for chromatic aberration corrections. Three color barcodes (FIG. 9) can be reconstructed from the super-resolution movies and the correct order resolved 70±10% of the times independent of mRNAs species (FIG. 9). In addition, colors could be used repeatedly, i.e., RGR, (FIG. 9), which in principle allows limitless number of unique barcodes. Given the typical size of the barcodes (100 nm), a typical yeast cell with a diameter of 5 um can accommodate >100,000 barcoded transcripts per cell, comparable to the size of the yeast transcriptome.

Practically, the accurate readout of barcode is constrained by the hybridization efficiency and non-specific blinking of the Cy5 dyes which distort super-resolution reconstruction. As each probe has 70% chance of hybridizing, the pairs are generated successfully 50% of the time. With 4 redundant probe pairs per barcode position, the chance of having all three positions present with at least one pair of probes is 81%, consistent with the inventors' observation that 77% 3 color codes are complete. In the directly labeled probes used in the FIONA experiments, a 4 probe redundancy was sufficient to ensure that 98% of time at least one probe is bound in each channel. Thus, it was anticipated that with the development of fluorophores with improved non-specific activation rates. Thus, barcodes could be reconstructed more accurately, and oligo probes could be labeled directly to increase the chance that all the code positions are present.

The unique capabilities of the barcoding FISH approach in studying genetic networks in single cells was demonstrated by profiling a set of co-regulated genes controlled by a transcription factor Crz1. It was previously shown that Crz1 pulses in its nuclear localization in frequency-modulated fashion. However, not every Crz1 localization pulse gives rise to a transcriptional burst in a particular target gene. The super-resolution barcoding approach allowed the inventors to determine whether these transcriptional bursts were uncorrelated across different target genes, suggesting an intrinsic source of stochasticity at the promoter, or correlated, suggesting extrinsic contributions. By fixing cells in conditions in which the interval between Crz1 pulses is longer than the typical mRNA lifetime, the distribution of transcriptional responses among genes to each Crz1 pulse in single cells can be captured.

Nine Crz1 target genes were chosen based on previous microarray and flow-cytometry experiments to represent a range of expression levels and loci on different chromosomes (Table 1). The transcripts were encoded in a manner analogous to Huffman coding, with the highest expressed genes assigned the least complex barcode. As the inventors' 3 color barcodes have an error rate of 20% in crosstalk to the 2 color barcodes due to hybridization efficiency, assigning the lowest expressed genes with 3 color codes diminishes the error in over-estimating the abundances of 2 color coded genes. From tabulating barcodes, the distribution of copy numbers for each gene was determined, and the pairwise correlation between target genes was calculated. Significant stochasticity was found in the expression levels for many of the genes (CV=0.9±0.1), suggesting presence of transcription bursts. In addition, large variability was observed in the pairwise correlation between different genes, from $R=0.19±0.14$ to $R=0.8±0.07$. In genes pairs that were weakly correlated, a stark disparity in expressions was observed in >50% of cells in which some genes were clearly highly expressed with a copy number of 20-30 per cell, while others genes in the same cells were not expressed at all (FIG. 2b). It was shown that the strength of correlation is related to the promoter affinity to Crz1: Promoters with high affinity for Crz1, such as NPT1 and PMC1 were found to be more correlated compared to promoters with weaker affinities such as YLR194c and Cmk2, and were unrelated to chromosomal location (SOM). Affinity does not correlate with the expression levels of the promoter. Furthermore, it was determined that over-expression of Crz1 significantly improves the correlation among genes, especially among weak promoters (FIGS. 2e-g). While not wishing to be bound by any one particular theory, these results strongly suggest that the randomness in Crz1 occupancy at the promoter is responsible for the stochastic and uncorrelated transcription bursts in the network of targets genes.

TABLE 1

Single cell measurements of Crz1 target genes.

|  | YLR19c (BBB) | CMK2 (GGG) | YLR414c (RRR) | NPT1 (G-B) | PMC1 (R-B) | YPS1 (R-G) | GYP7 (GRB) | PUT1 (RGB) | SOK2 (RBG) |
|---|---|---|---|---|---|---|---|---|---|
| Cell 1 | 2 | 3 | 5 | 2 | 1 | 0 | 0 | 0 | 0 |
| Cell 2 | 9 | 6 | 13 | 2 | 1 | 3 | 0 | 0 | 0 |
| Cell 3 | 14 | 6 | 8 | 4 | 1 | 4 | 1 | 2 | 1 |
| Cell 4 | 14 | 3 | 17 | 0 | 4 | 1 | 0 | 0 | 0 |
| Cell 5 | 0 | 3 | 13 | 4 | 0 | 0 | 0 | 1 | 0 |
| Cell 6 | 5 | 1 | 7 | 3 | 5 | 1 | 0 | 0 | 0 |
| Cell 7 | 11 | 7 | 9 | 8 | 3 | 4 | 0 | 2 | 3 |
| Cell 8 | 23 | 24 | 46 | 5 | 10 | 6 | 5 | 5 | 1 |
| Cell 9 | 9 | 9 | 21 | 5 | 0 | 2 | 0 | 0 | 0 |

R: Red;
G: Green;
B: Blue.

Nine genes were barcoded with each circle representing 4 pair of probes, and their abundances in individual cells were tabulated. Note the heterogeneity in expression levels within a single cell.

The multidimensional transcriptional dataset captured by barcoded FISH cannot be fully represented through pairwise correlations. To present in an intuitive manner the higher order correlations in the Crz1 targets, each gene was classified as either highly or lowly expressed in a cell, thresholding on the average expression level of that gene. The states were then enumerated with a given subset of genes highly expressed and represent the probability of finding cells in that state by the size of the circle in FIG. 2H. In a projection of the dataset focusing on 4 genes for clarity, it was observed that a range of expression states is populated, but not all states are equally probable. In particular the states representing coincidences of high expressions in weak promoters have the low occurrences. While YLR414c and YLR194c are relatively well correlated in a pairwise fashion (R=0.44±0.14, FIG. 2C), cells with only both YLR414c and YLR194c highly expressed were not observed (FIG. 2H). This apparent contradiction was resolved by noting that in cells with both YLR414c and YLR194c highly expressed, the other genes Cmk2 and PMC1 were also likely to be highly expressed, occurring in 10.1±3.5% of the cells. The same high degree of correlation was observed in 10.1±3.5% of the cells with a larger set of genes. These results suggests an extrinsic factor, such as variations in the localization intensity of each Crz1 pulse, contributes to the higher order correlations among genes in addition to the intrinsic stochasticity at the promoters level, accounting for between 20-80% of the variations observed depending on promoter affinity.

Super-resolution barcode FISH(SURF) of the present invention highlights an alternative path to genome-wide transcriptional profiling in single cells. Nine genes were multiplexed by utilizing only 3 super-resolution colors, without the use of repeated barcodes (FIG. 9), and without resolving objects in the axial direction. By incorporating an expanded palette of super-resolution fluorophores with higher localization resolution and contrast ratios, it is possible to increase the labeling density and multiplex capability dramatically, potentially to the genome level. Thus, SURF has the potential to be a powerful technique and offers several distinct advantages compare to the approach of directly scaling down current high-throughput techniques to the single cell level. First, it bypasses the problems of limiting starting material and amplification error associated with working with single cells. Second, it avoids the laborious and error prone process of isolating single cells from tissues or cell aggregates. As in situ observations retain the spatial and cellular context of genetic information, this approach has powerful applications to a large range of biological systems from biofilms to embryos where interactions among heterogeneous cellular populations play an essential role. Third, it is cost and information efficient as many cells can be imaged simultaneously under a microscope, whereas sequencing individual cells to generate a large dataset can quickly become expensive. Lastly, with the development of versatile aptamers and synthetic antibodies, SURF may be generalized to a large pool of molecules, bringing the power of genomics into single cell system biology.

Experiments II

Example 7

Additional Spatial Labeling of mRNAs

Figure 7:
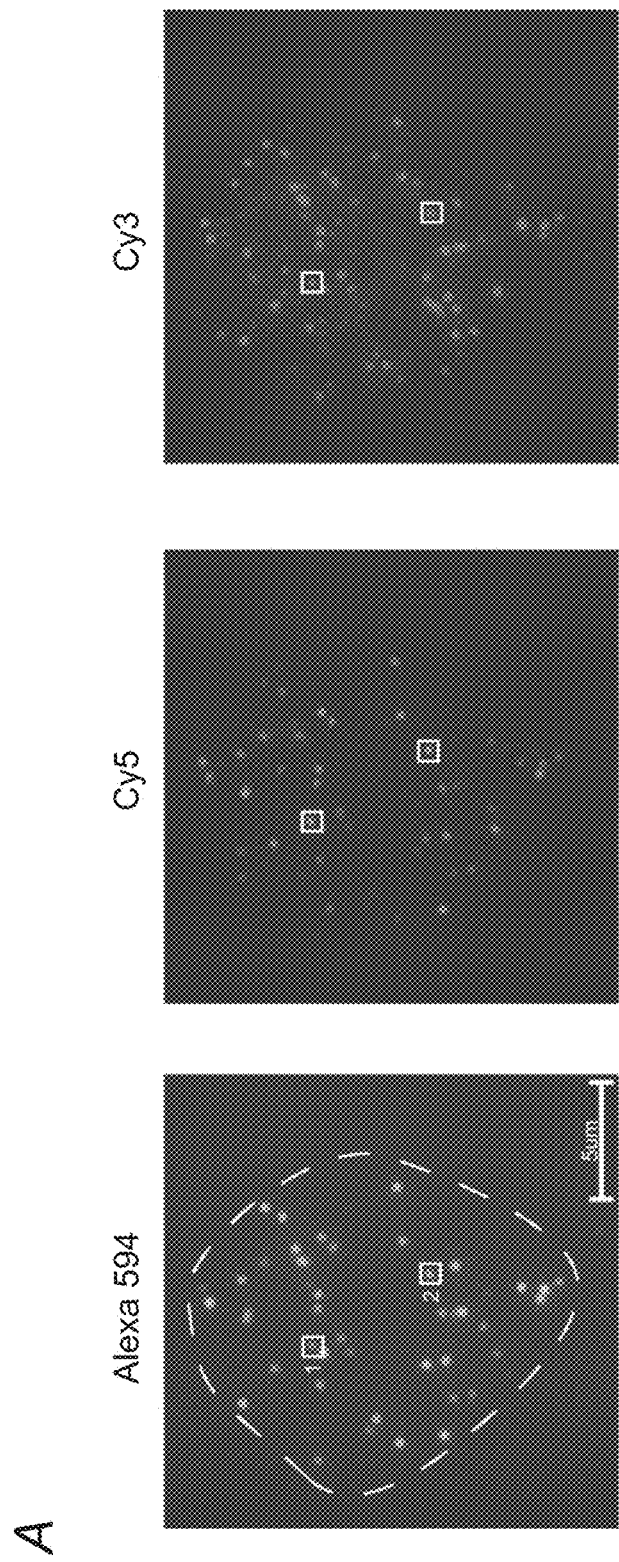
FIGS. 7A-7H depict, in accordance with an embodiment of the invention, FIONA can resolve spatial ordering of fluorophores on mRNAs. A) Fluorescence images of YLR414c probes hybridized in a single budding yeast cell, shown in each channel. B) Probe Schematic. Labeled 25 mer oligonucleotides are hybridized to YLR414c mRNA. C) Reconstructions of the centroids of spots 1 and 2 following localization by Gaussian fitting and image alignment. D) The percentage of co-localized YLR414c three-color dots that can be reconstructed in the above image (A) with the correct barcode (n=28, Correct Order=74±8%). E) Schematic of probe-set hybridized to GFP mRNA with different order and distances between the probes positions. F) FIONA reconstruction of this probe set. G) The distance between the resolved centroid positions (d1=27.93±14 nm, d2=56±33 nm) is proportional to the intramolecular distance between barcode positions (190 and 350 bp). H) The frequency of barcode identification for this probe set (n=327, correct order=76±2%).
Figure 7:
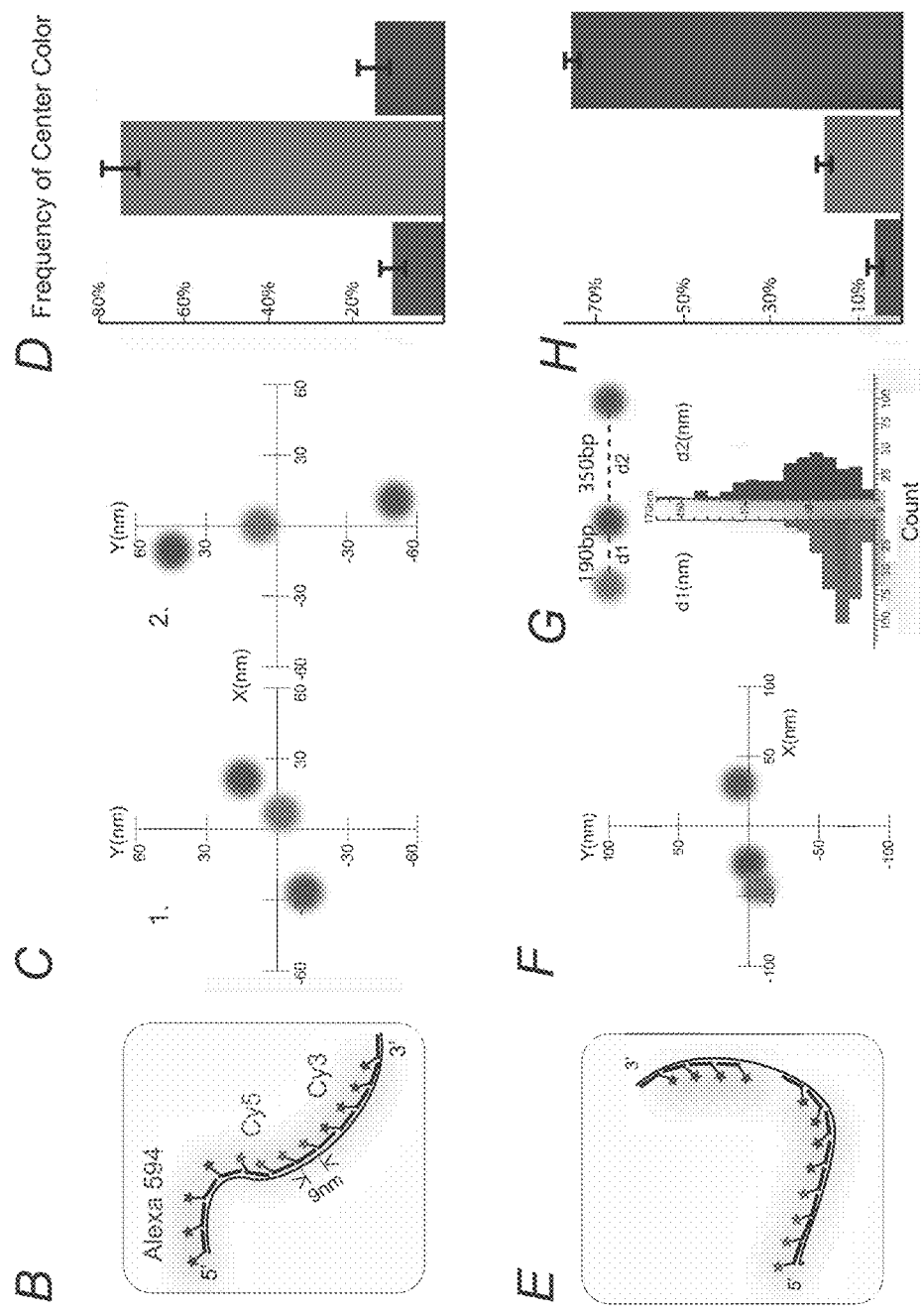
Figure 16:
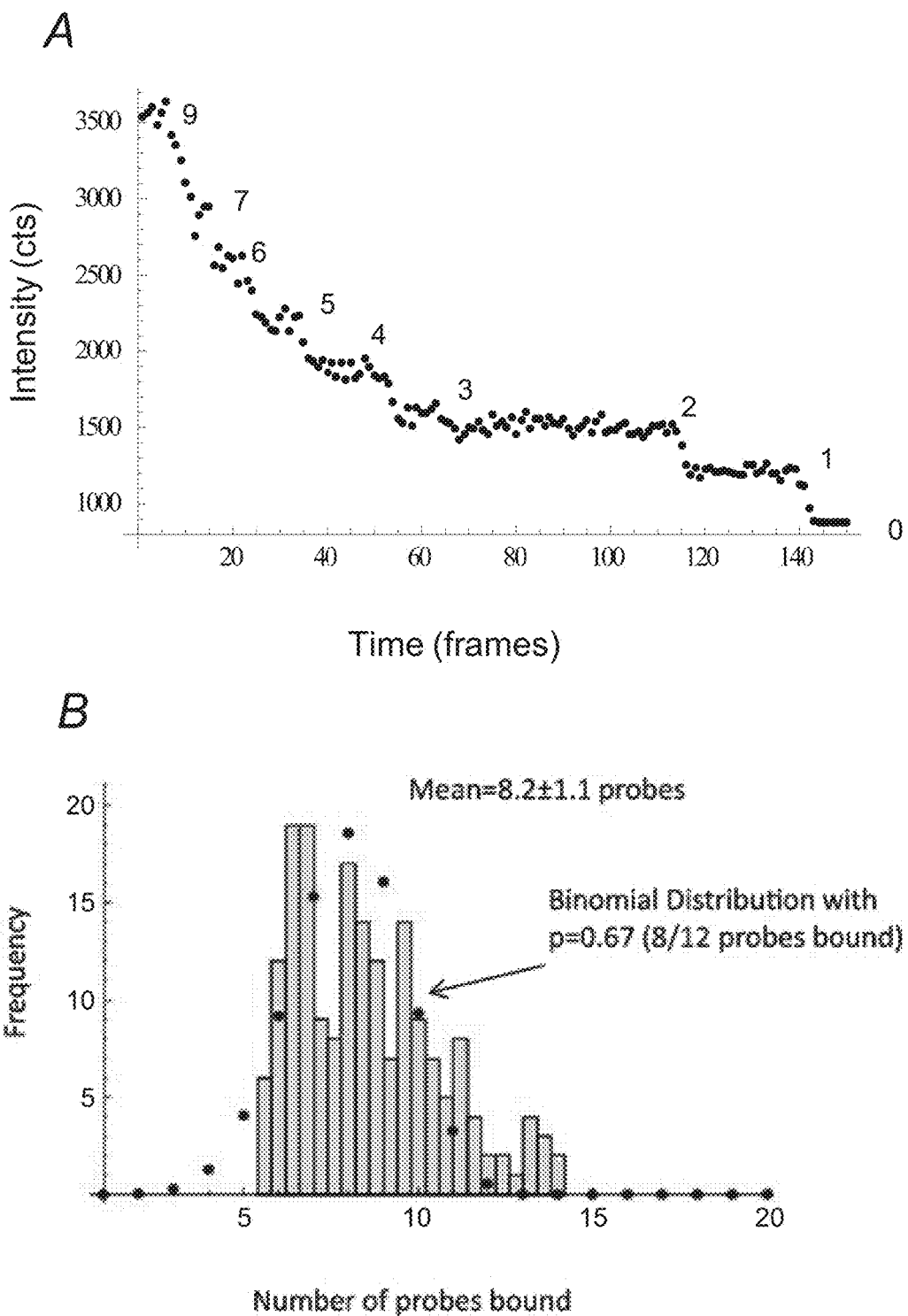
FIG. 16 A-D depict exemplary embodiments of the invention. A) Sample photobleaching traces. Cmk2 mRNA was hybridized with 12 27 mer probes labeled with Cy3. The sample was illuminated with a 532 nm laser for 150 frames. No antibleaching buffer was used. Stepwise drops in fluorescence intensity correspond to photobleaching of a single fluorophores. The intensities of fluorophores were not uniform, possibly due to micro-environment and homo-FRET quenching. On average each step corresponds to ~300 cts, with a background of ~900 cts. The initial intensities suggest, in both traces, 8-9 probes out of the 12 probes were bound to the mRNA, corresponding to ~2/3 hybridization efficiency for each probe. B) Distribution of hybridization efficiencies for the Cmk2 probe set. The number of probes bound is determined from the initial intensities of dots observed prior to photobleaching divided by the average step size. The mean number of probes bound was 8.2±1.1. This distribution is overlayed with a binomial distribution with a probability of each probe bound at 67%, corresponding to 8 out 12 probes bound on average. C) FIONA reconstructions of barcodes on YLR414c mRNAs in a single cell in FIG. 9. 5' modified YLR414c probes were used. The intensity profiles of the dots in each channel are shown in the right panels, corresponding to Cy5, 594, and Cy3 channels. The reconstructions from Gaussian fitting of the intensity profiles are shown in the left. mRNAs are selected by intensity thresholding in all three channels. D) Spatial separation between terminal and center positions of the barcode. The distances between the Alexa 594-Cy5 and Cy3-Cy5 probe positions was both ~240 bps, reflected in the symmetrical mean physical distances observed.
Figure 16:
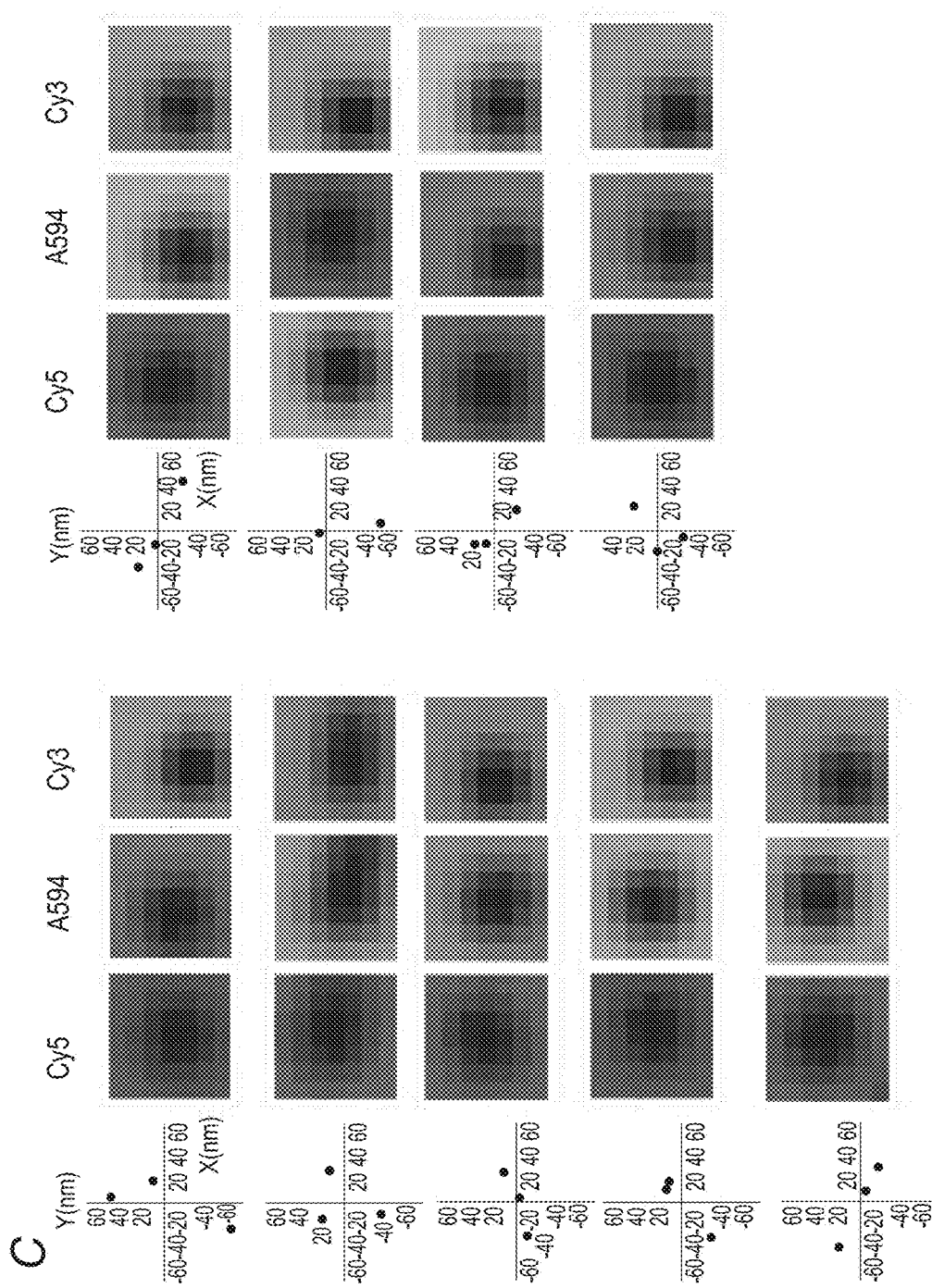
Figure 16:
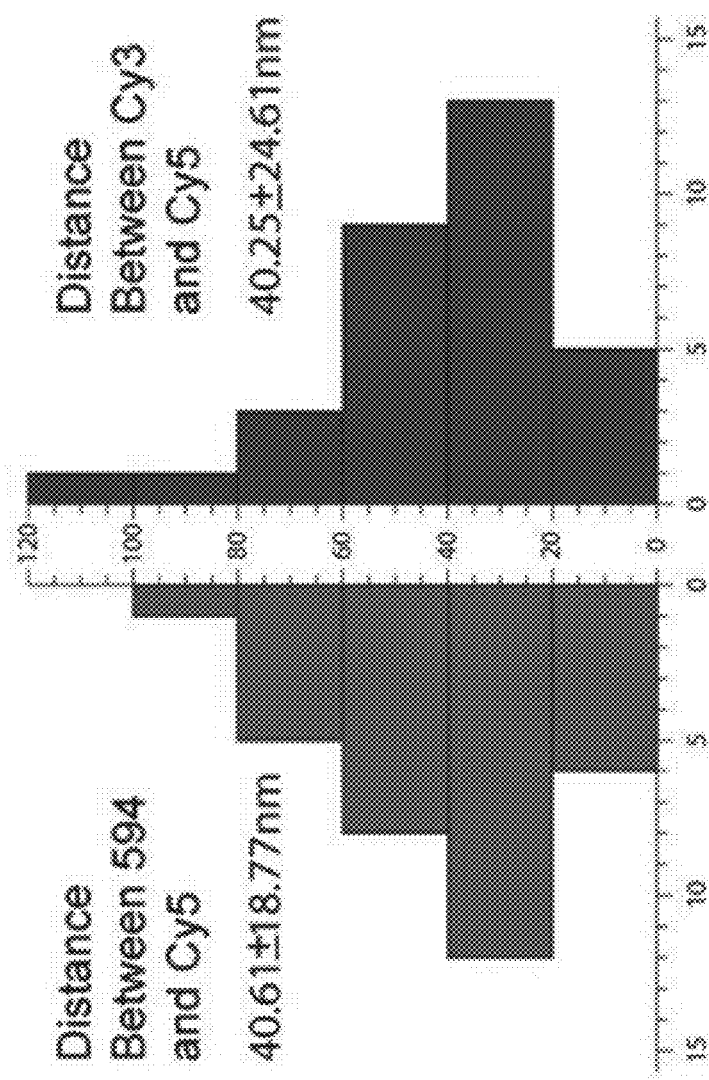

In experiments related to those previously described herein, the inventors targeted the YLR414c mRNA with 3 sets of oligo probes labeled with different fluorophores (FIG. 7). These probes were tiled along the mRNA in a 5' to 3' spatially ordered fashion. Hybridized mRNAs appeared as co-localized and diffraction-limited spots (FIG. 7). The inventors observed that 96±2% (N=29) spots co-localized in all three channels of YLR414c probes, indicating efficient hybridization of the probes. If probes were poorly hybridized, then a larger fraction of the mRNAs would only appear in one or two of the channels. The inventors further quantified the hybridization efficiency of FISH probes by determining the number of fluorophores bound at each mRNA through photobleaching (FIG. 16). Discrete steps of photobleaching corresponded to the bleaching of individual probes bound to mRNA. The inventors determined that each probe on average has a 67.5±9.1% (FIG. 16) probability of binding. With 4 probes in each code position, this translates to a 99% labeling efficiency and a 96% co-localization rate. These measurements demonstrate that individual mRNAs can be readily labeled with a small number of FISH probes and observed with high fidelity. As previously demonstrated herein, even though each mRNA appears as a co-localized diffraction limited spot, the position of each labeled region of the probes can be determined to much higher resolution. The centroid position of each group of probes labeled with the same fluorophore can be found by fitting the fluorophore intensity profiles with 2D Gaussian functions. Aligning the different channels allows the identification of the spatial ordering of the probes on mRNA. For these experiments, the inventors observed the correct spatial order in 74±8% (N=28) of 3-color co-localized mRNAs (FIG. 7d, 16). Error in detecting the order of the barcode (26%) may result from a combination of factors, including localization error, lack of z resolution, and mRNA secondary structure. As the inventors placed cells between glass coverslips for imaging, compression on the cells doubled the radius of the cells in the XY-dimension and reduced the depth of cells to approximately 1 um. Consequently, the fluorescent background was dramatically decreased in cells. As previously indicated herein, compression forced objects to stretch in the XY-dimension, and the tertiary structure of fixed mRNA was partially stretched across the optical plane of the microscope, significantly increasing the detection fidelity of spatial ordering in 2D. The average spatial separation between centroids for these experiments was 40.6±18.8 nm (N=56) (FIG. 16d), shorter than the 80 nm expected for a fully extended 240 bp region of hybridized mRNA. As mRNA is unlikely to be fully extended or completely parallel to the imaging plane of the microscope, the inventors did not expect to observe the full extension distance between probes. To demonstrate the robustness of the barcode readout, the inventors switched the order of fluorophore labeling and doubled the distance between one pair of barcode positions with respect to the other (FIG. 7e). The inventors were able to detect the correct ordering in 75.5±2% (FIG. 9h, N=327) of the molecules in these experiments. The inventors observed the expected change in spatial relations between probes. The distances between the two terminal and center probe positions were 27.93±14 nm to 56±33 nm respectively, proportional to the 2-fold difference in their nucleotide distances (FIG. 7g). When the inventors labeled different mRNAs, they observed no significant difference in barcode readout fidelity, suggesting that barcode readout is robust regardless of mRNA species.

Example 8

Detecting Alternative Splicing in Single Yeast Cells

Figure 8:
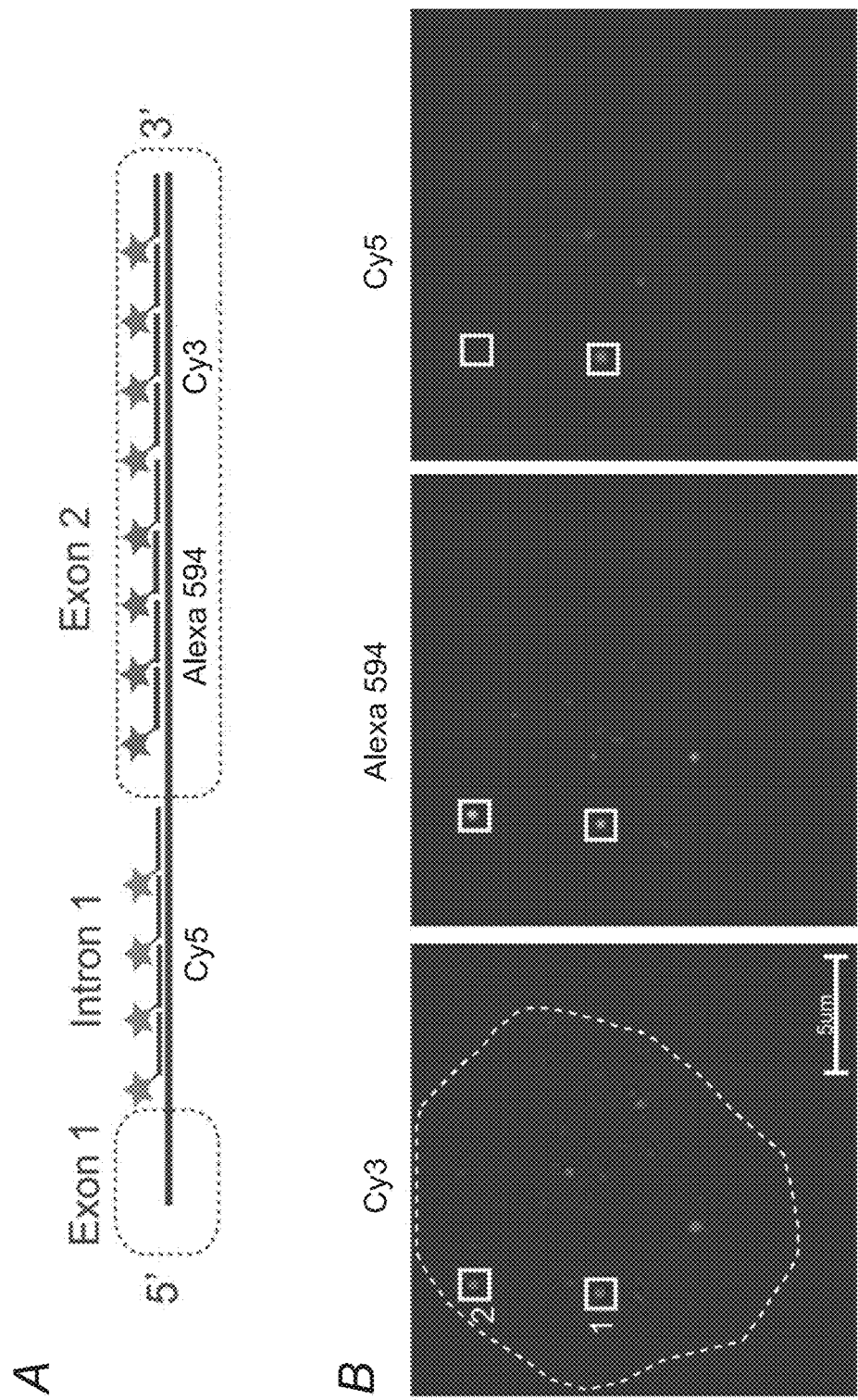
FIG. 8 depicts, in accordance with an embodiment of the invention, alternative splicing of PTC7 monitored with barcode FISH. A) Schematic of PTC7 mRNA and probes. A labeled intron is flanked by a labeled exon and unlabeled exon. B) Detection of PTC7 splicing in single yeast cells. Co-localization of Cy3 and Cy5 indicate detection of the exon while co-localization of the exon with Cy5 denotes a splice variant containing an intron. C,D) Centroid reconstruction of spliced transcripts. C) Box 1 from part B: an unspliced transcript. D) Box 2 from part B: a spliced transcript. E) Copy numbers of spliced and unspliced transcripts in single cells. A heterogeneous pattern of splicing is observed (N=98).
Figure 8:
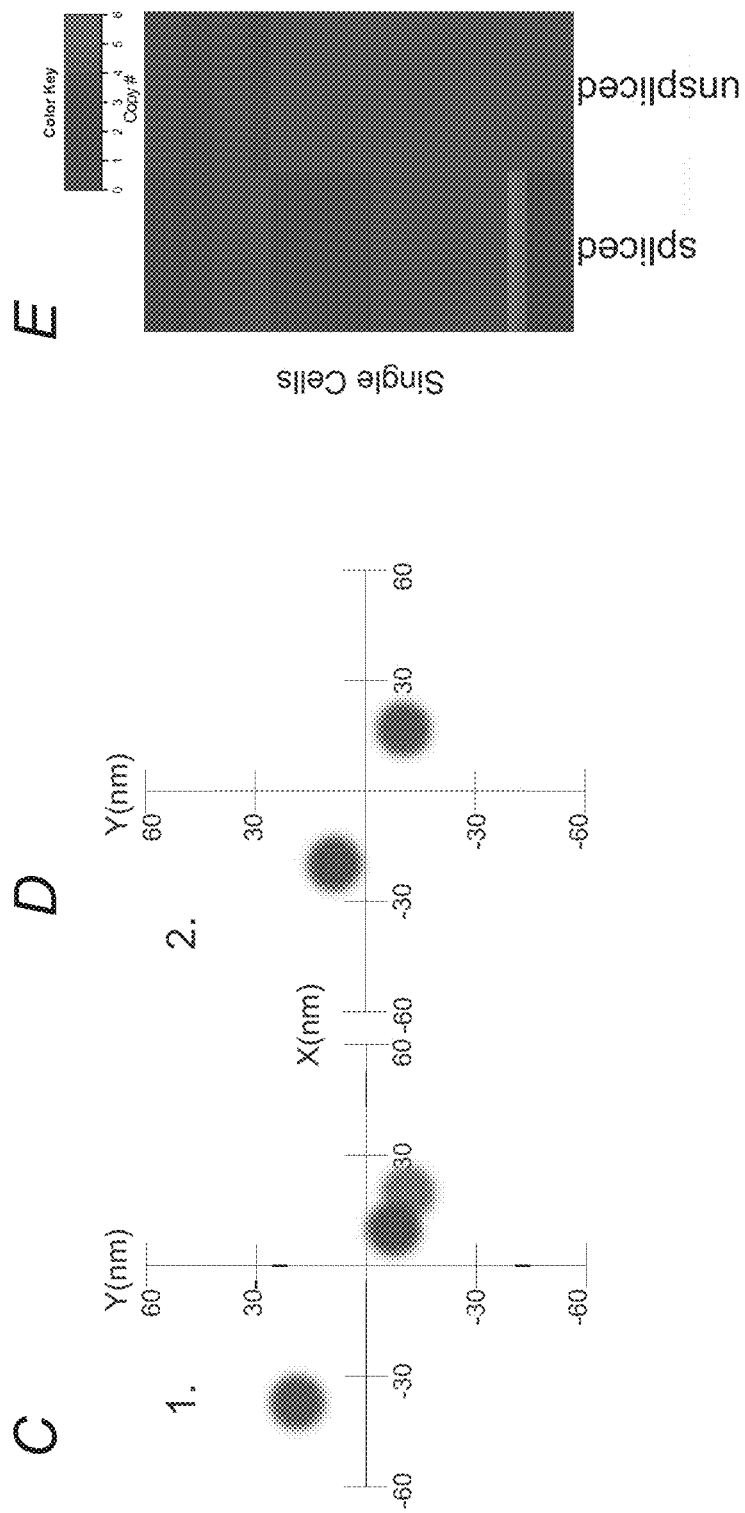
Figure 23:
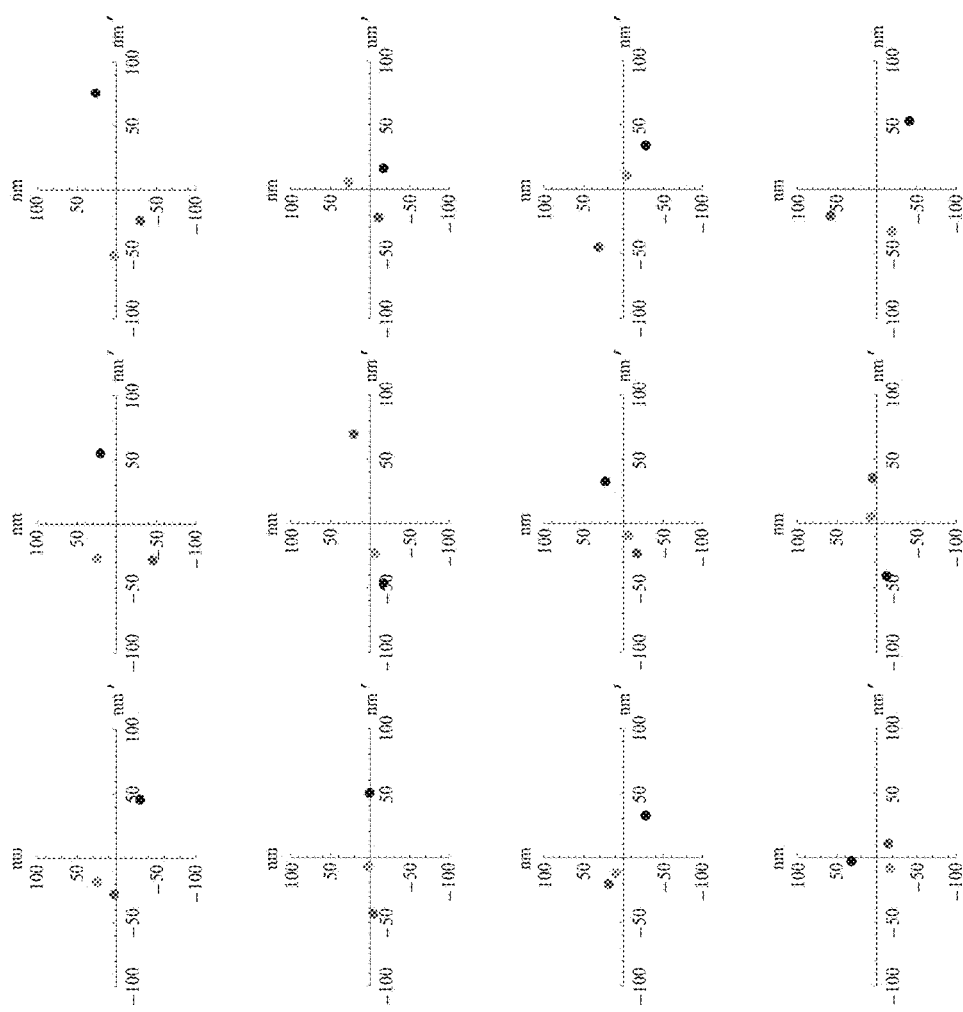
FIG. 23 depicts, in accordance with an embodiment of the invention, Ptc7 centroid reconstructions. Reconstructions are only shown for unspliced transcripts. The correct barcode is Red-Green-Blue. The low number of unspliced transcripts introduces more errors in the alignment process. An external fiducial marker would improve the alignment accuracy and the barcode readout rate.

Alternative splicing is ubiquitous in eukaryotes and significantly increases the complexity of the proteome. Recent deep sequencing experiments reveal that 30% of the human genome is spliced with an average exon size of 50-100 bps. Alternative splicing occurs stochastic in individual cells and has been shown to be crucial in cellular differentiation and patterning events. Thus, it is important to determine the distribution of splice variants that are present in individual cells to understand how they are regulated. The inventors performed a proof of principle experiment of single cell alternative splicing using barcoded FISH on the S. cerevisiae gene PTC7. The PTC7 gene is composed of an intron flanked by two exons (FIG. 8a). Two isoforms of the PTC7 mRNA exist in cerevisiae. The intron is retained in the unspliced isoform, and the protein produced from it is localized to the cell membrane. In contrast, the spliced version of PTC7 is localized to the mitochondria. The inventors designed probe sets that would hybridize to the intron of PTC7 and the second exon. The four intronic probes were conjugated to Cy5; four of the exonic probes were conjugated to Cy3 and another four were conjugated to Alexa 594. When Cy3 and Alexa 594 colocalized without Cy5, it correspond to the spliced mRNA isoform (FIG. 8d). Conversely, if all three dyes co-localized, that correspond to the unspliced mRNA isoform (FIG. 8c). Upon analysis of the images (FIG. 8b), the inventors were able to determine the number of each type of mRNA isoform in individual cells (FIG. 8e). The general hybridization efficiency of the probes suggests that the presence of the intronic region labeled with 4 probes can be detected with 99% confidence. In addition, centroid fitting can be used to read out the spatial ordering of the probes (FIG. 8 c,d and FIG. 23).

The inventors observed that on average 17.3% of the transcripts were unspliced (N=98), consistent with the 13.3% determined from qPCR. However, at the single cell level, the efficiency of splicing is heterogeneously distributed across cells (FIG. 8e): some cells contain only spliced transcripts while others contain equal amounts of the spliced and unspliced isoforms. The efficiency of splicing is not dependent on the total transcript number and is not uniformly distributed, indicating heterogeneities in the splicing machinery. Recent techniques also used FISH to detect alternatively spliced transcripts in single cells with a resolution of 1-2 kilobase. The inventors approach is applicable to most exons because of its shorter nucleotide resolution. In addition, with spatial resolution, the super-resolution approach provides the foundation to image combinatorial splicing events on the same transcript, which are crucial for transcripts with multiple splice junctions involved in processes such as neuronal patterning and tumorigenesis.

Example 9

Super-resolution Imaging of mRNA Barcodes

Figure 17:
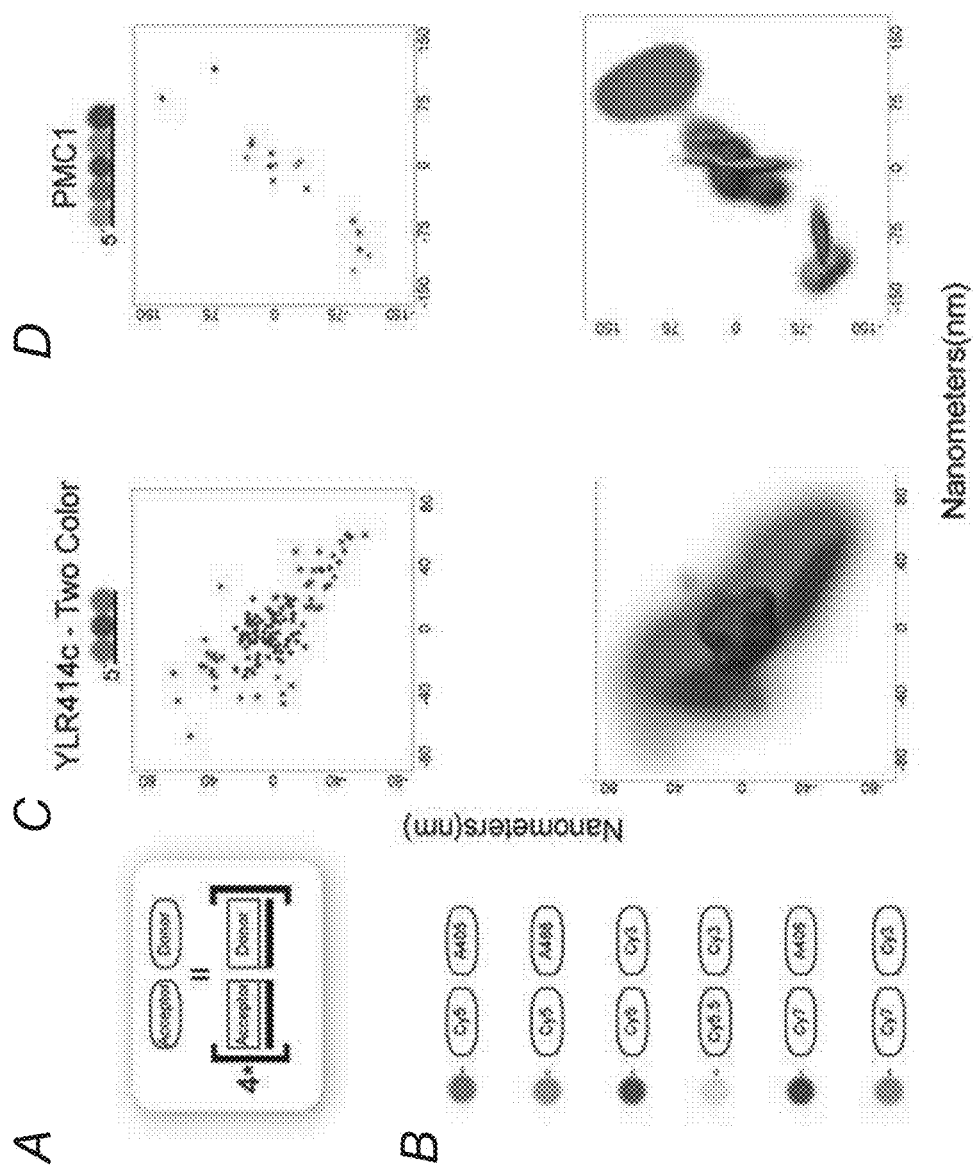
FIGS. 17A-E depict, in accordance with an embodiment of the invention, STORM reconstructions associated with FIG. 7. A) For each dye pair, four acceptor/emitter pairs are hybridizied in sequence for redundancy. B) Each barcode color consists of an activator (Alexa 405, 488, and Cy3) labeled oligo adjacent to a 5' emitter (Cy5, Cy5.5 and Cy7) labeled oligo. The order of the probes is shown schematically in the cartoon. A histogram of the STORM reconstruction of a single barcode is shown along with the localization scatterplots in which each dot represents an activation of STORM fluorophores. C) YLR414c mRNA, repeat 2 color barcode. Note the correct localizations of two identical but spatially separated red sections. D) 5 position barcode on PMC1 mRNA. E) Reconstructions of YLR414c 3 color barcodes from one cell. The correct barcode order is Red-Green-Blue.
Figure 17:
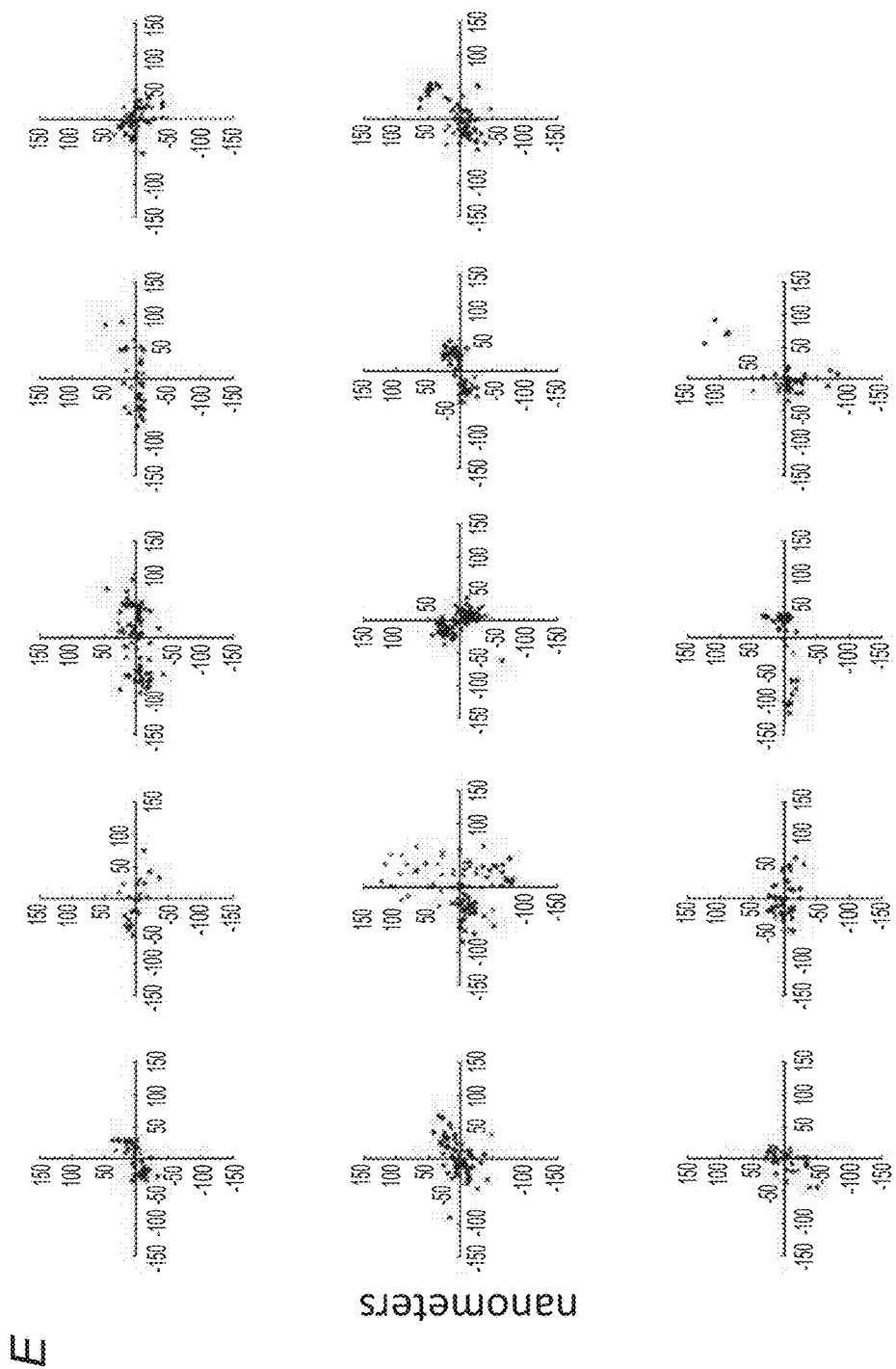

Conventional fluororescence microscopy is only useful in cases where transcript levels are low. When the density of transcripts is high, diffraction-limited fluorescent spots will overlap and make barcode readout by centroid fitting impossible. Super-resolution imaging is essential for single-cell microscopy to achieve high-density multiplex barcoding. The inventors turned to the Cyanine dye based photoswitchable dye pairs developed by Bates et al (as cited above). In the PALM, STORM, and FPALM implementations of SRM, subsets of fluorophores are photo-activated, imaged as single molecules, localized by centroid fitting and switched off. After many iterations of this cycle, a high-resolution image can be reconstructed from all of the centroid fits in the individual images. The inventors exploited the pairs of fluorophores used by STORM microscopy to dramatically reduce the background from non-specifically bound probes. The STORM scheme places an activator dye in close proximity to a Cy5 emitter, which can be switched off by imaging and re-activated by exciting the activator, as described in greater detail above. The inventors designed the oligos such that two probes were used: one labeled at its 3' position with the activator and the other at the 5' position with the emitter (FIG. 9a). The probes were designed to hybridize on the mRNA at adjacent positions separated by 2 bp, bringing the dye pairs within 1 nm. This labeling scheme has several advantages: it avoids the uncontrollable non-specific blinking of covalently linked dye pairs and also increases labeling specificity. As both probes were required for the fluorophore to be re-activated, the background from non-specifically bound Cy5 probes in the cell was reduced because these probes do not reactivate. Cy5.5 and Cy7 can also be used as emitters in conjunction with Cy5 (FIG. 9b). Using 3 activators and 3 emitter dyes, a total of 9 distinct dye pairs or colors are available. Using more activators and emitters, more dye pairs or colors are available, as described herein. With this large pool of fluorophores, two schemes of barcode labeling are possible: spatial and spectral, each with advantages and disadvantages. In the spatial coding scheme (FIG. 9a,b), as shown previously with conventional fluorophores, different regions of mRNA are labeled with different super-resolution fluorophores which generates a spatial sequence that can be readout. As an example, a three-position spatial barcode (FIG. 9) can be reconstructed correctly 72±10% (N=50). This rate is independent of mRNAs species (FIG. 9 a,b) and consistent with the reconstruction rate of conventional fluorophores. The advantage of this coding scheme is that it scales up easily in principle, as the amount of unique spatial labels grows geometrically with the length of the barcode. A 5 position coding scheme (FIG. 17) can potentially code the entire transcriptome ($9^5/2=29525$). However, in practice, throughput is restricted to ~1000 genes by the photophysical properties of the fluorophores. In addition, as the spatial barcoding requires stretching out mRNAs, it is only applicable to systems where cells can be compressed. In many biological systems, such as biofilms or tissue cultures, compression would destroy the morphology of the sample. Alternatively, using DNA origami and self-assembly has potential for generating ordered barcodes, although it is not without its challenges, as described in the foregoing discussion regarding the same.

As demonstrated by the previously described experiments, the spectral barcoding scheme is immediately applicable and robust with current technology. In spectral barcoding (FIG. 9 c,d) the identity of mRNA is coded for by the combination of fluorophores, ignoring the spatial ordering. As long as all the colors are present, the identity of the mRNA can be determined. Spectral coding allows fluorophores of a single color to be distributed throughout an mRNA, making it more robust to heterogeneities in hybridization. As long as single dye pairs of each color can be identified above the cross-talk tolerances, the barcode assignment can be confidently made even if the amount of collected photons is low. The resolution requirement of spectral coding is satisfied as long as individual mRNAs can be resolved from their neighbors. Since the average size of the reconstructed barcode is 100 nm, a typical yeast cell with a diameter of 5 um can readily accommodate 100,000 barcodes, sufficient to accommodate most transcripts in yeast. In comparison, spatial coding has more stringent resolution requirements because order must be readout within an mRNA. Since spectral coding does not require the labeled molecule to be linear, it can be used generally in biological samples without the need for compression. Molecules that cannot be easily stretched out or with unknown structures, such as proteins, can also be labeled spectrally in a similar fashion.

The disadvantage of the spectral coding scheme is its low multiplex capacity. However, using just 9 dye pairs, a 4 position spectral coding scheme allows $_9C_4=126$ genes to be multiplexed at the single cell level. This scheme scales exponentially with the number of fluorophores available. As indicated in Dempsey et al., "Evaluation of fluorophores for optimal performance in localization-based super-resolution imaging" Nat. Methods. 2011 Nov. 6; 8(12):1027-36, which is incorporated herein by reference in its entirety as though fully set forth, at least one additional emitter is available to pair with the activators, giving at least 3 additional SRM fluorophores. With just one additional emitter, close to a thousand genes ($_{12}C_5=792$) can be multiplexed in single cells.

In fact, recent studies indicate that using the above-described scheme, for activators there are at least 4 choices, including Alexa 405, 488, 532 and 568, and for emitters, there are also at least 4 choices, including Cy5, Cy5.5, Cy7, and 7.5. With these choices, because they can be mixed and matched to give functional dye pairs, there are 16 possible pairs (4×4) in all. Recent studies also indicate that the particular characteristics of these molecules can influence their suitability for specific applications. For example, for RNA FISH particularly good emitters are Alexa 647 or Dynomics 632, Cy5.5, Cy7, and IR800CW. For DNA FISH, they are Alexa 647, Cy5.5, Alexa 750 and Alexa 790.

When the activators and emitters described directly above are considered, a much easier 2 color barcode can get to the same multiplex capacity ($_{16}C_2=120$) described above. In fact, the inventors have used this method for the analysis of almost 100 genes.

Example 10

Combinatorial Regulation of Transcriptional Bursts in the Calcium Response Pathways It has been recently observed that many transcription factors (TFs), particularly those involved in stress responses, activate gene expression in discrete pulses. These TF pulses occur in a wide range of organisms, such as SOS in bacteria, Msn2 and Crz1 in budding yeast, and p53 and NF-kB in mammalian cells. Since many of the pulses occur stochastically in single cells and are averaged out in population experiments, the inventors set out to determine if pulsing in many of the stress response genes is correlated and in doing so to ascertain their modes of combinatorial regulation by upstream TFs. The inventors hypothesized that co-regulated genes are more likely to bursts together. By sampling many stress response genes using super-resolution barcode imaging, the correlations amongst the single cell gene expression patterns can be used to infer regulatory architectures.

The calcium signaling pathway in budding yeast is an ideal model to address these questions. The inventors have previously shown that in response to external signals, the master transcription factor Crz1 translocates in and out of the nucleus in short (2-3 minute) well-defined pulses. These pulses occur stochastically in time and involve most of the Crz1 molecules in the cell. In addition to Crz1, calcium stress also triggers the Msn2 pathway, a general stress response regulator that also pulses in its localization. To ensure that they were observing the products of individual TF pulses, the inventors fixed cells under conditions where the average interval between pulses was longer than the typical mRNA lifetime. This experiment necessitated the application of the inventive barcoding technique as it is difficult to multiplex more than 10 genes with existing single cell techniques, and population measurement would have been averaged over the unsynchronized Crz1 pulses in different cells. The inventors' technique provides a unique snapshot of expression of a battery of stress response genes.

The inventors selected 14 genes that are regulated by Crz1, 5 general stress response genes, as well as 13 other aging and stress markers, for a total of 32 genes. To label these genes, the inventors used spectral coding of combinations of 3 out of 7 super-resolution dye pairs ($_3C_7=35$). Barcode assignments are shown below in Table 2. Codes 135, 235, and 895 are left empty. In the barcode scramble experiments, the activators are permuted. 1->2, 2->3, 3->1.

TABLE 2

Barcode Assignments

| Crz1 Genes | | Aging and Stress Genes | | Msn2 Genes | | Number Key |
|---|---|---|---|---|---|---|
| YLR414c | 123 | cta1 | 179 | ctt1 | 137 | 1 - 405 cy5 |
| YLR194c | 239 | dpp1 | 125 | hsp30 | 238 | 2 - 488 Cy5 |
| cmk2 | 789 | duh1 | 795 | pgm2 | 237 | 3 - Cy3 Cy5 |
| pmc1 | 389 | esa1 | 895 | sit4 | 138 | 5 - Cy3 Cy5 |
| cos1 | 127 | fbp1 | 157 | uip2 | 129 | 7 - 405 Cy7 |
| mep1 | 289 | fth1 | 158 | | | 8 - 488 Cy7 |
| npt1 | 189 | ino1 | 159 | | | 9 - Cy3 Cy7 |
| put1 | 378 | mls1 | 257 | | | |
| yps1 | 379 | pck1 | 258 | | | |
| sok2 | 279 | phr1 | 259 | | | |
| gyp7 | 278 | prb1 | 785 | | | |
| aro10 | 178 | rad51 | 358 | | | |
| doa1 | 128 | rck1 | 359 | | | |
| rcn2 | 139 | | | | | |

Figure 10:
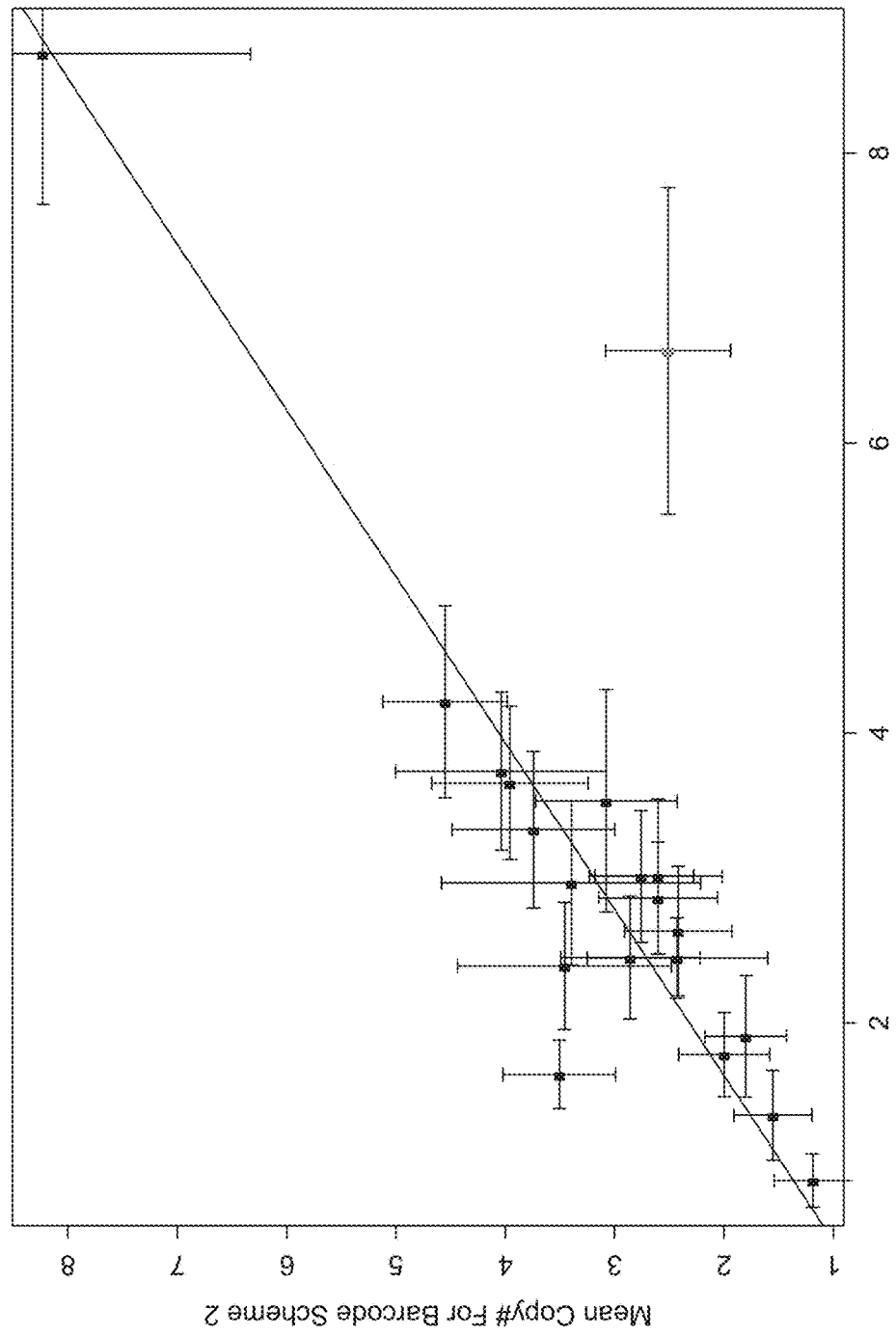
FIG. 10 depicts, in accordance with an embodiment of the invention, robustness of mRNA quantitation measured by two different barcode schemes. For twenty genes, the barcodes were scrambled so the same pool of fluorophore combinations would be applied to different genes. Mean copy-number measurements for barcoding schemes are displayed in the scatterplot along with error-bars obtained by bootstrap resampling. A regression with an $R^2$ value of 0.88 was obtained following removal of the one outlier connoted in red. The outlier was removed due to its high Cook's distance of 2.08226. These measurements indicate that spectral barcoding, regardless of the scheme used, accurately and robustly measures the copy numbers of mRNA in single cells.
Figure 18:
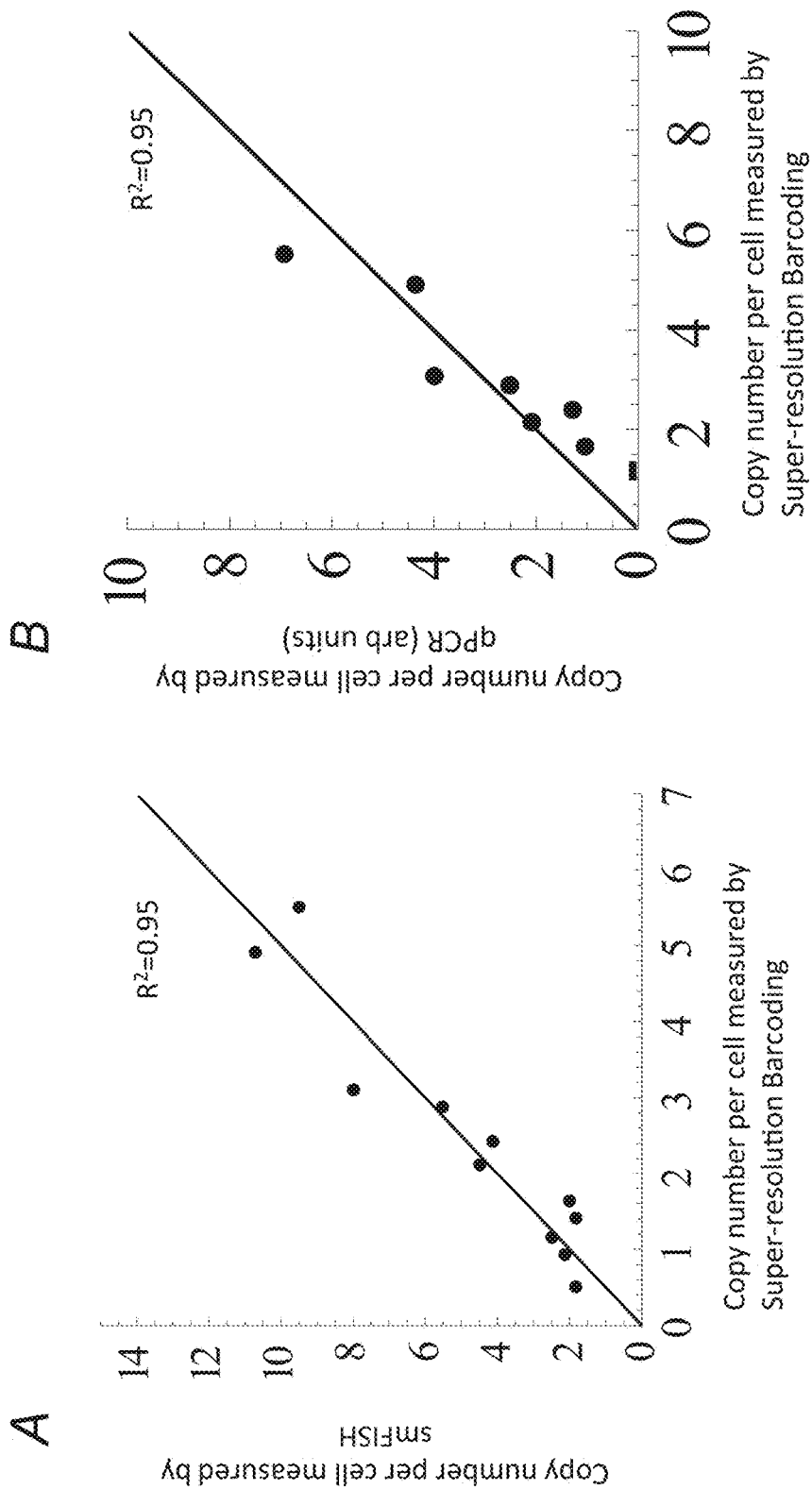
FIGS. 18A-G depict exemplary embodiments of the invention, and are associated with FIG. 10. Comparison of mean expression level measured by super-resolution barcoding vs smFISH (A) and qPCR (B). smFISH is performed with 12 probes. The mean copy number is determined from averaging over a sample size of >50 cells for each gene. The 2 fold difference observed between the super-res barcoding and smFISH results was likely due to the loss of the barcodes from poor hybridization. In total, 11 genes were FISHed, including 8 crz1 specific genes, 1 Msn2 target genes, and 2 aging and stress genes. In the qPCR experiment, 8 Crz1 genes were quantified. C) Reconstructions of barcode labeled mRNAs in single cells. Each pixel corresponds to 130 nm. The right panel shows a zoomed plot of a region in the cell. Each mRNAs is shown in boxes. D-G depict barcode crosstalk measurements. 3 color barcode is hybridized and imaged. The leakage of that barcode into other barcodes is shown on the histogram, representing the errors in detection and analysis. A total of 20 cells are counted in each case. D) a barcode with cy5 emitters and all 3 activators, hybridized against YLR414c. E) The worst case scenario, with Cy3 activators and all emitters hybridized against YSP1 which is present at lower abundances than YLR414c. Because Cy3 can be activated by 405 and 473 nm lasers, there is more crosstalk into those channels. It was observed that there is a relatively low uniform background of barcodes observed due to autofluorescence in the cells and nonspecific blinking events. This background is additive to the barcode quantitation and does not scale with the copy number of the genes. F-G) Single dye pair crosstalk ratios. 12 probe pairs are hybridized against YLR414c coupled with each combination of fluorophores. Then the false activation rate in different STORM channels are measured for Cy5 (F) and Cy7 (G) emitters with the inventors' full imaging routine. Crosstalk from Cy3-Cy5 into Cy4-Cy5.5 is 11.6% and negligible in the reverse direction.
Figure 18:
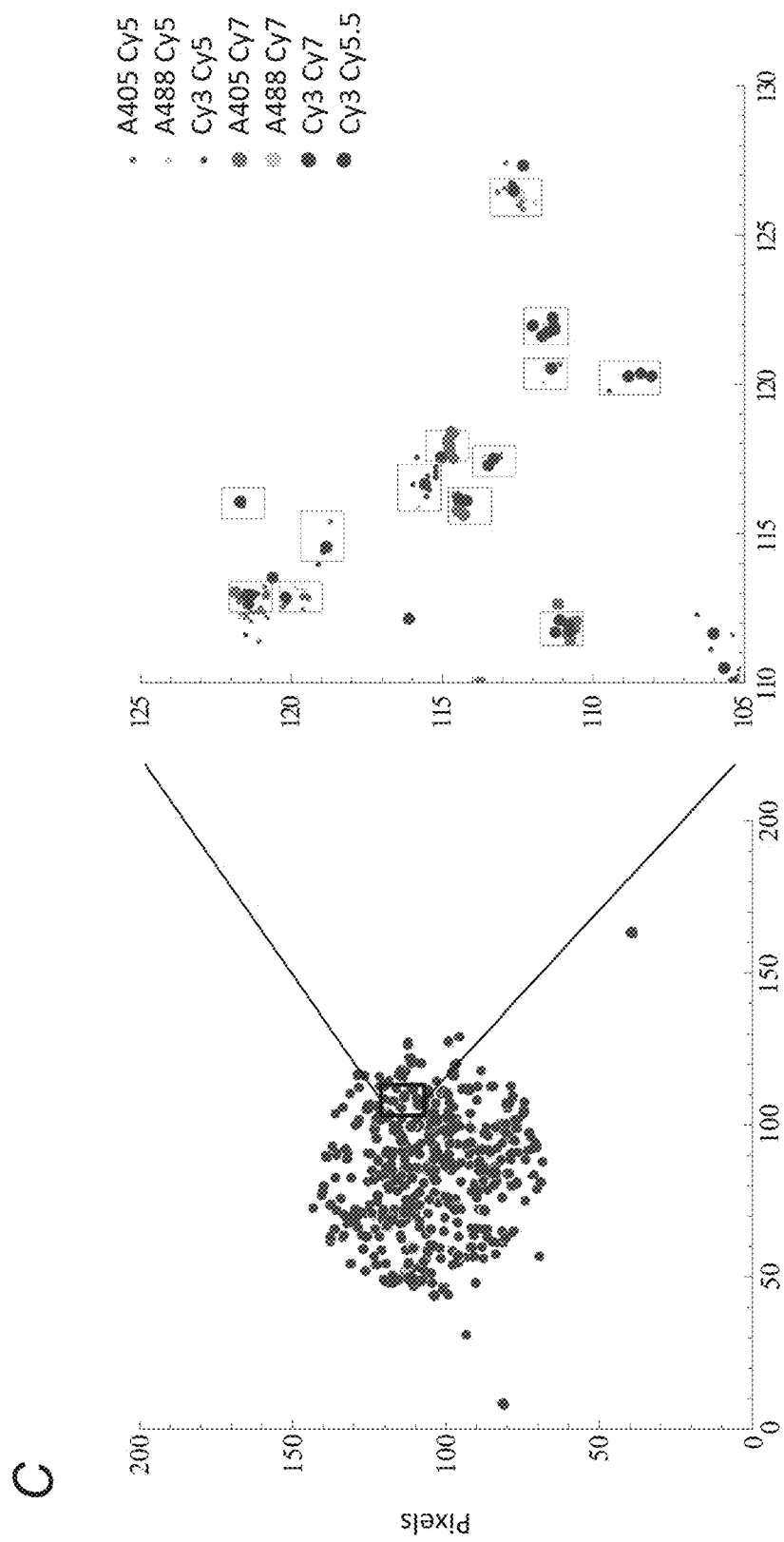
Figure 18:
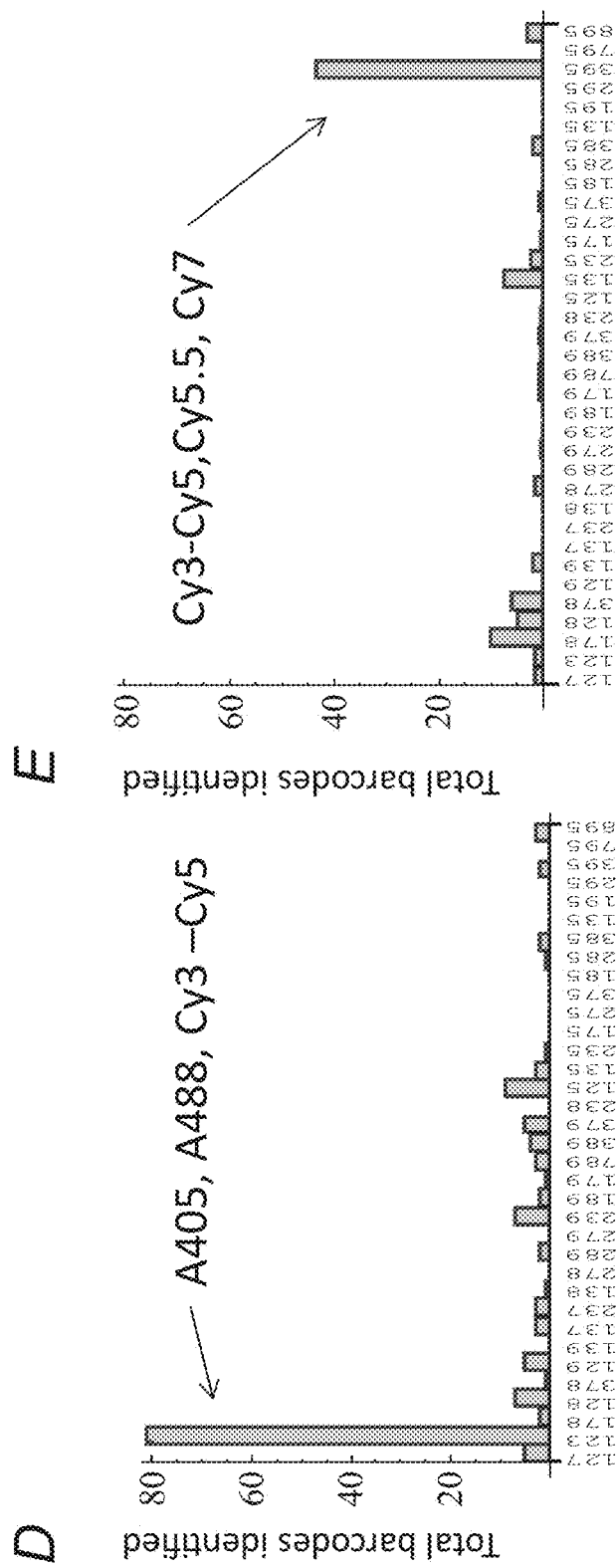
Figure 18:
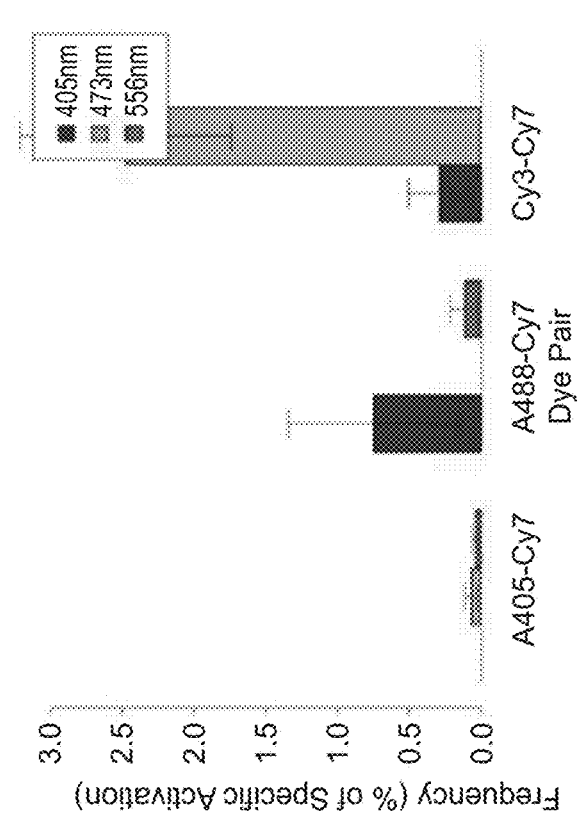
Figure 18:
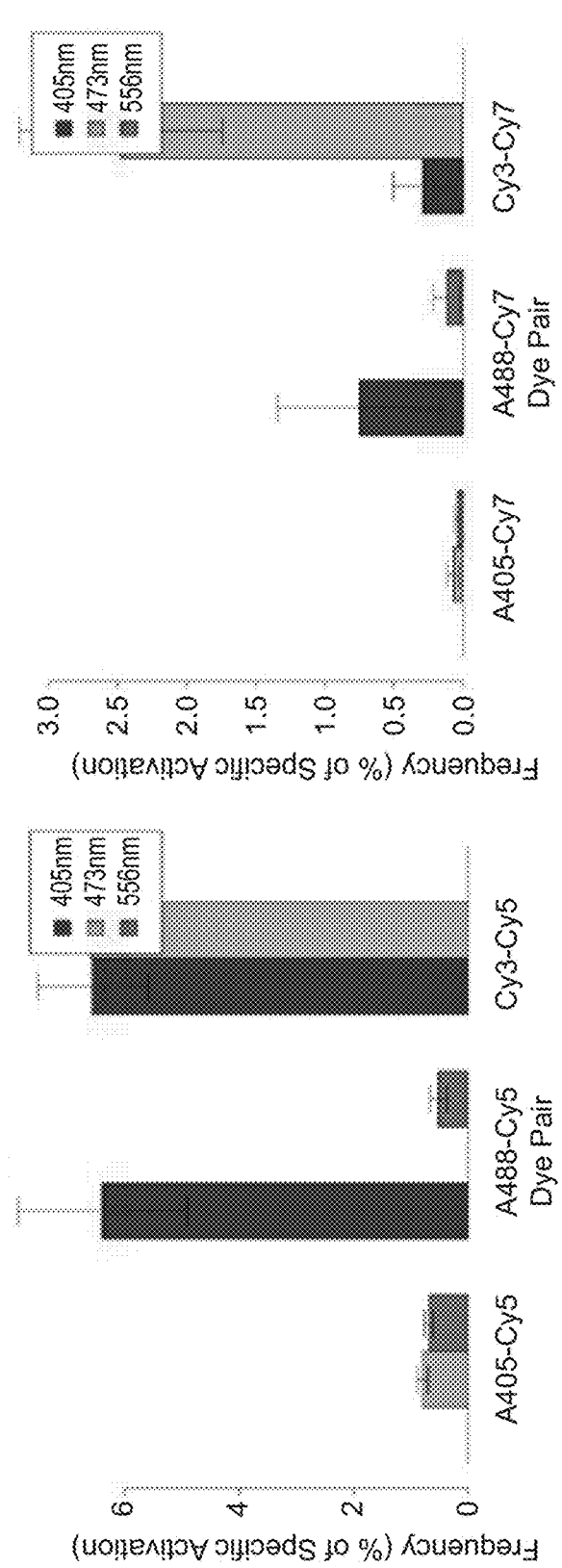

Cells were imaged by super-resolution and transcript levels in individual cells quantified based on the abundances of the corresponding barcodes. All genes were assigned barcodes containing combinations of 3 fluorophore pairs. The main concern with multiplexing a large probe set is the crosstalk among the barcodes. This can arise from several sources: fluorescent background from the cell, blinking of nonspecifically bound probes, crosstalk in the fluorophores, and errors in computation analysis. The inventors controlled for each of these sources of errors (FIG. 18). To rule out crosstalk and non-specific blinking, the inventors thresholded the fluorophores in the clusters so only colors at least more than 3 standard deviations from the measured one color crosstalk values were counted (FIG. 18). To determine if there was significant bias introduced by a particular barcode scheme, the inventors compared the expression levels of a set of 20 genes measured by 2 different scrambled barcode schemes (Table 2). The two measurements agreed with an $R^2=0.88$ (FIG. 10) in 19 of the 20 compared genes. This tight correlation indicates that there is no significant source of bias in the measurements either in endogenous background or photophysical properties of dyes. To check the accuracy of barcode quantitation independently, the inventors compared the mean expressions level with qPCR as well as single molecule FISH measurements, and obtained $R^2=0.95$ and $R^2=0.95$, respectively (FIG. 18).

Figure 19:
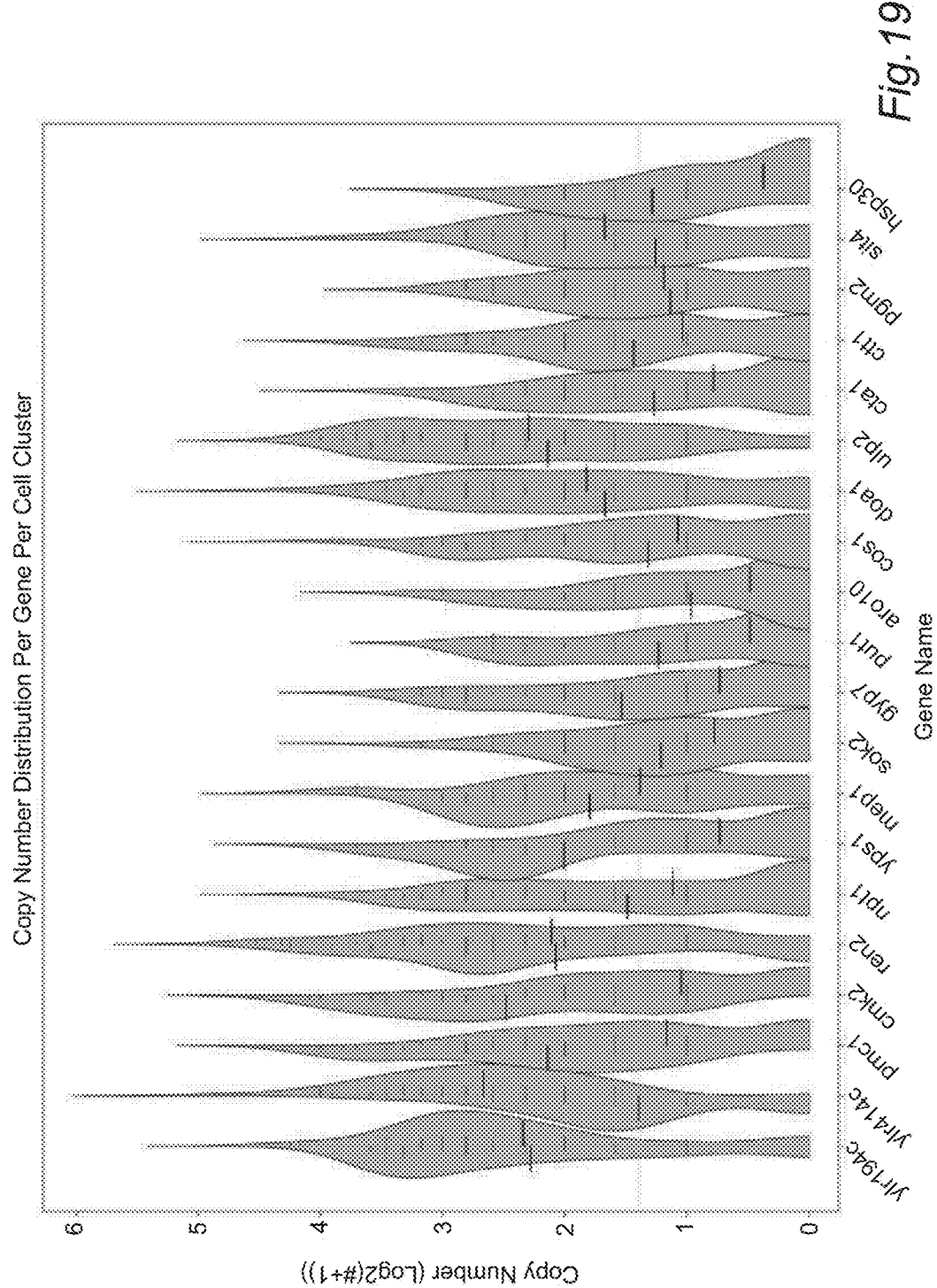
FIG. 19 depicts, in accordance with an embodiment of the invention, distribution of expression levels for each Crz1 and Msn2 gene. Expression levels are shown in log 2(#+1) value Bean plots. For each gene, two distributions are shown. On the left are the single cell expression profiles in cluster 2: cells with only the combinatorial targets active. On the right are the distributions for that gene in cell cluster 1: cells with all Crz1 target genes on. Black lines indicate the mean values of the distribution. Blue lines mark the integer number of transcripts.
Figure 20:
FIGS. 20A and B depict, in accordance with an embodiment of the invention, pairwise correlations of genes in single cells. X and y axis are in copy number per cell. 2D scatterplots are of pairwise copy number distribution in cells. Cells from cluster 1 are shown in red and cluster 2 shown in green. The corresponding correlation coefficient is shown in the diagonal box.
Figure 20:
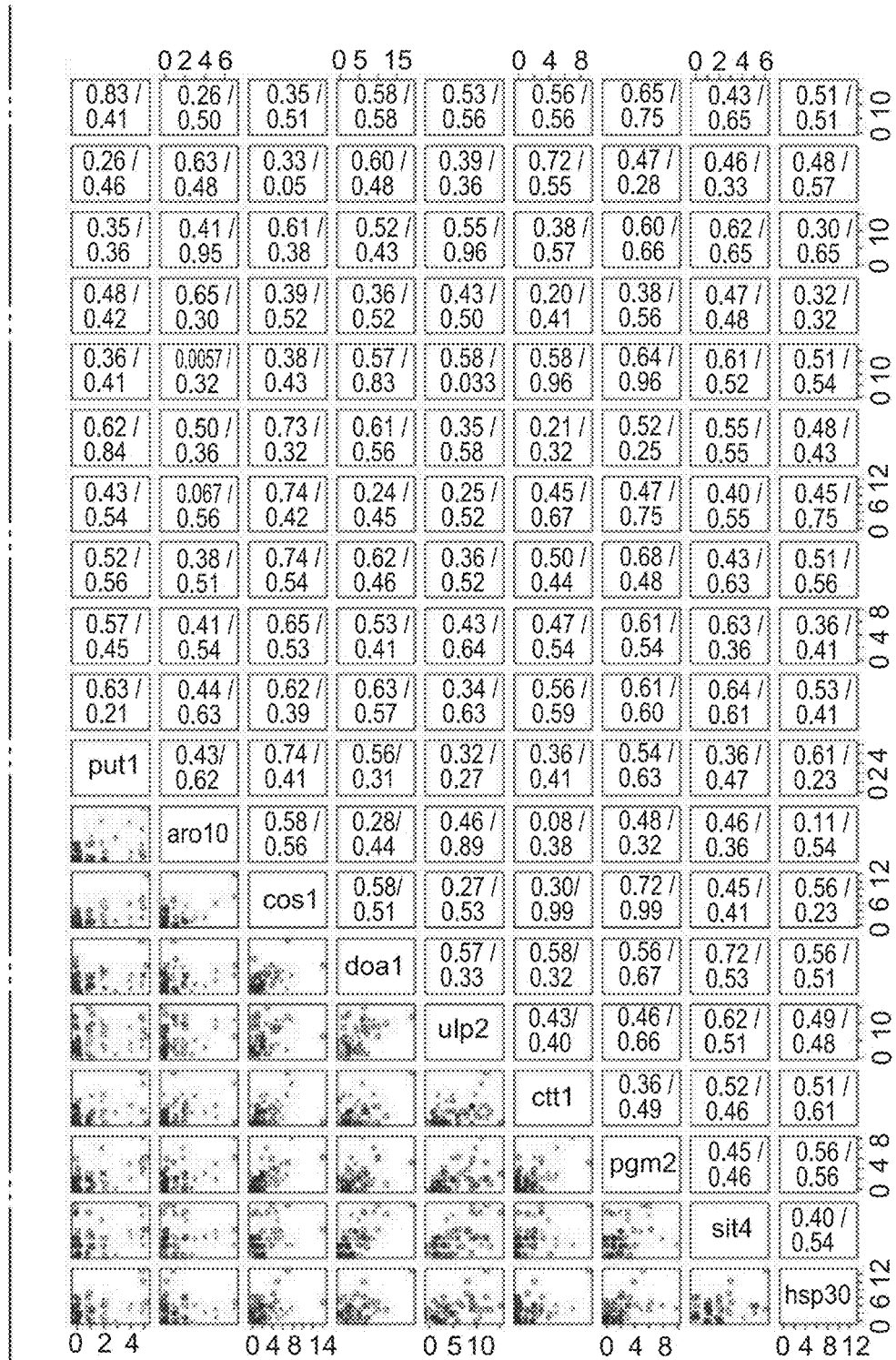

With the single cell data (FIG. 11), the inventors first asked whether bursting amongst the different target genes is correlated. For most genes, the distribution of expression levels included a low basal state and a long-tailed high-expression mode corresponding to transcriptional bursts (FIG. 19). However, in many cells, certain Crz1 genes were highly expressed with a copy number of 20-30 mRNA molecules per cell, while others were not expressed at all (FIG. 20). This suggests that despite a large nuclear concentration of the Crz1 TF during a pulse, not all of the target promoters can respond. To look at the level of coordination among all Crz1 target genes, the inventors examined how frequently a given number of genes burst simultaneously. The inventors found that the level of coordination amongst genes is widely distributed, with the probability of finding only a few of the target genes bursting as likely as finding most of the Crz1 genes ON (FIG. 12a).

Figure 11:
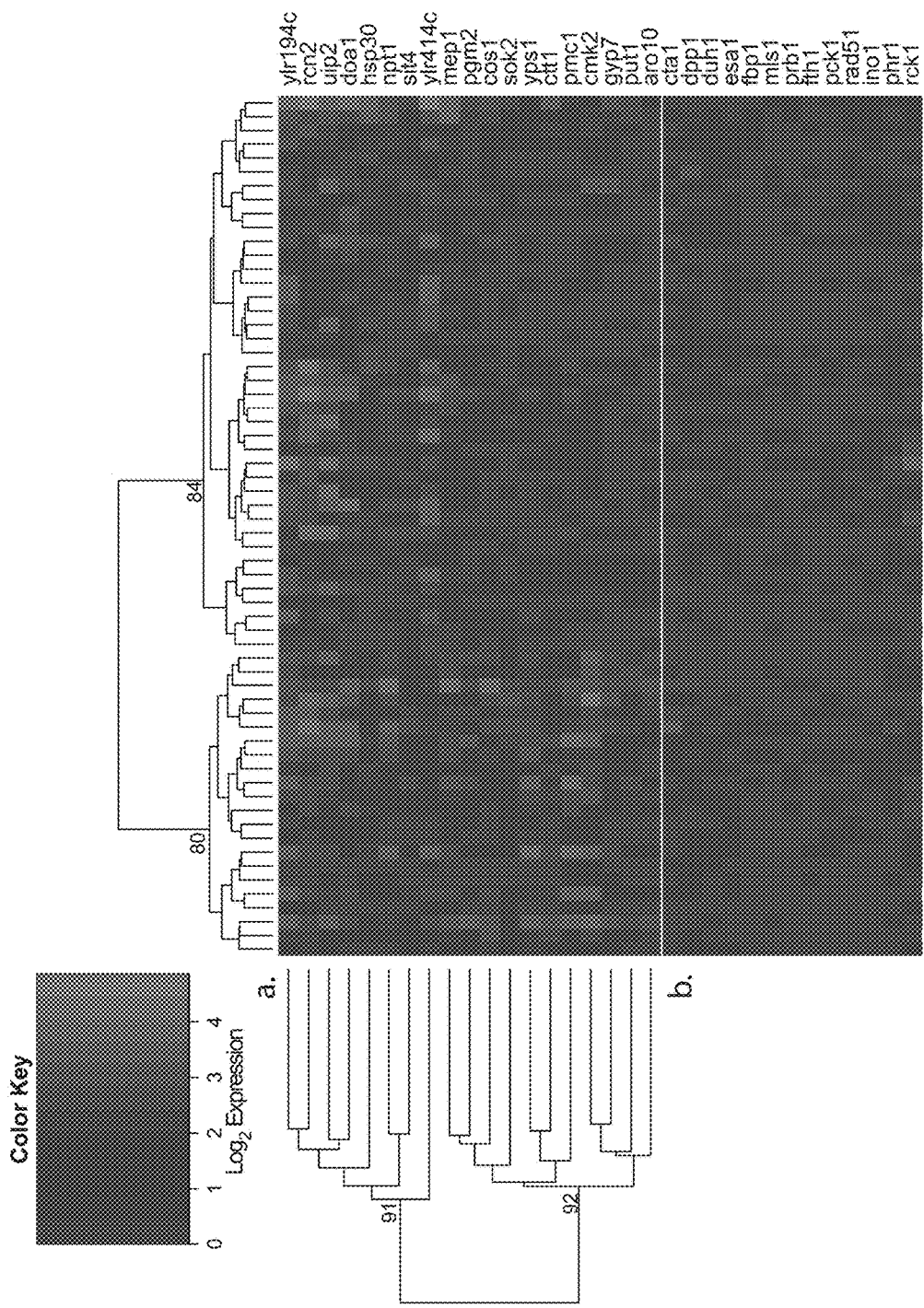
FIGS. 11A-B depict, in accordance with an embodiment of the invention, single cell expression profiles of 32 mRNAs. Cells, and genes in part (A) are clustered using agglomerative hierarchal clustering on the correlation between species using Ward's criterion. A) Genes responsive to Crz1 and Msn2. Genes can be broadly clustered into two classes, one largely containing genes regulated by both Crz1 and Msn2 (p=0.09, upper cluster) and one largely containing genes regulated by Crz1 (p=0.08, lower cluster). Cells are grouped in two distinct clusters, one showing correlations amongst the expression of all genes regulated by Crz1 (p=0.2, left cluster), the other with large expression correlations amongst combinatorial genes (p=0.16, right clusters). B) Additional measured genes are shown. No significant pattern was found in their expressions.
Figure 21:
FIGS. 21A-C depict, in accordance with an embodiment of the invention, heat maps of single cell gene expression levels under different conditions. This figure is associated with FIG. 11. In all figures, the cells are treated with 50 mM $CaCl_2$. The combinatorial genes are plotted in the upper half of the figure. A) fk506 treated cells. Combinatorial targets are active while the pure Crz1 targets are inactive, indicating non-Crz1 inputs can drive combinatorial target expression. B) Msn2/4 deleted cells. Most cells show coordinated expression among Crz1 and combinatorial target genes, suggesting that Msn2 is the major factor in driving heterogeneous expression of combinatorial genes from pure Crz1 genes. C) Crz1 over-expressed cells. A greater level of coordination is observed when Crz1 is up-regulated 50-100 fold. However, heterogeneous bursting patterns are still observed, indicating the presence of additional rate-limiting processes in transcriptional activation beyond TF concentration.
Figure 21:
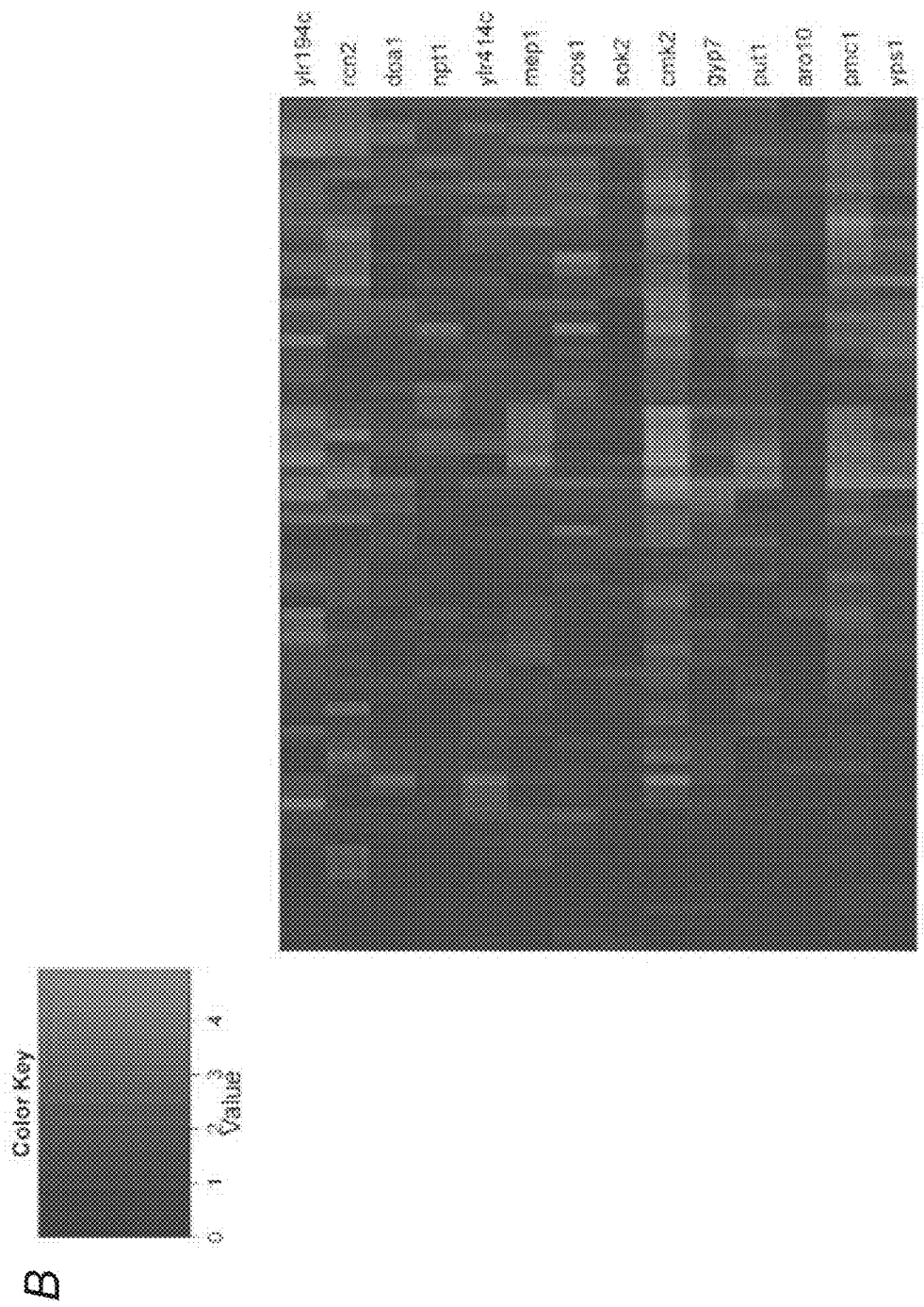
Figure 21:
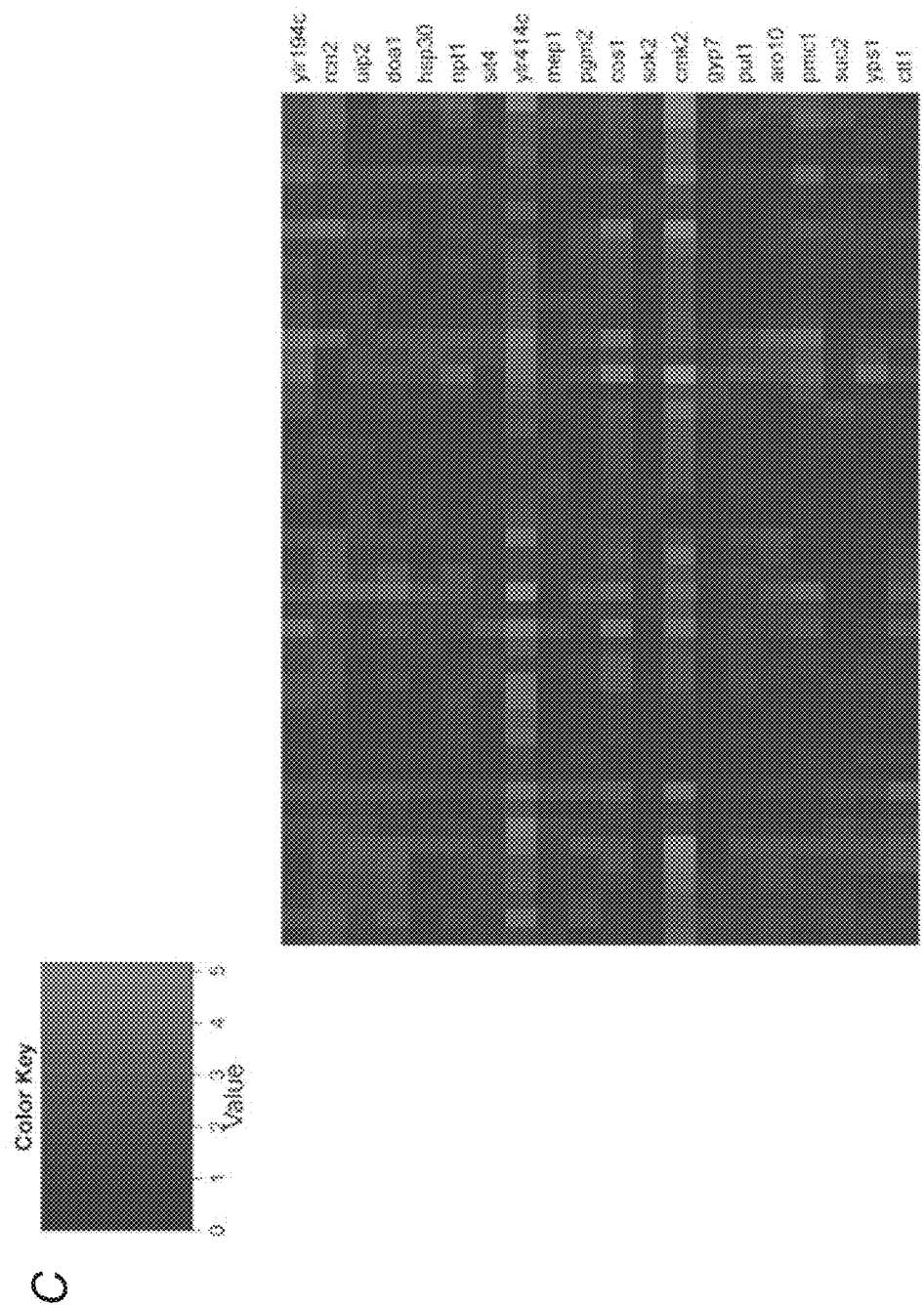
Figure 25:
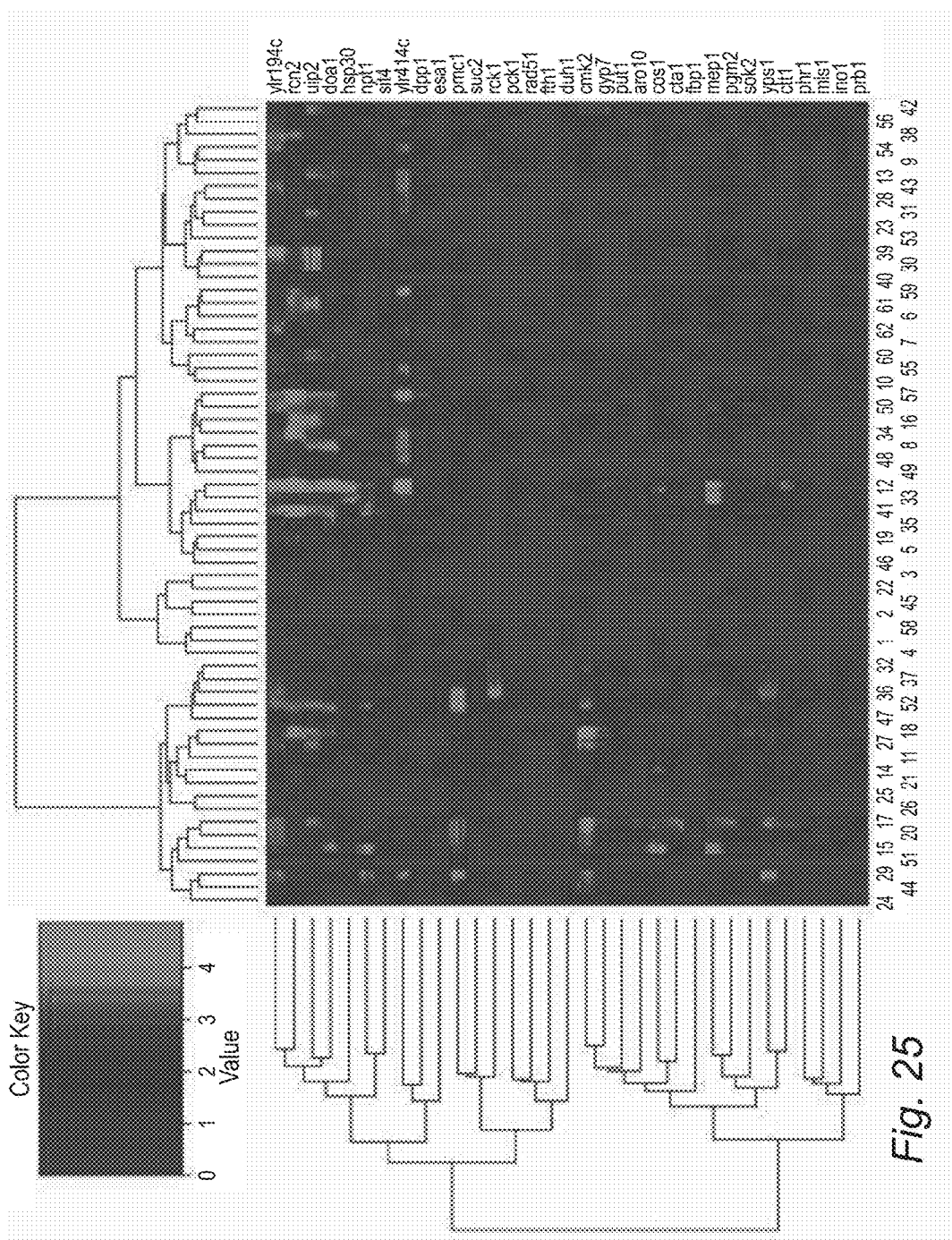
FIG. 25 depicts, in accordance with an embodiment of the invention, clustering with the aging genes included. The same two clusters of pure and combinatorial Crz1 target genes are preserved. Aging and stress genes roughly fall into 2 separate clusters, apart from the Crz1 and Msn2 genes.

The inventors next asked whether there are subgroups of the Crz1 genes that tend to burst together and whether they correspond to different regulatory architecture. By agglomerative hierarchal clustering with Ward's criterion of the correlation distances between genes, the inventors resolved two distinct clusters for the Crz1 responsive genes with high p values (0.09, 0.08) (FIG. 11). In the first cluster, Crz1 genes were preferentially clustered with Msn2 genes. The promoter sequences of these genes, such as YLR414c, YLR194c, Rcn2, Npt1 contains Msn2 binding sites along with Crz1 binding sites. At the same time, genes in the other cluster contain predominantly only Crz1 binding sites, with the exception of Yps1 and Pmc1 which also contain Msn2 sites. The inventors noted that when they included the aging and stress genes in the clustering, the Crz1 and combinatorial genes largely remained in distinct clusters (FIG. 25). Given that pure Crz1 and combinatorial target genes have different expression patterns, the inventors asked whether the combinatorial genes were bursting in response to other inputs, such as Msn2, in addition to Crz1 pulses. The inventors observed that in many cells, both pure and combinatorial genes were bursting, while in a different subset of cells, only the combinatorial targets were bursting. The inventors did not observe cells that had only pure Crz1 genes on, but no combinatorial genes. The inventors have previously shown that both Crz1 and Msn2 pulse in response to calcium stress, but their pulses were not synchronized in individual cells. Thus, it is likely the inventors were observing transcripts produced when either TFs were present in the nucleus, but rarely when both are co-localized, since the frequency of both pulses are low at 50 mM calcium. The inventors hypothesized that cells bursting only in the combinatorial targets are products of Msn2 pulses, while cells with all Crz1 genes on are generated by Crz1 pulses. To test this hypothesis, the inventors knocked out Crz1 and Msn2 pathways separately. The inventors observed that in cells treated with FK506, an inhibitor of the Crz1 phosphotase Calcineurin, only combinatorial genes were expressed at non-negligible levels (FIG. 21). On the other hand, in the Msn2/Msn4 deletion cells, the combinatorial genes pulse coordinately with pure Crz1 genes (FIG. 21). While not wishing to be bound by any one particular theory, these experiments suggest that Msn2 is a significant input to generate additional pulsing from these combinatorial promoters.

Figure 12:
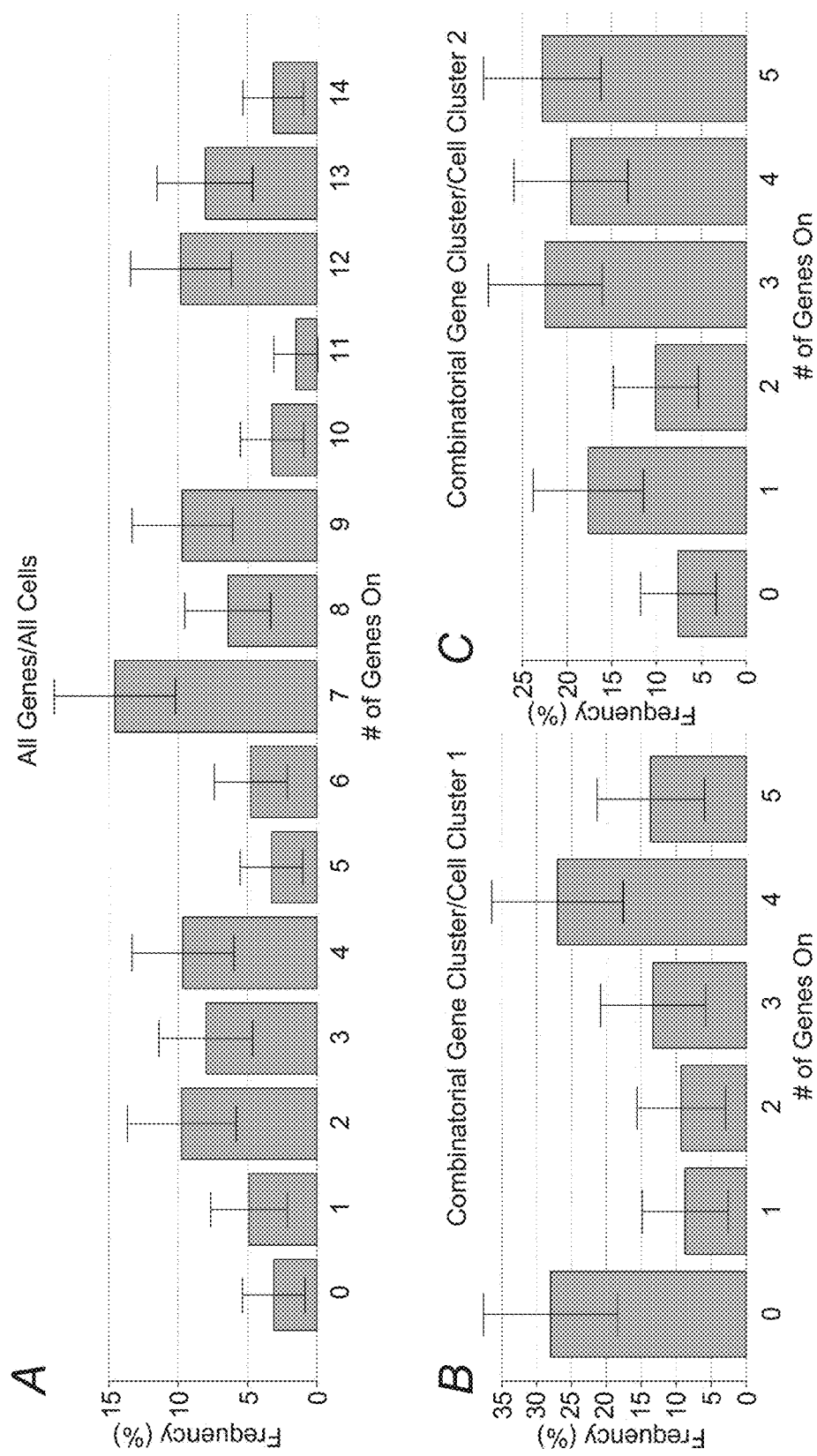
FIGS. 12A-E depict, in accordance with an embodiment of the invention, coordination of transcriptional bursts in the Crz1 regulon. Cells and genes are grouped into the clusters defined in FIG. 11. Genes are defined as bursting if their expression is above the mean expression level. Error bars were obtained by bootstrap resampling. A) All Crz1 genes/ all cells. A wide range of coordination in bursting is observed in cells induced with 50 mM $CaCl_2$. B-E) Coordination in distinct gene and cell clusters. Combinatorial and pure Crz1 targets are observed to be similarly coordinated within the clusters that they are active. The second cluster of cells with only combinatorial genes active is likely the product of Msn2 pulses.
Figure 12:
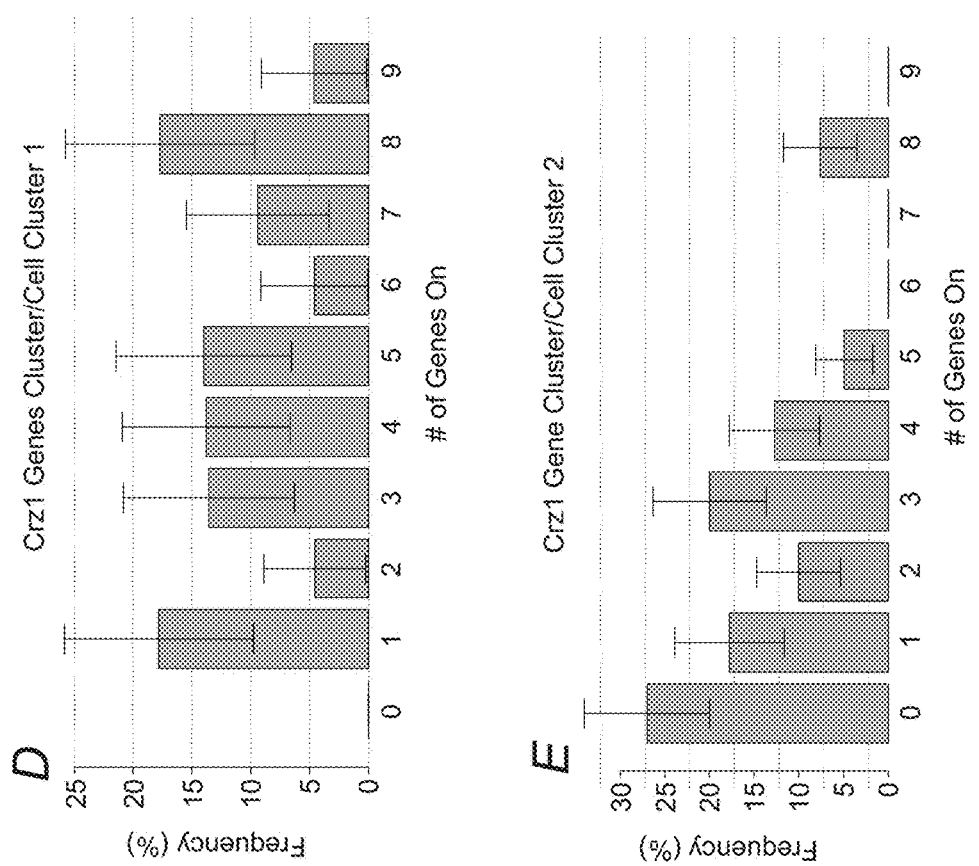
Figure 13:
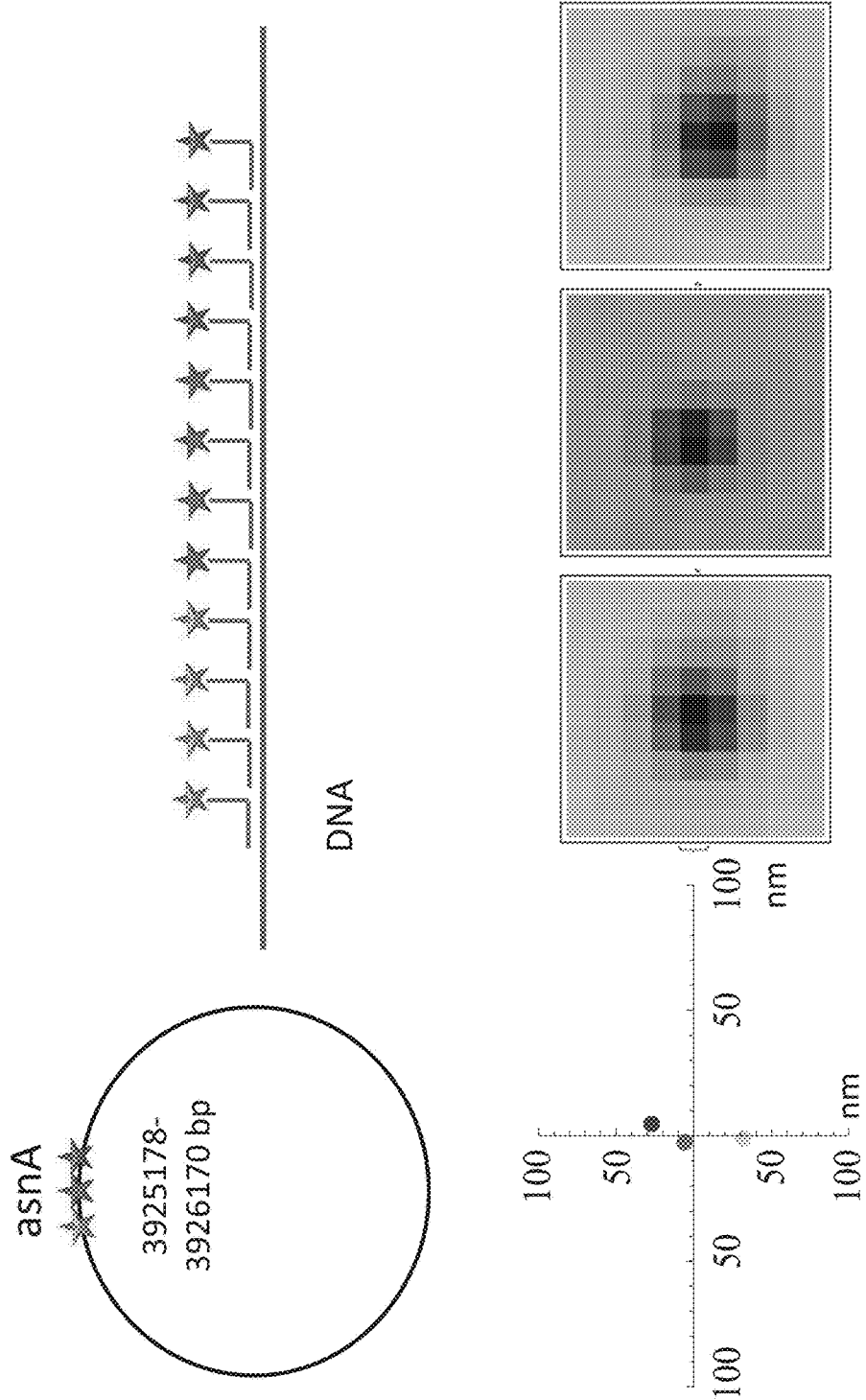
FIG. 13 depicts, in accordance with an embodiment of the invention, barcode labeling of the asnA chromosome locus in E. coli.
Figure 14:
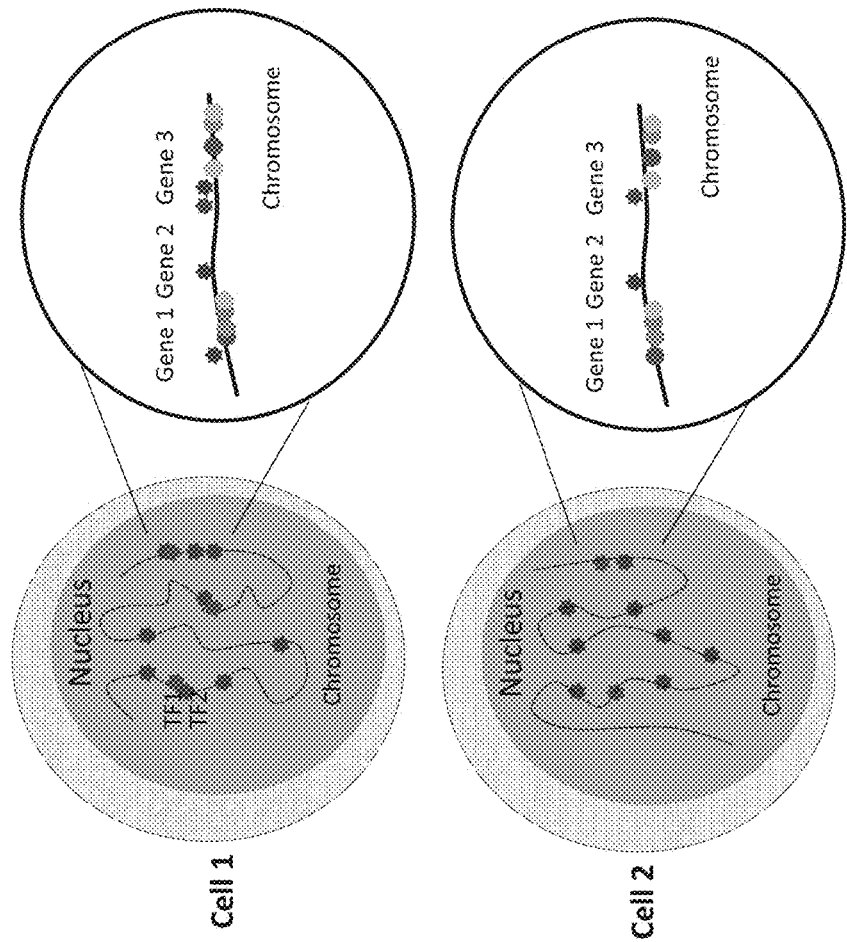
FIG. 14 depicts, in accordance with an embodiment of the invention, single cell ChIP.
Figure 15:
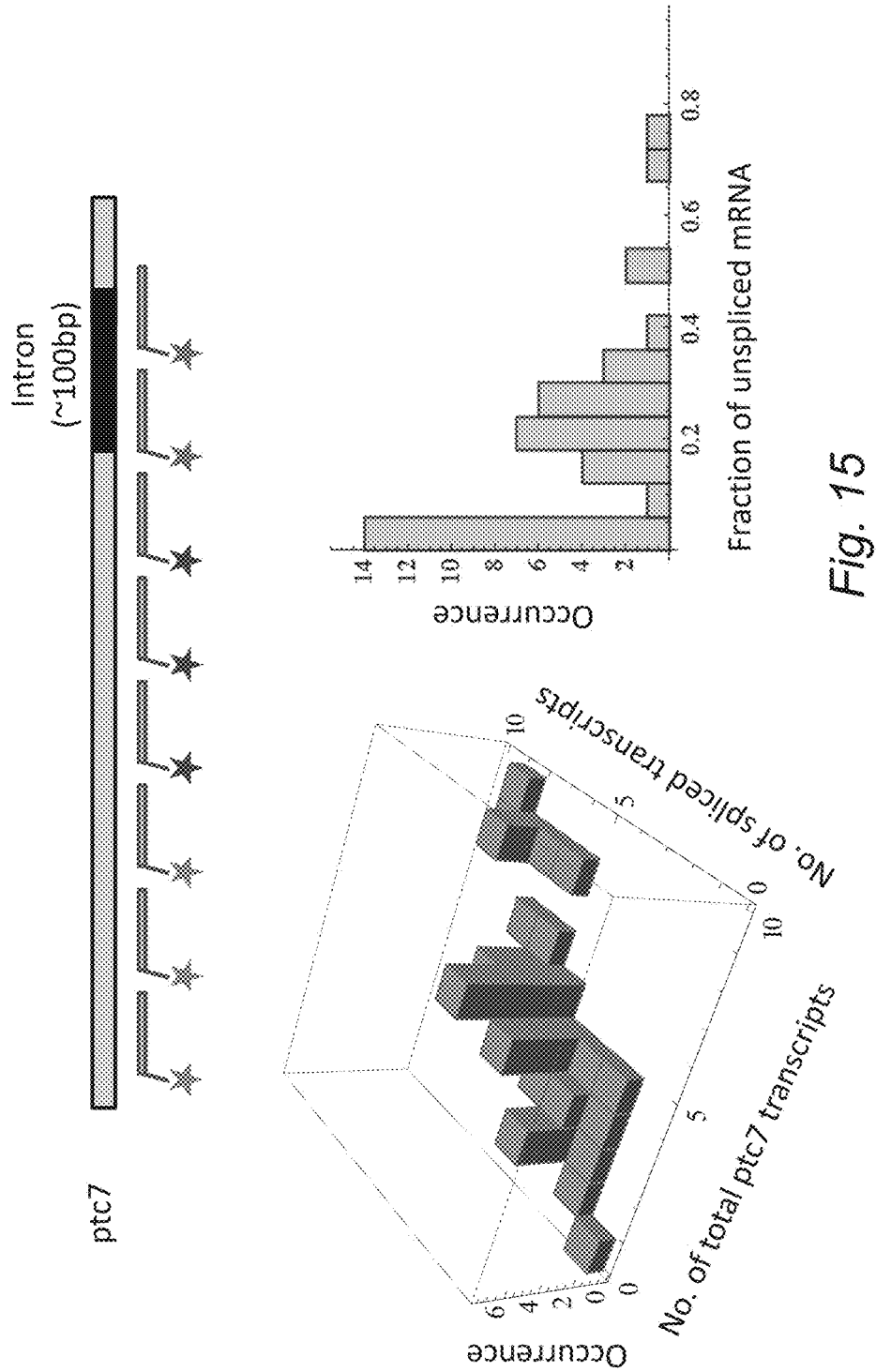
FIG. 15 depicts, in accordance with an embodiment of the invention, data relating to alternative splicing in single yeast cells.
Figure 22:
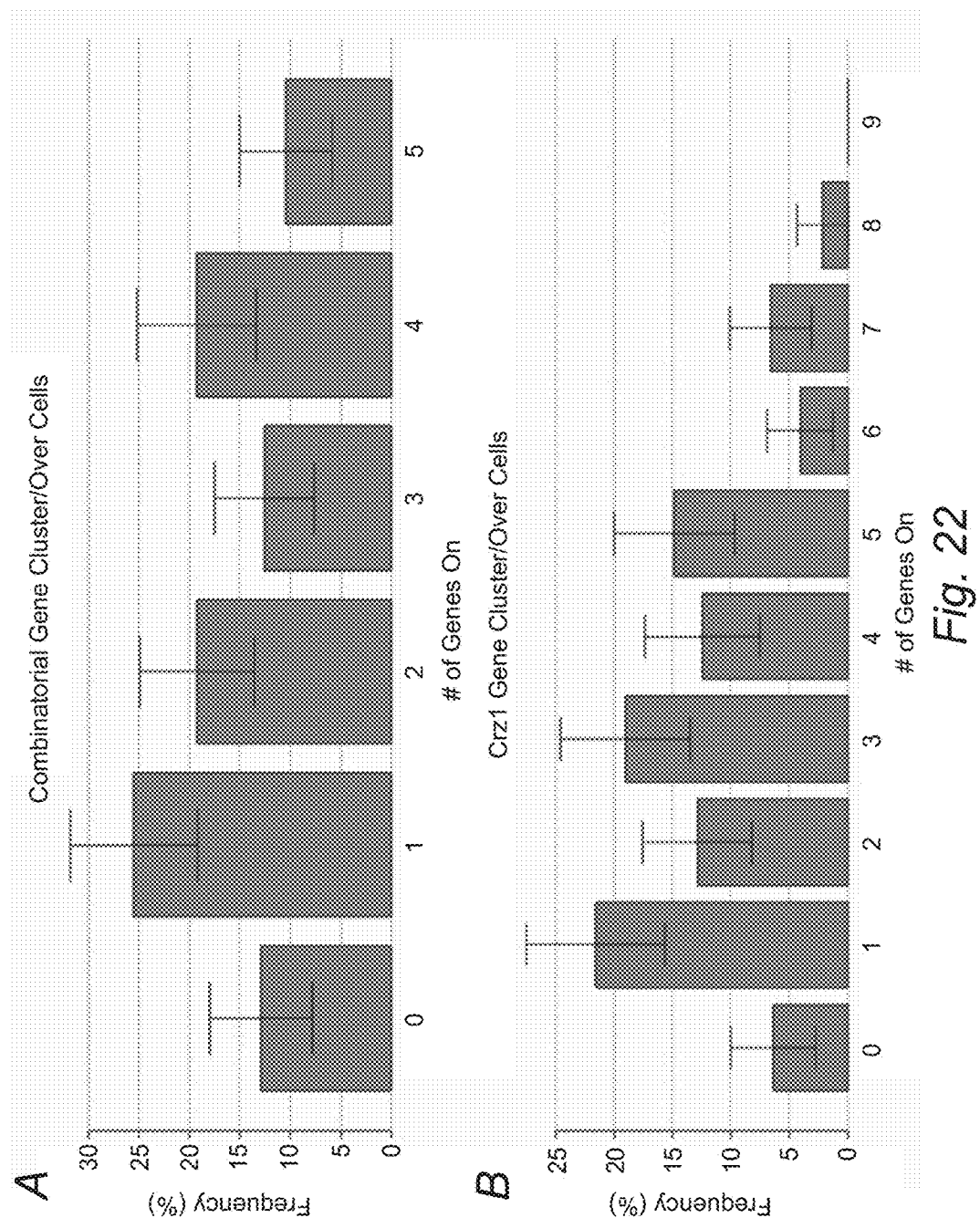
FIGS. 22A-C depict, in accordance with an embodiment of the invention, coordination under strong Crz1 localization. A-B) Cells with over-expressed Crz1. The coordination plots of combinatorial and pure Crz1 genes are shown. Compared to FIG. 12, coordination is similar even though Crz1 concentration is increased by 50-100 fold. C) 3D scatter plot of three mRNAs measured by smFISH 10 minutes after 200 mM $CaCl_2$ induction. Under these conditions, Crz1 is strongly localized in all cells for 10 minutes. Yet, cells with no expression in one or two of the genes are observed while other genes are fully expressed. A scatter plot of cells fixed at 2 hours after induction is shown.
Figure 22:
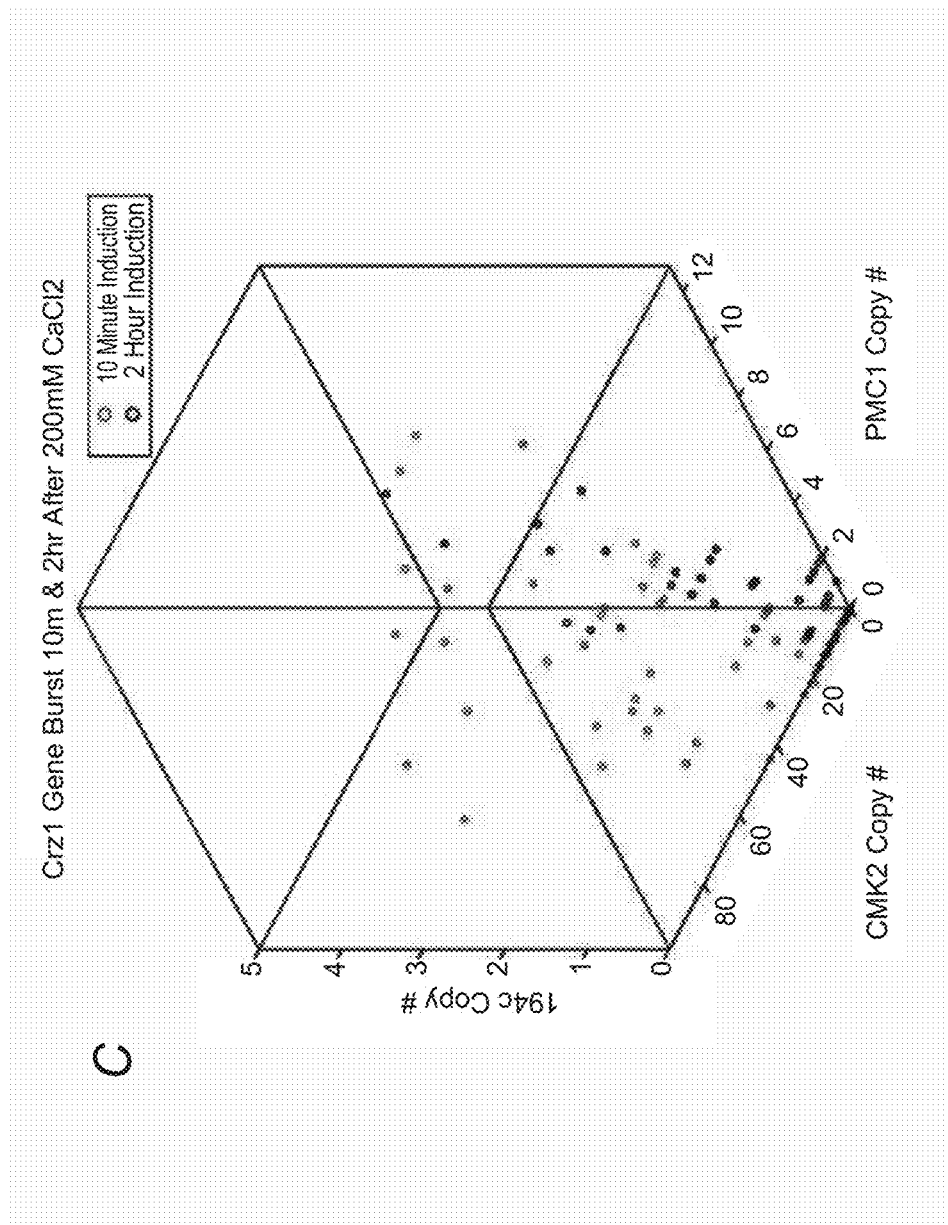

The inventors last examined whether combinatorial regulation affects the level of coordination within the combinatorial subgroup of Crz1 genes. The inventors found that when both groups of genes were on, the combinatorial target genes were as well coordinated as the pure Crz1 targets (FIG. 12b,d). In cells with only the combinatorial genes expressed, the level of coordination among those genes was also similar to that of cells with both groups of genes on (FIG. 12 b,c). In both cases, a relatively heterogeneous pattern of expression was observed, suggesting that there may be intrinsic limits to how well genes within a regulon can be coordinated. To determine if this lack of coordination was due to the concentration of TF, the inventors profiled cells with Crz1 over-expressed by 50-100 fold. The inventors still observed that not all of the Crz1 genes switched on simultaneously (FIG. 22 a,b). To make sure this lack of coordination was not due to the short duration of Crz1 pulses lasting typically 2-3 minutes the inventors profiled cells 10 min after induction with a high concentration of Calcium (200 mM). At this concentration of calcium, Crz1 immediately translocated into the nucleus and remained strongly localized for 20 minutes. However, the inventors still observed significant heterogeneity in expression (FIG. 12c). These experiments indicate that there are additional barriers to transcriptional activation at the individual promoters that cannot be overcome by increasing TF concentration and search kinetics. Given these factors, the wild-type concentration and kinetics of Crz1 are optimal for regulating its downstream targets. While not wishing to be bound by any one particular theory, concentrated pulses of TF activation may be a mechanism to allow even weakly induced TFs to switch on much of their regulons in a timely and organized fashion. The prevalence of pulsing in many stress response systems may serve the same goal.

Example 11

Discussion

Under a super-resolution microscope, cells become virtual microarrays with giga-pixel information density. Because individual molecules can be spatially resolved, their identities can be assigned a unique combinatorial code. The inventors demonstrated two such combinatorial labeling schemes, one based on the resolving the spatial sequence of labels on mRNAs and the other dependent on discriminating the combination of fluorophores in the label. On the one hand, the spatial coding scheme can be efficiently scaled up, but is error prone and requires molecules to be stretched out. On the other hand, the spectral coding scheme is more robust and can apply to other molecules besides mRNAs, but requires additional fluorophores to increase throughput. The inventors showed that by using 7 super-resolution fluorophores, 32 genes can be detected simultaneously in single cells. This multiplexing capacity is increased to 100 genes if 9 of the currently available fluorophores are used ($_9C_4$=126). As multiplex capacity increases exponentially with the number of fluorophores available, even the spectral coding scheme has the potential to achieve transcriptome level multiplexing if additional emitters are used ($_{18}C_6$=18,532).

Super-resolution barcoding provides a useful single cell follow-up technique to high-throughput sequencing technologies. One can sequence a population of cells from cultures or tissue samples, identify the genes of interest and then profile them in single cells with super-resolution barcoding. The advantage of this approach is three fold. First, direct imaging of the sample preserves the spatial information both within cells and among cells. With the application of light sheet microscopy, the technique can be extended into optically thick samples. This advantage makes it a powerful tool in studying signaling in heterogeneous systems such as microbial ecosystems, tissue and embryos, where interactions among different cellular populations play an essential role in cellular decisions. Second, because of the single-molecule and in situ nature of the technique, the method is quantitative and avoids intrinsic bias in RNA extraction and conversion to cDNA. Lastly, many cells can be imaged simultaneously under a microscope quickly and throughput can be scaled up without significant costs. Compared to the high cost and long waiting time for sequencing single cells, the super-resolution FISH approach is economical to scale up. After the initial cost of the probe set synthesis, the probe set can be hybridized many thousands of times to wild-type and mutant organisms.

The combinatorial labeling scheme can be applied to many types of molecules in the cell. The inventors demonstrated labeling mRNAs to quantify expression levels and splice variants. It is a short leap to consider combinatorially labeling chromosomes and proteins, for single cell proteomics and possibly ChIP experiments. For many types of biochemical techniques, such as microarrays, there is an equivalent single-cells experiment possible by application of super-resolution barcoding. The spatial separation step performed traditionally by gels or dilution on a chip can be replaced conceptually by super-resolution imaging to resolve molecules in situ. Further implementations of the super-resolution combinatorial imaging techniques will allow for direct observations of the interactions of biological components within single cells and aid in gaining an integrative picture of how they give rise to biological function.

Example 12

Experimental Procedures Probes Design, Purification and Hybridization

25mer oligonucleotide probes were designed to match melting temperature whenever possible. STORM probes were designed with 2 base pair spacing between probes to allow efficient reactivation of the STORM pair dyes, often leading to varying TM between STORM probes. Alexa 405, Fluorescein, and Cy3 were used as the activators and Cy5 as the switchable dye. Labeling and purification of the probes followed the protocol previously described herein. Yeast cells were grown in minimal media with 50 mM calcium and fixed in log growth phase following the Singer lab protocols with the addition of 0.1% $NaBH_4$ treatment before the ethanol permeabilization step. The inventors found the NaBH4 treatment significantly decreased the auto-fluorescent background of fixed yeast cells. Cells were stored at −20 C in Eppendorf tubes and aliquoted out for hybridization experiments. Cells were hybridized with the probes overnight at room temperature in 20% Formamide and 10% dextran sulfate. After hybridization, cells were washed in Formamide and 0.2×SSC solution 3 times and imaged.

Examples 13

Imaging

For conventional epi-fluorescence microscopy, images were acquired on an Olympus IX81 with a 100×sapo objective with laser illumination at 532 nm, 594 nm, and 640 nm. Images were acquired with Micromanager software and an Andor Ikon CCD. FIONA images were acquired in 3 different fluorescence channels (Semrock zero line filters). The centroids of the FISH PSFs were calculated in each channel and the images were aligned by center of mass alignment of co-localized PSFs between channels. This was sufficient for alignment without correcting for rotation and dilation. STORM imaging was performed on a Nikon TI-eclipse microscope with PFS autofocus lock. The imaging lasers, a 640 nm laser along with a 30 mW 691 nm and a 30 mW 730 nm laser (Coherent Lasers) were brought to the sample through a 100×TIRFM objective. 405 nm, 473 and 556 lasers were used as activation lasers and imaging automation was controlled by Micromanager software.

For the spatial coding images, samples were first imaged with only the 640 nm laser for 100 frames to switch off Cy5 and to determine the non-specific blinking rate. Then, 100 frames were acquired in each activation channel by co-illumination of the activation and the imaging lasers. This reduced the cross-talk among the different activation channels.

For the spectral coding images, the samples were first bleached in all imaging channels for 6 frames. Samples were imaged in order of the activators, starting at 556 nm through 473 nm and to 405 nm. For each activator, the microscope cycled through imaging with the 730 nm followed by either the 640 nm or 691 nm laser for 48 cycles. Samples were only illuminated with the activation light in the cy7 channel.

Activation powers were selected to maximize the activation rate while avoiding crosstalk among the channels. The 640 nm and 691 nm excitation lasers alternated after every emitter cycle. This scheme reduces the photobleaching due to spectral overlap between the Cy5 and Cy5.5 emitters. Following this imaging cycle, the 640 nm lasers were continuously used to image Cy5 for another 30 frames of specific activation. Throughout the imaging routine, for every 4 cycles of the imaging lasers, 2 cycles without the activator lasers were acquired. This enabled ruling out many of the false positive and nonspecific blinking events in the images. The activation lasers were controlled by an Arudino microcontroller board and a servo motor shutter. Fluorescent beads (Invitrogen F-8810) were used as fiducial markers to correct for stage drifts. The microscope stages (Prior and ASI) were automated and controlled by acquisition software to enable multi-position imaging. Buffers used in STORM imaging followed the protocol in Bates et al. (previously cited), with Glucose Oxidase as the oxygen scavenger and BME as the reducing agent.

Example 14

Analysis

Images from FIONA and STORM experiments were analyzed with a Mathematica script. In the STORM analysis, the beads were first aligned to determine the stage drifts. Beads emit on the order of 50,000 photons per image, and could be localized to a few nanometers. Beads close to the cells were eliminated from analysis as the switching of fluorophores in cells can disrupt the bead alignment. Then, fluorophores were selected from each image by intensity thresholding, and their centroid calculated. Because the samples were densely labeled (10-20 Cy5 dyes per mRNA molecule), the probability of multiple fluorophore activation was high. A relatively high activation rate, often leading to simultaneous fluorophore activation, is essential for overcoming the nonspecific activation frequency in densely labeled samples. The inventors did not reject activation events that involved multiple fluorophores. To determine which of the barcode colors are present, instead of nonspecific activation, the inventors compared the number of activation events that occurred in the specific activation channel versus the activations observed in frames with no activation. If the nonspecific activation events exceed specific activation events, then that channel was rejected. As several of the activators and emitter channels can crosstalk into other channels, the inventors quantified the crosstalk ratio and rejected activation events if they fell below certain thresholds, as described herein. Switching events that spatially cluster together were grouped to display the resolved barcode. For spectral barcodes, activations were clustered together on a 184 nm grid. Activation events near grid vertices were assigned to a neighboring region containing localizations of the same fluorophore pair. For 3 color barcodes, the center color was determined by finding the position that was not one of the two localized colors separated by the longest distance. Cell positions were determined by manual segmentation. Barcodes were collected and tabulated for each single cell. Cross-correlation was calculated using the correlation function in Mathematica and the standard errors were calculated from re-sampling the data 100 times.

Example 15

Hybridization Efficiency and 3 Color Spatial Reconstructions

To determine the hybridization efficiency of the probes, the inventors used photobleaching to measure the number of bleaching steps. 12 27 mer probes targeting Cmk2 were coupled to Cy3 and imaged with a 532 nm laser. Discrete photobleaching steps were observed corresponding to bleaching of single fluorophores (FIG. 16). The average step size was ~300 cts. Using this value as the average fluorophore intensity, the inventors estimated the number of probes bound per mRNA based on the dot intensities in the image before photobleaching. Some variations in intensity were likely due to unevenness in illumination and homo-quenching effects of closely spaced fluorophores. The inventors found that on average 8.1 probes were bound out of the total of 12 probes, suggesting a hybridization efficiency of 67.5±9.1% (FIG. 16) per probe. The observed distribution is consistent with a binomial distribution with the probability of each probe binding at 67%. While not wishing to be bound by any one particular theory, less than perfect hybridization efficiency may be due to the tertiary structure of the mRNA molecule and heterogeneities in bound ligands such as proteins on the mRNA. In a later experiment the inventors demonstrated a more robust coding scheme in which single-colored probes were distributed throughout the mRNA. If an occluding molecule is bound to a small region of mRNA, it should only block a subset of the probes in every color, as opposed to removing a single color completely. This hybridization efficiency implies that mRNAs tagged with 4 probes have a 99% chance of being detected with at least 1 probe bound. This is consistent with the inventors' observation that 96±2% (N=29) of spots co-localized in all three channels in the 3 color YLR414c probes. This hybridization efficiency allowed the inventors to monitor the splicing of small introns. With 4 probes, there is a 99% probability that at least 1 probe is bound in the intronic regions of PTC7. The accuracy of the spliceform quantitation was confirmed with qPCR results.

For the 3 color YLR414c centroid reconstruction, the inventors observed that 74±8% (N=28) of codes reconstruct correctly. For the PTC7 reconstructions, the inventors observed that 67% (N=12) of the reconstructions contain the correct order. The lower reconstruction rate for the PTC7 transcript is because the lower copy number of PTC7 unspliced transcripts make it less accurate to correct for the offset between the fluorescence channels without extra fiducial markers. This can be corrected by using exogenous fiducial markers. With the cy3 cy5 pair for super-resolution imaging, this labeling scheme improves background rejection, as both probes are required for the fluorophore to be re-activated. Non-specifically bound Cy5 probes in the cell cannot be reactivated. In comparison, directly labeling oligos with Cy3-Cy5 covalently-linked pairs will have the same non-specific background as standard FISH and have a drastically increased blinking rate due to the complex photophysical properties of the Cy3-Cy5 heterodimer. Indeed, the inventors observed prior to inactivation, cells contain a hazy background of singly bound probes in addition to the hybridized FISH spots. After imaging with the 640 nm laser for 4-5 frames, these non-specifically bound molecules switched off and blinked at the non-specific activation rate of cy5. Upon activation with 405,473 or 532 nm lasers, these background probes did not reactivate. It is highly unlikely that probes with an activator would be non-specifically bound within STORM distance (<1 nm) from a Cy5. The majority of spots that reactivated were specific mRNA targets, although noise was observed from cellular autofluorescence and probe complexes. Some of this noise was due to x-talk among specifically bound dyes. The inventors observed x-talk ratios of around 7% for the most egregious Cy5-dye pairs (FIG. 18). It has been previously reported that 473 nm laser can activate cy3-cy5 pairs with 10-20% efficiency. The inventors adjusted the 473 nm laser power such that it is higher than the non-specific blinking rate, but less than the power needed to consistently activate Cy3 cy5 probe pairs.

The cost of the background rejection of cy5 pair-probes is reduced effective hybridization rate. As both probes are required for a functional dye pair, the effective hybridization efficiency is $(67\%)^2=45\%$. Thus the probability of having at least 1 pair formed out of a redundant set of 4 probes pairs is $1-(0.45)^4=0.9$. With a 3 color barcode, the theoretical probability of having all three colors present is $0.9^3=0.72$. The inventors observed a 61±8% probability (50 out of 85 reconstructions) that 3 colors were present on a given mRNA, and a 33±6% probability (28/85) of resolving only 2 colors. A typical reconstruction from an image is shown in FIG. 20 with YLR414c hybridized with 12 probe pairs. The effective hybridization efficiency can be improved by using more probe pairs. With 8 probe pairs per position, the 3 color colocalization rate is increased to >95%. The long term solution is the development of super-resolution fluorophores with improved contrast ratios. With reduced blinking, fluorophores can be directly labeled to oligos. As in the experiments, only 4 redundant probes are needed to co-localize in 3 colors with 96% probability and 6 colors with 93% probability.

The inventors' use of physical compression allowed for imaging most RNAs in a single focal plane. This simple physical treatment permitted the inventors to forgo axial resolution of barcodes. Currently, 2 approaches are available to improve axial resolution. Interferometric PALM would allow for resolving axial resolution to 5 nm, and astigmatic or dumbbell shaped point-spread-function can improve axial resolution to 50 nm. Implementing the astigmatic approach would be insufficient to resolve the color positions within a barcode, but it would be helpful to discern different barcoded mRNAs if they overlap in the xy but not z dimension.

Example 16

Scaling Up Multiplexing Capacity with Spatial and Spectral Barcoding

Spatial and spectral barcoding schemes have different strategies for scaling up the throughput. Spatial barcoding is efficient. In principle, five-position barcodes (shown in FIG. 17) allow at least $9^5/2=29,525$ genes to be tagged simultaneously in single cells. In practice, super-resolution barcode readout accuracy and labeling density are constrained by the non-specific 'blinking' of the Cy5 dyes (i.e. contrast ratio), occurring at 1 in 200 frames per molecule. This means that each diffraction limited spots can only accommodate 10-20 mRNA molecules, limiting the number of total mRNAs resolvable in cells to <10,000. While multiplexing hundreds of genes is feasible with existing fluorophores, further increasing the multiplex capacity will require development of fluorophores that have high contrast ratios and can be directly coupled to oligos to accommodate dense and high-fidelity labeling. In addition, spatial barcoding requires mRNAs to be stretched out to resolve the spatial sequence of colors. The inventors experimented with different fixation conditions and methods to extend mRNAs, but found compressing cells to be a very good method to consistently stretch out transcripts. As thick sample are routinely squeezed to reduce optical sectioning for FISH imaging, spatial barcodes may be readily resolved in compact and compressible systems such as embryos. However, not all biological samples can be compressed, such as tissue samples or biofilms. Spectral coding provides an alternative labeling scheme. In this scheme, the inventors note that the multiplex capacity increases exponentially with the number of fluorophores available. In principle, cyanine dyes can be extended further into the infrared region to act as additional emitters.

Example 17

Crosstalk and Accuracy of the Barcode Readout

The spectral coding approach is more robust because errors associated with identifying spatial positions can be avoided. However, crosstalk among different fluorophores can impede the identification of the proper barcodes and result in leakage among the barcodes. To control for crosstalk, we performed several control experiments.

First, the inventors imaged individual dye pairs with the full imaging routine, going through all activators and emitters to quantify the amount of leakage from each dye pair into the others. By examining all 7 dye pairs used in in the inventors' study, they found the most leakage occurs from Cy3 activators, which can be activated by the 473 and 405 nm lasers. However, Alexa 488 and Alexa 405 cannot be activated with the 555 nm laser, so the crosstalk only appears in one direction. From the single dye pair experiments the inventors quantified the idealized x-talk with 12 of the target dye pairs, imaged in exactly the same routine as their barcode quantification. There is a small amount (~1%) of non-specific activation in Alexa 405 and 473 with 556 nm activation, due to non-specific blinking of the dye pair. The probe pairs that exhibit x-talk at a rate higher than previously reported are A488 and Cy3 (6-6.5%). While not wishing to be bound by any one particular theory, this may be due to the close proximity of the dyes to each other in the probe design. This x-talk was still clearly separable from signal. In cy5.5, the inventors only used the cy3-cy5.5 pair, thus no crosstalk between 5.5 dyes could occur. To reject the false activation of cy3 by the 473 laser, the inventors discarded activations in the 473 channel that were less than 30% of the activations observed in the 555 nm laser channel. Similarly, the inventors set the threshold for rejection at 15% and 30% respectively for 405 nm activation of A488 and Cy3. In addition, there is crosstalk between the cy5 and cy5.5 emitter channels. Since this crosstalk only occurs in the cy3 activation channel, the inventors compared the activation intensity in cy3-cy5 vs cy3-cy5.5 channels and found about 12% spectral crosstalk between the 2 emitters. Thus, any activation in cy5.5 that was less than 30% of the activation in cy5 was rejected.

Second, to test the accuracy of the 3 color barcode readout, the inventors used the barcode that is the most prone to crosstalk, which is the cy3 activator paired with all three emitters. Several false-positive barcodes were observed at a 20% crosstalk rate with the proper barcode. However, this represents the worst-case scenario for crosstalk, since Cy3 can be activated by both 405 and 473 nm lasers. In addition, the gene targeted with this probe set has a relatively low copy number, so false barcodes due to cellular background and nonspecific blinking appeared at a relatively higher frequency compared to the correct barcode (FIG. 18). A different 3-color barcode with 405, 488 and cy3 as activator and cy5 as emitter, showed a much lower crosstalk ratio (FIG. 18). Most of the extraneous barcodes observed in these cases were due to background blinking in the cell and did not scale with the copy number of the genes probed. Thus, they contribute to a constant background of barcodes that is additive but not multiplicative to the real barcodes.

Third, when the inventors analyzed data of the full dataset with 32 genes, they examined the frequency of observing the barcode position that was not coded. With a total of 35 possible coding positions in the scheme used, there were 3 empty code positions that should not show up. This false identification frequency is 0.67±0.84 copies per cell, suggesting the inventors' entire barcode set imaged simultaneously is not significantly affected by false positives. In addition, the inventors performed analysis on the full data set with a single gene barcode dropped out, as a built in control on barcoding. The inventors observed that the empty position which is normally present at 4.9±2.3 copies per cell was present at 0.75±0.84 copies per cell, indicating a relatively small amount of crosstalk into that position from other barcodes.

Figure 24:
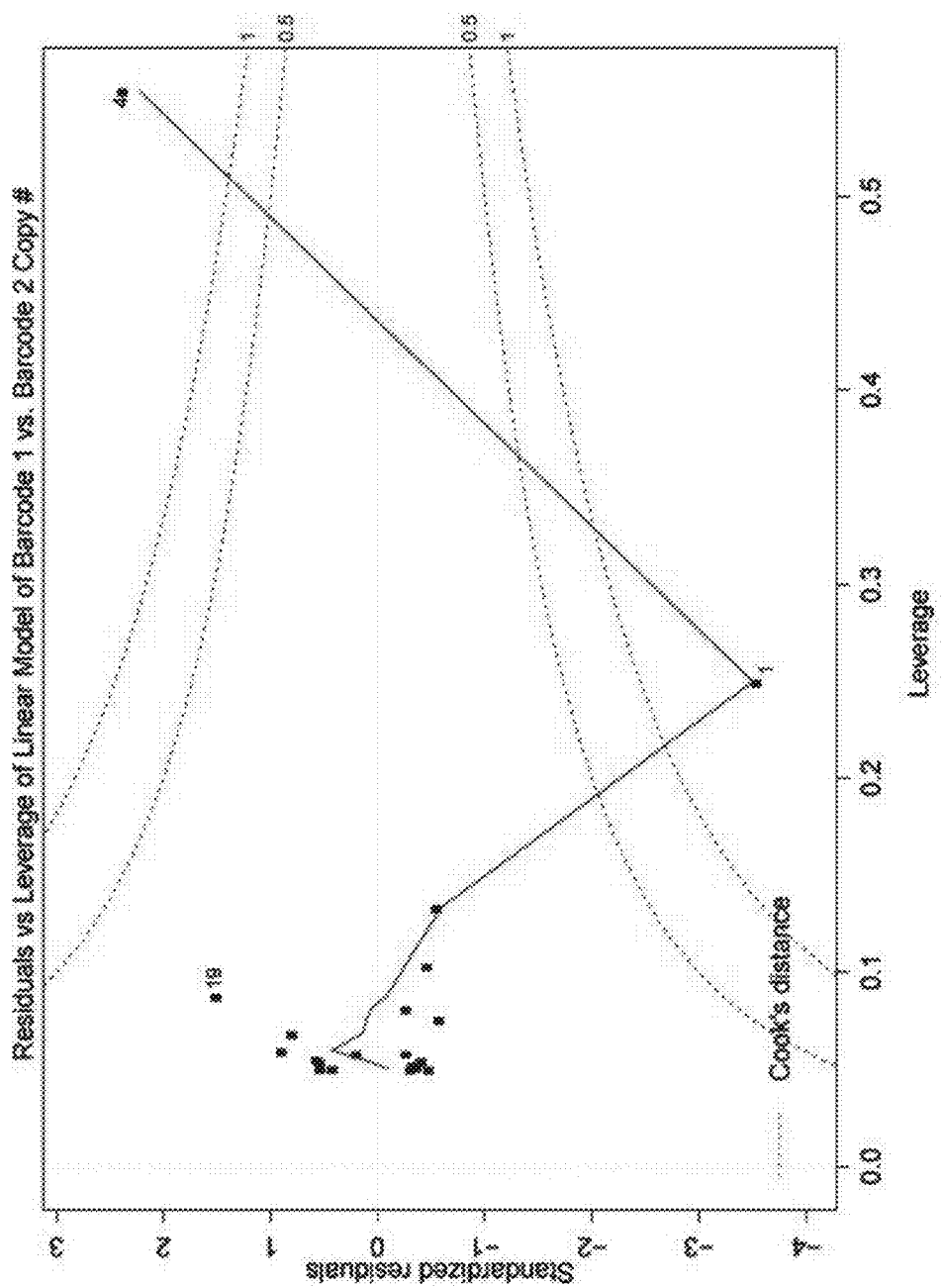
FIG. 24 depicts, in accordance with an embodiment of the invention, a plot of residuals of linear fit to the switched barcode vs. leverage points. Two points have a Cook's distance above 1, indicative of a very strong influence on regression and a potential outlier. On further analysis, point 1 was found to be the only true outlier, as its removal led to point 4's residual following dramatically, placing it under the Cook's distance threshold of 0.5. Although point 4 has a high leverage, it was found to agree with the inventors' linear model following leave-one-out analysis of the additional data points after point 1 was dropped.

Fourth, the inventors took a 20 gene probe set containing cy5 and cy7 emitters, and circularly permute the activators (405->488, 488->cy3, cy3->405). This effectively scrambled the barcode assignment since the emitters remained in the same position. The inventors observed a strong correlation between genes measured amongst both probe sets, indicating no significant bias is introduced by a particular assignment of the barcode. One significant outlier existed in the analysis, ylr194c. This outlier was dropped based upon its high Cook's distance of 2.08226 (FIG. 24). A regression with an $R^2$ value of 0.88 was obtained following removal of the outlier connoted in red. The other large outlier with a high copy number also has a high Cook's distance of 3.5515. Despite its leverage, the point fits well on regressions obtained from leave-one-out analysis of the remaining points, so it was retained in the analysis.

Fifth, the inventors performed single molecule FISH experiments measuring the expression of 11 genes, including 8 crz1, 1 msn2 and 2 aging genes. The inventors observed a $R^2$=0.95 correlation between the mean levels measured by smFISH and the barcode approach.

Sixth, The inventors also performed q-PCR experiments measuring the mean copy number of 8 crz1 target genes. The inventors observed 0.95 correlation between the qPCR and the barcode data. The qPCR experiments were performed in triplicates and quantitated using 1x, 10x and 100x serial dilutions.

Example 18

Single Cell Profiling and Correlation

The inventors measured the copy number of probed genes by tabulating the barcode reconstructions in single cells, for 62 cells. As shown in FIG. 18, on average 2-3 cells were observed per field of view. Each set of STORM images took ~10 minutes to acquire. The inventors manually found the positions of 10-15 cells and set up an automated stage to scan through the positions for STORM imaging. It took approximately 5-6 hours to collect 60 cells. The field of view (FOV) was kept small to reduce auto-fluorescent background from glass. While not wishing to be bound by any one particular theory, in principle, quartz slides could decrease background and allow the FOV to expand, dramatically increasing throughput.

Because Crz1 pulses occur stochastically in individual cells, promoter responses should be averaged out in population measurements. The mRNA copy numbers are shown in FIG. 19. The copy number shows large cell-cell variability, ranging from less than 1 copy per cell to 10 copies (CV-1). The average number of transcripts measured by barcoding was checked against tabulations determined by single molecule FISH (smFISH). In smFISH, each mRNA was hybridized with 12 probes in cy3 or cy5. The copy numbers were well correlated (R=0.95, FIG. 18a). There was a 2 fold difference between the copy numbers, which is most likely due to barcodes that are missing 1 or 2 color positions due to the hybridization efficiency. However the good correlation indicates that there is little bias among the different barcodes, regardless of the combination of activator and emitters used.

The inventors found no connection between chromosome positions and gene correlations. Yps1, Put1, Pmc1, YLR194c and YLR414c are on chromosome 7 in that order. Cmk2 and Npt1 are on chromosome 15. Gyp7 is on Chromosome 4 and Sok2 is on chromosome 13. Npt1 and Pmc1 are well correlated, but are on different chromosomes, while YLR414c and yps1 are not as well correlated, but on the same chromosome. Previous experiments revealed little pairwise correlation (~25%) among mRNAs of constitutive highly expressed genes. Thus the correlations observed were not due to static heterogeneity in the cell. At the same time, there appears to be an intrinsic limit to how well coordinated genes within a regulon can be. The inventors tested 2 extreme conditions where Crz1 concentration should not be the limiting factor, one by over-expressing Crz1, and the other by imaging cells immediately after treating with a high concentration of calcium (10 minutes at 200 mM). The inventors still observed that not every Crz1 target gene switched on, indicating additional barriers to transcriptional activation at individual promoters.

Example 19

Oligonucleotide Sequences

TABLE 3

Probes for smFISH 5' amine modified

| SEQ ID NO | Sequence | Probe ID |
|---|---|---|
| 1 | gatctcacgctacaccatagaatgaa | ylr414c-1 |
| 2 | catcaaaccctggtagttcctaccaa | ylr414c-2 |
| 3 | tatgctttaggatgtatttgatgtat | ylr414c-3 |
| 4 | actaatagggcggcaaaggcgaaaaa | ylr414c-4 |
| 5 | ccttatgtggatgatccagcgcaata | ylr414c-5 |
| 6 | caataccaataagaatggtaatgaac | ylr414c-6 |
| 7 | attttacttttagttttcgggcaa | ylr414c-7 |
| 8 | cagagcctcattgttgttgatattgt | ylr414c-8 |
| 9 | ggataccgtgaggcgaagaacatgat | ylr414c-9 |

TABLE 3-continued

Probes for smFISH 5' amine modified

| SEQ ID NO | Sequence | Probe ID |
|---|---|---|
| 10 | tacgaccaaagccctatatttatata | ylr414c-10 |
| 11 | agaactcaaagaagggagcaccgtcg | ylr414c-11 |
| 12 | cacagtaaattttatttatgggactg | ylr414c-12 |
| 13 | acggacgctaccttaccgttgactg | ylr194c-1 |
| 14 | tgtagaacctgacgtagtggtataa | ylr194c-2 |
| 15 | ttgattccggttttgatgaggatcc | ylr194c-3 |
| 16 | tcagttgtggctgaggacggtagcc | ylr194c-4 |
| 17 | cgaattcgtggtagttactatagta | ylr194c-5 |
| 18 | aggaggatgcggagttggtgattcc | ylr194c-6 |
| 19 | gcagttgaagttgtgcttacggcag | ylr194c-7 |
| 20 | tgtcgtggttttgccttgtgcatcc | ylr194c-8 |
| 21 | cataggtgttgctgacgacgttgct | ylr194c-9 |
| 22 | acagttgatgcgctttcttgggctt | ylr194c-10 |
| 23 | gtttgagctttccttttgtgagcta | ylr194c-11 |
| 24 | agtcttttgagcagcggctagagt | ylr194c-12 |
| 25 | atgcagacttcaatttcatttgctc | cmk2-1 |
| 26 | tgcagacgtaaatcatccaacgaat | cmk2-2 |
| 27 | ggaattctcttctatatcgttatcg | cmk2-3 |
| 28 | acctcttaattctattattaagctt | cmk2-4 |
| 29 | cgcaaagaaaaccctttcttaacgt | cmk2-5 |
| 30 | tgaagtaatccatggatcgtccagc | cmk2-6 |
| 31 | tcaatctcaatgccttcaagatgaa | cmk2-7 |
| 32 | tatggcatatggaaggttaccgggt | cmk2-8 |
| 33 | ttcaacgctttcggcaataaaagga | cmk2-9 |
| 34 | caccaatggaccatatatcacaagg | cmk2-10 |
| 35 | ggtgccacataacccaacgatccgg | cmk2-11 |
| 36 | caattgtttagctataccgaagtcc | cmk2-12 |

Example 20 qPCR Primers

TABLE 4 qPCR Primers

| SEQ ID NO | Primer ID | Sequence |
|---|---|---|
| 37 | Cmk2 F | tcgcctctggtaattgcggac |
| 38 | Cmk2 R | taacccaacgatccggctgc |
| 39 | Pmc1 F | ttgttgcggtcactggcgat |
| 40 | Pmc1 R | aagcctctctggcaacctcc |
| 41 | Ylr414c F | gctacgctatcttcgttgggc |
| 42 | Ylr414c R | ctggataccgtgaggcgaaga |
| 43 | Ylr194c F | agcaactctgccgtaagcaca |
| 44 | Ylr194c R | gtcgttgaggaggatgcgga |
| 45 | Npt1 F | gggagatcctgccactgtga |
| 46 | Npt1 R | aggtccatctgtgcgcttcg |
| 47 | Gyp7 F | acgatgggaggctgagggtc |
| 48 | Gyp7 R | accccaaactttccctcgca |
| 49 | Put1 F | ggcgataaaacgggcactga |
| 50 | Put1 R | aggcgacaaccaagtgaccaa |
| 51 | Yps1 F | ttgacgggaacgggcagtg |
| 52 | Yps1 R | ccgaagcaggcacggattga |
| 53 | Actin F | acgtttccatccaagccgt |
| 54 | Actin R | ggaacgacgtgagtaacacca |
| 55 | Ptc7intron F | ggtccccttatggtatgtttattg |
| 56 | Ptc7intron R | tttgactgcaggatcctatgatat |
| 57 | Ptc7exon F | cccctttatggatcctgcagtc |
| 58 | Ptc7exon R | cctgattggctacctgaact |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

---

What is claimed is:

1. A method for detecting a single molecule of each of a plurality of mRNA species in a single cell, comprising:
   (i) creating a plurality of molecular barcodes for the plurality of mRNA species in the single cell, wherein each of the plurality of molecular barcodes is a molecular barcode for a single molecule of one mRNA species of the plurality of mRNA species in the single cell, by performing steps comprising:
      (a) providing a plurality of sets of different fluorophore-labeled oligonucleotide probe pairs for hybridizing with the plurality of mRNA species, wherein each set of the plurality of sets of different fluorophore-labeled oligonucleotide probe pairs comprises a plurality of different fluorophore-labeled probe pairs that specifically hybridize to a single molecule of one mRNA species of the plurality of mRNA species, the probes in each probe pair of the probe-pairs of each set of the plurality of sets of different fluorophore-labeled oligonucleotide probe pairs comprise a nucleic acid probe labeled with a photoswitchable fluorophore and a nucleic acid probe labeled with an activator fluorophore of the photoswitchable fluorophore, wherein the photoswitchable fluorophore can be cycled between a fluorescent state and a dark state and the activator fluorophore is capable of facilitating photo-activation of the photoswitchable fluorophore at a specific wavelength, wherein each probe in each probe pair of the probe pairs of each set of the plurality of sets of different fluorophore-labeled oligonucleotide probe pairs specifically hybridizes to a different location of one mRNA species of the plurality of mRNA species, and the photoswitchable fluorophore and the activator fluorophore in each probe pair of the probe pairs of each set of the plurality of sets of different fluorophore-labeled oligonucleotide probe pairs are different such that the plurality of sets of different fluorophore-labeled oligonucleotide probe pairs can generate different fluorescent signals with different colors or with different fluorescent intensities, and
      (b) hybridizing each mRNA species of the plurality of mRNA species within the single cell with each set of the plurality of sets of different fluorophore-labeled oligonucleotide probe pairs, thereby forming a plurality of mRNA-probe complexes, wherein each of the complexes comprises one mRNA species of the plurality of mRNA species and said plurality of different labeled probe pairs that specifically hybridizes to a single molecule of the one mRNA species of the plurality of mRNA species such that the photoswitchable fluorophore and the activator fluorophore of each probe pair of the probe pairs on each of the complexes are in sufficiently close proximity to each other and two or more different fluorescent signals are formed along the sequence of the one mRNA species of the plurality of mRNA species on each of the complexes in a spatially ordered fashion, a pattern of fluorescent signals is formed on each of the complexes, and the pattern of fluorescent signals on each of the complexes is different, wherein each molecular barcode of the plurality of molecular barcodes corresponds to the pattern of fluorescent signals formed on each of the complexes; and
   (ii) resolving each molecular barcode of the plurality of molecular barcodes by utilizing super resolution microscopy and detecting the single molecule of each of the plurality of mRNA species in the single cell based on analyzing each of the plurality of molecular barcodes the fluorophore-labeled oligonucleotide probe pairs comprises an oligonucleotide probe labeled with a different emitter fluorescent dye and an oligonucleotide probe labeled with a different activator fluorescent dye, wherein each activator fluorescent dye is capable of emitting at a wavelength or frequency that activates a reporter fluorescent dye in its pair, and wherein each oligonucleotide probe of each oligonucleotide probe pair of the fluorophore-labeled oligonucleotide probe pairs is designed to hybridize with an adjacent but not overlapping region of the first mRNA species such that the activator fluorescent dye and emitter fluorescent dye of each oligonucleotide probe pair are positioned within two bases of one another when hybridized to the first mRNA species, such that if the emitter fluorescent dye is deactivated, it can become reactivated upon excitation of the activator fluorescent dye by light corresponding to an absorption wavelength of the activator fluorescent dye, such that the probe pairs are capable of forming a spatially ordered sequence of distinct signals along the sequence of the first mRNA species of interest;
   (b) providing two or more sets of different fluorophore-labeled oligonucleotide probe pairs, different from those in step (a), for hybridizing with at least a second mRNA species different from the first mRNA species, wherein each of the fluorophore-labeled oligonucleotide probe pairs comprises an oligonucleotide probe labeled with a different emitter fluorescent dye and an oligonucleotide probe labeled with a different activator fluorescent dye, wherein each activator fluorescent dye is capable of emitting at a wavelength or frequency that activates the reporter fluorescent dye in its pair, and wherein each oligonucleotide probe of each oligonucleotide probe pair of the fluorophore-labeled oligonucleotide probe pairs is designed to hybridize with an adjacent but not overlapping region of the second mRNA species such that the activator fluorescent dye and emitter fluorescent dye of each oligonucleotide probe pair are positioned within two base pairs of one another when hybridized to the second mRNA species, such that if the emitter fluorescent dye is deactivated, it can become reactivated upon excitation of the activator fluorescent dye by light corresponding to an absorption wavelength of the activator fluorescent dye, such that the probe pairs are capable of forming a spatially ordered sequence of distinct signals along the sequence of the second mRNA species of interest;

(c) for each optional additional mRNA species, different from the first mRNA species, different from the second mRNA species, and different from the other additional mRNA species, providing two or more sets of different fluorophore-labeled oligonucleotide probe pairs, different from those in steps (a) and (b), for hybridizing with the additional mRNA species, wherein each of the fluorophore-labeled oligonucleotide probe pairs comprises an oligonucleotide probe labeled with a different emitter fluorescent dye and an oligonucleotide probe labeled with a different activator fluorescent dye, wherein each activator fluorescent dye is capable of emitting at a wavelength or frequency that activates the reporter fluorescent dye in its pair, and wherein each oligonucleotide probe of each oligonucleotide probe pair of the fluorophore-labeled oligonucleotide probe pairs is designed to hybridize with an adjacent but not overlapping region of the additional mRNA species such that the activator fluorescent dye and emitter fluorescent dye of each oligonucleotide probe pair are positioned within two base pairs of one another when hybridized to the additional mRNA species, such that if the emitter fluorescent dye is deactivated, it can become reactivated upon excitation of the activator fluorescent dye by light corresponding to an absorption wavelength of the activator fluorescent dye, such that the probe pairs are capable of forming a spatially ordered sequences of distinct signals along the sequences of each additional mRNA species of interest;

(d) hybridizing, within said cell, a quantity of said first mRNA species with a quantity of said two or more sets of fluorophore-labeled oligonucleotide probe pairs designed to hybridize therewith;

(e) hybridizing, within said cell, a quantity of said second mRNA species with a quantity of said two or more sets of fluorophore-labeled oligonucleotide probe pairs designed to hybridize therewith;

(f) hybridizing, within said cell a quantity of each of said optional additional mRNA species with a quantity of said two or more sets of fluorophore-labeled oligonucleotide probe pairs designed to hybridize therewith:

(ii) exciting two or more fluorescent dyes of the two or more sets of fluorophore-labeled oligonucleotide probe pairs hybridized with said first mRNA species, thereby resulting in two or more separate color signals spatially ordered along the sequence of the single molecule of the first mRNA species, thereby forming a first molecular barcode;

(iii) exciting two or more fluorescent dyes of the two or more sets of fluorophore-labeled oligonucleotide probe pairs hybridized with said second mRNA species, thereby resulting in two or more separate color signals spatially ordered along the sequence of the single molecule of the second mRNA species that are distinguishable from the spatial ordering of the two or more separate color signals spatially ordered along the sequence of the single molecule of the first mRNA species, thereby forming a second molecular barcode;

(iv) exciting each optional two or more fluorescent dyes of each of the two or more sets of fluorophore-labeled oligonucleotide probe pairs hybridized with each optional additional mRNA species, thereby resulting in two or more separate color signals spatially ordered along the sequence of the single molecule of each optional additional mRNA species that are distinguishable from the spatial ordering of the two or more separate color signals spatially ordered along the sequence of the single molecule of each of the first mRNA species, second mRNA species, and any other additional mRNA species, thereby forming one or more additional molecular barcodes;

(v) resolving the first molecular barcode by resolving the two or more separate color signals spatially ordered along the sequence of the single molecule of the first mRNA species by using super resolution microscopy;

(vi) resolving the second molecular barcode by resolving the two or more separate color signals spatially ordered along the sequence of the single molecule of the second mRNA species by using super resolution microscopy, wherein the first and second molecular barcodes are distinguishable from one another on the basis of the two or more separate color signals spatially ordered along the sequence of the single molecule of the first mRNA species and the two or more separate color signals spatially ordered along the sequence of the single molecule of the second mRNA species; and (vii) resolving each optional additional molecular barcode by resolving the two or more separate color signals spatially ordered along the sequence of the single molecule of each optional additional mRNA species by using super resolution microscopy, wherein the first and second and other additional molecular barcodes are distinguishable from one another on the basis of the two or more separate color signals spatially ordered along the sequence of the single molecule of the first mRNA species and the two or more separate color signals spatially ordered along the sequence of the single molecule of the second mRNA species and the two or more separate color signals spatially ordered along the sequence of each single molecule of each optional additional mRNA species: thereby detecting two or more mRNA species in a single cell.

2. The method of claim 1, further comprising quantifying said plurality of mRNA species in the single cell.

3. The method of claim 1, wherein each of the plurality of sets of fluorophore-labeled oligonucleotide probe pairs includes four or more fluorophore-labeled oligonucleotides.

4. The method of claim 1, further comprising the cell.

5. The method of claim 1, wherein said cell is selected from the group consisting of a protist, a fungus, a plant cell, an animal cell, a mammalian cell, a mouse cell, a human cell, a cancer cell, a blood cell, a lymphocyte, an erythrocyte, a white blood cell, an epithelial cell, a pituitary cell, a gut or respiratory tract cell, a gland cell, a thyroid gland cell, a parathyroid gland cell, a adrenal gland cell, a muscle cell, a ciliated cell, an embryonic cell, a sensory transducer cell, a neuron, a glial cell, a lens cell, a kidney cell, a pigment cell, and a pancreatic cell.

6. The method of claim 1, wherein the photoswitchable fluorophore or the activator fluorophore is selected from the group consisting of fluorescein, rhodamine, Alexa Fluors, DyLight fluors, ATTO Dyes, and any analogs or derivatives thereof.

7. The method of claim 1, wherein said super resolution microscopy is selected from the group consisting of Stimulated Emission Depletion microscopy (STEDM), Ground State Depletion microscopy (GSDM), Spatially Structured Illumination microscopy (SSIM), Photo-Activated Localization Microscopy (PALM), Fluorescence-PALM (FPALM), Stochastical Optical Reconstruction Microscopy (STORM), and Fluorescence Imaging with One-Nanometer Accuracy (FIONA).

8. The method of claim 1, wherein the plurality of different fluorophore-labeled oligonucleotide probe pairs comprises 3 probe pairs.

9. The method of claim 1, wherein the plurality of different fluorophore-labeled oligonucleotide probe pairs comprises 4 probe pairs.

10. The method of claim 1, wherein the plurality of different fluorophore-labeled oligonucleotide probe pairs comprises 6 probe pairs.

11. The method of claim 1, wherein the single cell comprises at least 1000 mRNA species.

* * * * *